United States Patent
Chen et al.

(10) Patent No.: US 10,227,401 B2
(45) Date of Patent: *Mar. 12, 2019

(54) PRODUCTION CELL LINE ENHANCERS

(71) Applicant: REGENERON PHARMACEUTICALS, INC., Tarrytown, NY (US)

(72) Inventors: Gang Chen, Yorktown Heights, NY (US); Darya Burakov, Yonkers, NY (US); Dipali Deshpande, White Plains, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 418 days.

This patent is subject to a terminal disclaimer.

(21) Appl. No.: 14/737,090

(22) Filed: Jun. 11, 2015

(65) Prior Publication Data
US 2015/0353634 A1 Dec. 10, 2015

Related U.S. Application Data

(63) Continuation of application No. 13/904,587, filed on May 29, 2013, now Pat. No. 9,079,954.

(60) Provisional application No. 61/652,549, filed on May 29, 2012.

(51) Int. Cl.
| C07K 16/22 | (2006.01) |
| C12N 15/09 | (2006.01) |
| C12N 9/24 | (2006.01) |
| C07K 14/47 | (2006.01) |
| C07K 16/00 | (2006.01) |
| C12N 15/85 | (2006.01) |
| C12N 15/79 | (2006.01) |
| C12N 15/63 | (2006.01) |

(52) U.S. Cl.
CPC ............. *C07K 16/22* (2013.01); *C07K 14/47* (2013.01); *C07K 14/4705* (2013.01); *C07K 16/00* (2013.01); *C12N 9/2488* (2013.01); *C12N 15/09* (2013.01); *C12N 15/79* (2013.01); *C12N 15/85* (2013.01); *C12Y 302/01* (2013.01); *C07K 2317/14* (2013.01); *C07K 2317/51* (2013.01); *C07K 2317/515* (2013.01); *C12N 15/63* (2013.01); *C12N 2015/8518* (2013.01)

(58) Field of Classification Search
None
See application file for complete search history.

(56) References Cited

U.S. PATENT DOCUMENTS

| 9,079,954 B2 | 7/2015 | Chen et al. |
| 9,193,786 B2 | 11/2015 | Chen et al. |
| 9,228,012 B2 | 1/2016 | Chen et al. |
| 2004/0170622 A1 | 9/2004 | Glimcher et al. |
| 2010/0144013 A1 | 6/2010 | Goedegebuur et al. |
| 2011/0027286 A1 | 2/2011 | Thurston et al. |
| 2011/0142799 A1 | 6/2011 | Glimcher et al. |
| 2011/0159015 A1 | 6/2011 | Sleeman et al. |
| 2011/0293630 A1 | 12/2011 | Stitt et al. |
| 2013/0323788 A1 | 12/2013 | Chen et al. |
| 2015/0175688 A1 | 6/2015 | Chen et al. |
| 2015/0299309 A1 | 10/2015 | Chen et al. |
| 2015/0299310 A1 | 10/2015 | Chen et al. |

FOREIGN PATENT DOCUMENTS

| CN | 101426812 A | 5/2009 |
| WO | 2005/094355 A2 | 10/2005 |
| WO | 2006/014678 A2 | 2/2006 |
| WO | 2006/031931 A2 | 3/2006 |
| WO | 2009/058346 A1 | 5/2009 |
| WO | 2010/040508 A1 | 4/2010 |
| WO | 2011079257 A2 | 6/2011 |
| WO | 2011150008 A1 | 12/2011 |

OTHER PUBLICATIONS

Slominska-Wojewodzka M, The role of EDEM2 compared with EDEM1 in ricin transport from the endoplasmic reticulum to the cytosol, NCBI GenBank Accession ID:NM_145537.2, Feb. 15, 2015.

Olivari, S., et al. (2005) "A Novel Stress-induced EDEM Variant Regulating Endoplasmic Reticulum-associated Glycoprotein Degradation" J Biol Chem 280(4):2424-2428.

Schorpp, M., et al., 1996, "The human ubiquitin C promoter directs high ubiquitous expression of transgenes in Mice", Nucleic Acids Research, 24(9): 1787-1788.

Byun, H.-M., et al., 2005, "Plasmid vectors harboring cellular promoters can induce prolonged gene expression in hematopoietic and mesenchymal progenitor cells", Biochem Biophys Res Commun. 332(2): 518-23.

Ma, Y., et al., 2003, "The stressful road to antibody secretion", Nature Immunology, 4(4): 310-311.

Hansen, J. et al., 2003, "A large-scale, gene-driven mutagenesis approach for the functional analysis of the mouse genome", Proc Natl Acad Sci U.S.A. 100(17): 9918-9922.

Mast, SW et al., 2005, "Human EDEM2, a novel homolog of family 47 glycosidases, is involved in ER-associated degradation of glycoproteins", Glycobiology 15(4): 421-436.

(Continued)

*Primary Examiner* — Suzanne M Noakes
*Assistant Examiner* — Jae W Lee
(74) *Attorney, Agent, or Firm* — Scully, Scott, Murphy & Presser, P.C.; Macy C. Johnson

(57) ABSTRACT

The present invention relates to discovery of the ectopic expression of EDEM2 in a production cell to improve the yield of a useful multi-subunit protein. Thus, the present invention provides for production cell lines, such as the canonical mammalian biopharmaceutical production cell— the CHO cell, containing recombinant polynucleotides encoding EDEM2. Also disclosed is a production cell containing both an EDEM2-encoding polynucleotide as well an XBP1-encoding polynucleotide. Improved titers of antibodies produced by these cell lines are disclosed, as well as the improved cell densities attained by these cells in culture.

21 Claims, No Drawings
Specification includes a Sequence Listing.

(56) References Cited

OTHER PUBLICATIONS

Olivari, S. et al., 2005, "A Novel Stress-induced EDEM Variant Regulating Endoplasmic Reticulum-associated Glycoprotein Degradation", JBC 208(4): 2424-2428.

Olivari and Molinari, 2007, "Glycoprotein folding and the role of EDEM1, EDEM2 and EDEM3 in degradation of folding-defective glycoproteins", FEBS Lett. 581: 3658-3664.

Strausberg, RL, et al., 2002, "Generation and initial analysis of more than 15,000 full-length human and mouse cDNA sequences", Proc Natl Acad Sci U.S.A. 99(26): 16899-903. Epub Dec. 1, 2002.

Vembar, S.S. and Brodsky, J.L. 2008, "One step at a time: endoplasmic reticulum-associated degradation", Nature Rev Mol Cell Bio 9(12): 944-957. Published online Nov. 12, 2008.

Yoshida, H., et al., 2003, "A time-dependent phase shift in the mammalian unfolded protein response", Dev Cell. 4(2): 265-271.

Yoshida, H. et al., 2006, "XBP1 is critical to protect cells from endoplasmic reticulum stress: evidence from Site-2 protease-deficient Chinese hamster ovary cells", Cell Structure and Function 31(2): 117-125. Epub Nov. 17, 2006.

Eriksson, K.K. et al. 2004 "EDEM Contributes to Maintenance of Protein Folding Efficiency and Secretory Capacity" J Biol Chem 279(43):44600-44605.

Cain K. et al., "A CHO Cell Line Engineered to Express XBP1 and ERO1-Lα Has Increased Levels of Transient Protein Expression", Biotechnol. Prog. 29(3):697-706 (May-Jun. 2013).

Canadian Office Action dated Jun. 29, 2018 received in Canadian Patent Application No. 2,873,131.

SEQUENCE LISTING

```
<160> NUMBER OF SEQ ID NOS: 46

<210> SEQ ID NO 1
<211> LENGTH: 577
<212> TYPE: PRT
<213> ORGANISM: Mus musculus

<400> SEQUENCE: 1

Met Pro Phe Arg Leu Leu Ile Pro Leu Gly Leu Val Cys Val Leu Leu
1               5                   10                  15

Pro Leu His His Gly Ala Pro Gly Pro Asp Gly Thr Ala Pro Asp Pro
                20                  25                  30

Ala His Tyr Arg Glu Arg Val Lys Ala Met Phe Tyr His Ala Tyr Asp
            35                  40                  45

Ser Tyr Leu Glu Asn Ala Phe Pro Tyr Asp Glu Leu Arg Pro Leu Thr
        50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Thr Ser Glu Phe Gln Arg
                85                  90                  95

Val Val Glu Val Leu Gln Asp Asn Val Asp Phe Asp Ile Asp Val Asn
                100                 105                 110

Ala Ser Val Phe Glu Thr Asn Ile Arg Val Val Gly Gly Leu Leu Ser
```

```
                115                    120                    125
    Ala His Leu Leu Ser Lys Lys Ala Gly Val Glu Val Glu Ala Gly Trp
        130                    135                    140

Pro Cys Ser Gly Pro Leu Leu Arg Met Ala Glu Glu Ala Ala Arg Lys
    145                    150                    155                    160

Leu Leu Pro Ala Phe Gln Thr Pro Thr Gly Met Pro Tyr Gly Thr Val
                    165                    170                    175

Asn Leu Leu His Gly Val Asn Pro Gly Glu Thr Pro Val Thr Cys Thr
                180                    185                    190

Ala Gly Ile Gly Thr Phe Ile Val Glu Phe Ala Thr Leu Ser Ser Leu
            195                    200                    205

Thr Gly Asp Pro Val Phe Glu Asp Val Ala Arg Val Ala Leu Met Arg
    210                    215                    220

Leu Trp Glu Ser Arg Ser Asp Ile Gly Leu Val Gly Asn His Ile Asp
    225                    230                    235                    240

Val Leu Thr Gly Lys Trp Val Ala Gln Asp Ala Gly Ile Gly Ala Gly
                    245                    250                    255

Val Asp Ser Tyr Phe Glu Tyr Leu Val Lys Gly Ala Ile Leu Leu Gln
                260                    265                    270

Asp Lys Lys Leu Met Ala Met Phe Leu Glu Tyr Asn Lys Ala Ile Arg
            275                    280                    285

Asn Tyr Thr His Phe Asp Asp Trp Tyr Leu Trp Val Gln Met Tyr Lys
    290                    295                    300

Gly Thr Val Ser Met Pro Val Phe Gln Ser Leu Glu Ala Tyr Trp Pro
    305                    310                    315                    320

Gly Leu Gln Ser Leu Ile Gly Asp Ile Asp Asn Ala Met Arg Thr Phe
                    325                    330                    335

Leu Asn Tyr Tyr Thr Val Trp Lys Gln Phe Gly Gly Leu Pro Glu Phe
                340                    345                    350

Tyr Asn Ile Pro Gln Gly Tyr Thr Val Glu Lys Arg Glu Gly Tyr Pro
            355                    360                    365

Leu Arg Pro Glu Leu Ile Glu Ser Ala Met Tyr Leu Tyr Arg Ala Thr
    370                    375                    380

Gly Asp Pro Thr Leu Leu Glu Leu Gly Arg Asp Ala Val Glu Ser Ile
    385                    390                    395                    400

Glu Lys Ile Ser Lys Val Glu Cys Gly Phe Ala Thr Ile Lys Asp Leu
                    405                    410                    415

Arg Asp His Lys Leu Asp Asn Arg Met Glu Ser Phe Phe Leu Ala Glu
                420                    425                    430

Thr Val Lys Tyr Leu Tyr Leu Leu Phe His Pro Asn Asn Phe Ile His
            435                    440                    445

Asn Asn Gly Ser Thr Phe Asp Ser Val Met Thr Pro His Gly Glu Cys
    450                    455                    460

Ile Leu Gly Ala Gly Gly Tyr Ile Phe Asn Thr Glu Ala His Pro Ile
    465                    470                    475                    480

Asp Pro Ala Ala Leu His Cys Cys Arg Arg Leu Lys Glu Glu Gln Trp
                    485                    490                    495

Glu Val Glu Asp Leu Ile Lys Glu Phe Tyr Ser Leu Lys Gln Ser Arg
                500                    505                    510

Pro Lys Arg Ala Gln Arg Lys Thr Val Arg Ser Gly Pro Trp Glu Pro
            515                    520                    525

Gln Ser Gly Pro Ala Thr Leu Ser Pro Ala Asn Gln Pro Arg Glu
    530                    535                    540
```

```
Lys Gln Pro Ala Gln Gln Arg Thr Pro Leu Leu Ser Cys Pro Ser Gln
545                 550                 555                 560

Pro Phe Thr Ser Lys Leu Ala Leu Leu Gly Gln Val Phe Leu Asp Ser
                565                 570                 575

Ser

<210> SEQ ID NO 2
<211> LENGTH: 576
<212> TYPE: PRT
<213> ORGANISM: Rattus norvegicus

<400> SEQUENCE: 2

Met Pro Phe Arg Leu Leu Ile Pro Leu Gly Leu Val Cys Val Leu Leu
1               5                   10                  15

Pro Leu His His Gly Ala Pro Gly Pro Glu Gly Thr Ala Pro Asp Pro
                20                  25                  30

Ala His Tyr Arg Glu Arg Val Lys Ala Met Phe Tyr His Ala Tyr Asp
            35                  40                  45

Ser Tyr Leu Glu Asn Ala Phe Pro Tyr Asp Glu Leu Arg Pro Leu Thr
50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Thr Ser Glu Phe Gln Arg
                85                  90                  95

Val Val Glu Val Leu Gln Asp Asn Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
        275                 280                 285

Asn Tyr Thr His Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335
```

```
Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
            355                 360                 365

Leu Arg Pro Glu Leu Ile Glu Ser Ala Met Tyr Leu Tyr Arg Ala Thr
370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
            405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe His Pro Asn Asn Phe Ile His
            435                 440                 445

Asn Asn Gly Ser Thr Phe Asp Ser Val Met Thr Pro His Gly Glu Cys
            450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Arg Arg Leu Lys Glu Glu Gln Trp
            485                 490                 495

Glu Val Glu Asp Leu Ile Lys Glu Phe Tyr Ser Leu Arg Gln Ser Arg
            500                 505                 510

Ser Arg Ala Gln Arg Lys Thr Val Ser Ser Gly Pro Trp Glu Pro Pro
            515                 520                 525

Ala Gly Pro Gly Thr Leu Ser Ser Pro Glu Asn Gln Pro Arg Glu Lys
            530                 535                 540

Gln Pro Ala Arg Gln Arg Ala Pro Leu Leu Ser Cys Pro Ser Gln Pro
545                 550                 555                 560

Phe Thr Ser Lys Leu Ala Leu Leu Gly Gln Val Phe Leu Asp Ser Ser
            565                 570                 575

<210> SEQ ID NO 3
<211> LENGTH: 578
<212> TYPE: PRT
<213> ORGANISM: Cricetulus griseus

<400> SEQUENCE: 3

Met Pro Phe Arg Leu Leu Ile Pro Leu Gly Leu Val Cys Val Phe Leu
1               5                   10                  15

Pro Leu His His Gly Ala Pro Gly Pro Asp Gly Thr Ala Pro Asp Pro
            20                  25                  30

Ala His Tyr Arg Glu Arg Val Lys Ala Met Phe Tyr His Ala Tyr Asp
            35                  40                  45

Ser Tyr Leu Glu Asn Ala Phe Pro Tyr Asp Glu Leu Arg Pro Leu Thr
50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Thr Ser Glu Phe Gln Arg
            85                  90                  95

Val Val Glu Val Leu Gln Asp Asn Val Asp Phe Asp Ile Asp Val Asn
            100                 105                 110

Ala Ser Val Phe Glu Thr Asn Ile Arg Val Val Gly Gly Leu Leu Ser
            115                 120                 125

Ala His Leu Leu Ser Lys Lys Ala Gly Val Glu Val Glu Ala Gly Trp
```

-continued

```
                130                 135                 140
Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
                180                 185                 190

Ala Gly Ile Gly Thr Phe Ile Val Glu Phe Ala Thr Leu Ser Ser Leu
                195                 200                 205

Thr Gly Asp Pro Val Phe Glu Asp Val Ala Arg Leu Ala Leu Met Arg
                210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
                260                 265                 270

Asp Lys Lys Leu Met Ala Met Phe Leu Glu Tyr Asn Arg Ala Ile Arg
                275                 280                 285

Asn Tyr Thr His Phe Asp Asp Trp Tyr Leu Trp Val Gln Met Tyr Lys
                290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
                340                 345                 350

Tyr Asn Ile Ala Gln Gly Tyr Thr Val Glu Lys Arg Gly Tyr Pro
                355                 360                 365

Leu Arg Pro Glu Leu Ile Glu Ser Ala Met Tyr Leu Tyr Arg Ala Thr
                370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
                420                 425                 430

Thr Val Lys Tyr Leu Tyr Leu Leu Phe His Pro Asn Asn Phe Ile His
                435                 440                 445

Asn Asn Gly Ser Thr Phe Asp Ser Val Met Thr Pro His Gly Glu Cys
450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Arg Arg Leu Lys Glu Glu Gln Trp
                485                 490                 495

Glu Val Glu Asp Leu Met Arg Glu Leu His Ser Leu Lys Gln Ser Arg
                500                 505                 510

Ser Arg Ala Gln Arg Lys Thr Thr Ser Ser Gly Pro Trp Glu Pro Pro
                515                 520                 525

Ala Gly Pro Gly Ser Pro Ser Ala Pro Gly Lys Gln Asp Gln Pro Arg
                530                 535                 540

Glu Lys Gln Pro Ala Lys Gln Arg Thr Pro Leu Leu Ser Cys Pro Ser
545                 550                 555                 560
```

```
Gln Pro Phe Thr Ser Lys Leu Ala Leu Leu Gly Gln Val Phe Leu Asp
                565                 570                 575

Ser Ser

<210> SEQ ID NO 4
<211> LENGTH: 578
<212> TYPE: PRT
<213> ORGANISM: Homo sapiens

<400> SEQUENCE: 4

Met Pro Phe Arg Leu Leu Ile Pro Leu Gly Leu Leu Cys Ala Leu Leu
1               5                   10                  15

Pro Gln His His Gly Ala Pro Gly Pro Asp Gly Ser Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Phe Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Val Ser Glu Phe Gln Arg
                85                  90                  95

Val Val Glu Val Leu Gln Asp Ser Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
        275                 280                 285

Asn Tyr Thr Arg Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350
```

```
Tyr Asn Ile Pro Gln Gly Tyr Thr Val Glu Lys Arg Glu Gly Tyr Pro
            355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Phe Asp Pro Thr Asn Phe Ile His
        435                 440                 445

Asn Asn Gly Ser Thr Phe Asp Thr Val Ile Thr Pro Tyr Gly Glu Cys
    450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Gln Arg Leu Lys Glu Glu Gln Trp
                485                 490                 495

Glu Val Glu Asp Leu Met Arg Glu Phe Tyr Ser Leu Arg Ser Arg
            500                 505                 510

Ser Lys Phe Gln Lys Asn Thr Val Ser Ser Gly Pro Trp Glu Pro Pro
    515                 520                 525

Ala Arg Pro Gly Thr Leu Phe Ser Pro Glu Asn His Asp Gln Ala Arg
    530                 535                 540

Glu Arg Lys Pro Ala Lys Gln Lys Val Pro Leu Leu Ser Cys Pro Ser
545                 550                 555                 560

Gln Pro Phe Thr Ser Lys Leu Ala Leu Leu Gly Gln Val Phe Leu Asp
                565                 570                 575

Ser Ser

<210> SEQ ID NO 5
<211> LENGTH: 578
<212> TYPE: PRT
<213> ORGANISM: Pan troglodytes

<400> SEQUENCE: 5

Met Pro Phe Arg Leu Leu Ile Pro Leu Gly Leu Leu Cys Ala Leu Leu
1               5                   10                  15

Pro Leu His His Gly Ala Pro Gly Pro Asp Gly Ser Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Phe Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Val Ser Glu Phe Gln Arg
                85                  90                  95

Val Val Glu Val Leu Gln Asp Ser Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140
```

```
Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
            165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
            195                 200                 205

Thr Gly Asp Pro Val Phe Glu Asp Val Ala Arg Val Ala Leu Met Arg
            210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
            245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
            275                 280                 285

Asn Tyr Thr Arg Phe Asp Asp Trp Tyr Leu Trp Val Gln Met Tyr Lys
            290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
            325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
            355                 360                 365

Leu Arg Pro Glu Leu Ile Glu Ser Ala Met Tyr Leu Tyr Arg Ala Thr
            370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
            405                 410                 415

Arg Asp His Lys Leu Asp Asn Arg Met Glu Ser Phe Phe Leu Ala Glu
            420                 425                 430

Thr Val Lys Tyr Leu Tyr Leu Phe Asp Pro Thr Asn Phe Ile His
            435                 440                 445

Asn Asn Gly Ser Thr Phe Asp Ala Val Ile Thr Pro Tyr Gly Glu Cys
450                 455                 460

Ile Leu Gly Ala Gly Tyr Ile Phe Asn Thr Glu Ala His Pro Ile
465                 470                 475                 480

Asp Pro Ala Ala Leu His Cys Cys Gln Arg Leu Lys Glu Glu Gln Trp
            485                 490                 495

Glu Val Glu Asp Leu Met Arg Glu Phe Tyr Ser Leu Lys Arg Ser Arg
            500                 505                 510

Ser Lys Phe Gln Lys Lys Thr Val Ser Ser Gly Pro Trp Glu Pro Pro
            515                 520                 525

Ala Arg Pro Gly Thr Leu Phe Ser Pro Glu Asn His Asp Gln Ala Arg
            530                 535                 540

Glu Arg Lys Pro Ala Lys Gln Lys Val Pro Leu Leu Ser Cys Pro Ser
545                 550                 555                 560
```

```
Gln Pro Phe Thr Ser Lys Leu Ala Leu Leu Gly Gln Val Phe Leu Asp
                565                 570                 575

Ser Ser

<210> SEQ ID NO 6
<211> LENGTH: 513
<212> TYPE: PRT
<213> ORGANISM: Pongo pygmaeus

<400> SEQUENCE: 6

Met Asn Thr Leu Ser Cys Ser Leu Phe Ser Leu Thr Leu Ile Asp Ala
1               5                   10                  15

Leu Asp Thr Leu Leu Ile Leu Gly Asn Val Ser Glu Phe Gln Arg Val
            20                  25                  30

Val Glu Val Leu Gln Asp Asn Val Asp Phe Asp Ile Asp Val Asn Ala
        35                  40                  45

Ser Val Phe Glu Thr Asn Ile Arg Val Val Gly Gly Leu Leu Ser Ala
    50                  55                  60

His Leu Leu Ser Lys Lys Ala Gly Val Glu Val Ala Gly Trp Pro
65                  70                  75                  80

Cys Ser Gly Pro Leu Leu Arg Met Ala Glu Glu Ala Ala Arg Lys Leu
                85                  90                  95

Leu Pro Ala Phe Gln Thr Pro Thr Gly Met Pro Tyr Gly Thr Val Asn
            100                 105                 110

Leu Leu His Gly Val Asn Pro Gly Glu Thr Pro Val Thr Cys Thr Ala
        115                 120                 125

Gly Ile Gly Thr Phe Ile Val Glu Phe Ala Thr Leu Ser Ser Leu Thr
    130                 135                 140

Gly Asp Pro Val Phe Glu Asp Val Ala Arg Val Ala Leu Met Arg Leu
145                 150                 155                 160

Trp Glu Ser Arg Ser Asp Ile Gly Leu Val Gly Asn His Ile Asp Val
                165                 170                 175

Leu Thr Gly Lys Trp Val Ala Gln Asp Ala Gly Ile Gly Ala Gly Val
            180                 185                 190

Asp Ser Tyr Phe Glu Tyr Leu Val Lys Gly Ala Ile Leu Leu Gln Asp
        195                 200                 205

Lys Lys Leu Met Ala Met Phe Leu Glu Tyr Asn Lys Ala Ile Arg Asn
    210                 215                 220

Tyr Thr Arg Phe Asp Asp Trp Tyr Leu Trp Val Gln Met Tyr Lys Gly
225                 230                 235                 240

Thr Val Ser Met Pro Val Phe Gln Ser Leu Glu Ala Tyr Trp Pro Gly
                245                 250                 255

Leu Gln Ser Leu Ile Gly Asp Ile Asp Asn Ala Met Arg Thr Phe Leu
            260                 265                 270

Asn Tyr Tyr Thr Val Trp Lys Gln Phe Gly Gly Leu Pro Glu Phe Tyr
        275                 280                 285

Asn Ile Pro Gln Gly Tyr Thr Val Glu Lys Arg Glu Gly Tyr Pro Leu
    290                 295                 300

Arg Pro Glu Leu Ile Glu Ser Ala Met Tyr Leu Tyr Arg Ala Thr Gly
305                 310                 315                 320

Asp Pro Thr Leu Leu Glu Leu Gly Arg Asp Ala Val Glu Ser Ile Glu
                325                 330                 335

Lys Ile Ser Lys Val Glu Cys Gly Phe Ala Thr Ile Lys Asp Leu Arg
            340                 345                 350
```

-continued

```
Asp His Lys Leu Asp Asn Arg Met Glu Ser Phe Phe Leu Ala Glu Thr
            355                 360                 365

Val Lys Tyr Leu Tyr Leu Phe Asp Pro Thr Asn Phe Ile His Asn
    370                 375                 380

Asn Gly Ser Thr Phe Asp Ala Val Ile Thr Pro Tyr Gly Glu Cys Ile
385                 390                 395                 400

Leu Gly Ala Gly Gly Tyr Ile Phe Asn Thr Glu Ala His Pro Ile Asp
                405                 410                 415

Pro Ala Ala Leu His Cys Cys Gln Arg Leu Lys Glu Glu Gln Trp Glu
            420                 425                 430

Val Glu Asp Leu Met Arg Glu Phe Tyr Ser Leu Lys Arg Asn Arg Ser
    435                 440                 445

Lys Phe Gln Lys Lys Thr Val Ser Ser Gly Pro Trp Glu Pro Pro Ala
    450                 455                 460

Arg Pro Gly Thr Leu Phe Ser Pro Glu Asn His Asp Gln Ala Arg Gly
465                 470                 475                 480

Arg Lys Pro Ala Lys Gln Lys Val Pro Leu Leu Ser Cys Pro Ser Gln
                485                 490                 495

Pro Phe Thr Ser Lys Leu Ala Leu Leu Gly Gln Val Phe Leu Asp Ser
            500                 505                 510

Ser
```

<210> SEQ ID NO 7
<211> LENGTH: 572
<212> TYPE: PRT
<213> ORGANISM: Danio rerio

<400> SEQUENCE: 7

```
Leu Tyr Tyr Leu Pro Leu Phe Thr Ser Arg Tyr Phe Met Leu Thr Phe
1               5                   10                  15

Leu Phe Ser Ala Ile Phe Cys Ala Ala Tyr Leu Ser Pro Ile Ile Ser
            20                  25                  30

His Val Lys Gly Arg Asp Phe Thr Glu Gln Glu Met Ser His Tyr Arg
        35                  40                  45

Asp Arg Val Lys Ser Met Phe Tyr His Ala Tyr Asn Ser Tyr Leu Asp
    50                  55                  60

Asn Ala Tyr Pro Tyr Asp Glu Leu Arg Pro Leu Thr Cys Asp Gly Gln
65                  70                  75                  80

Asp Thr Trp Gly Ser Phe Ser Leu Thr Leu Ile Asp Ala Leu Asp Thr
                85                  90                  95

Leu Leu Ile Leu Gly Asn His Thr Glu Phe Gln Arg Val Ala Thr Leu
            100                 105                 110

Leu Gln Asp Thr Val Asp Phe Asp Ile Asp Val Asn Ala Ser Val Phe
        115                 120                 125

Glu Thr Asn Ile Arg Val Val Gly Gly Leu Leu Ser Ala His Leu Leu
    130                 135                 140

Ser Lys Arg Ala Gly Met Lys Val Glu Glu Gly Trp Pro Cys Ser Gly
145                 150                 155                 160

Pro Leu Leu Arg Met Ala Glu Asp Ala Ala Arg Lys Leu Leu Pro Ala
                165                 170                 175

Phe Gln Thr Pro Thr Gly Met Pro Tyr Gly Thr Val Asn Leu Leu Arg
            180                 185                 190

Gly Val Asn Pro Gly Glu Thr Pro Val Thr Cys Thr Ala Gly Val Gly
        195                 200                 205
```

Thr Phe Ile Leu Glu Phe Ser Thr Leu Ser Arg Leu Thr Gly Asp Pro
210                 215                 220

Val Phe Glu Asn Val Ala Arg Lys Ala Leu Arg Ala Leu Trp Arg Thr
225                 230                 235                 240

Arg Ser Asp Ile Gly Leu Val Gly Asn His Ile Asp Val Ile Thr Ser
            245                 250                 255

Lys Trp Val Ala Gln Asp Ala Gly Ile Gly Ala Gly Val Asp Ser Tyr
        260                 265                 270

Phe Glu Tyr Leu Val Arg Gly Ala Ile Met Leu Gln Asp Glu Glu Leu
    275                 280                 285

Leu Thr Met Phe Tyr Glu Phe Asp Lys Ser Ile Lys Asn Tyr Thr Lys
290                 295                 300

Phe Asp Asp Trp Tyr Leu Trp Val Gln Met His Lys Gly Thr Val Ser
305                 310                 315                 320

Met Pro Val Phe Gln Ser Leu Glu Ala Phe Trp Pro Gly Met Gln Ser
            325                 330                 335

Leu Ile Gly Asp Ile Ser Ser Ala Thr Lys Ser Phe His Asn Tyr Tyr
        340                 345                 350

Ser Val Trp Arg Gln Phe Gly Gly Leu Pro Glu Phe Tyr Ser Ile Pro
    355                 360                 365

Gln Gly Tyr Thr Val Asp Lys Arg Glu Gly Tyr Pro Leu Arg Pro Glu
370                 375                 380

Leu Ile Glu Ser Ala Met Tyr Leu Tyr Lys Ala Thr Gly Asp Pro Ser
385                 390                 395                 400

Phe Ile Gln Leu Gly Arg Asp Ala Val Glu Ser Ile Asp Arg Ile Ser
            405                 410                 415

Arg Val Asn Cys Gly Phe Ala Thr Val Lys Asp Val Arg Asp His Lys
        420                 425                 430

Leu Asp Asn Arg Met Glu Ser Phe Phe Leu Ala Glu Thr Ile Lys Tyr
    435                 440                 445

Leu Tyr Leu Leu Phe Asp Pro Asp Asn Phe Leu His Asn Thr Gly Thr
450                 455                 460

Glu Phe Glu Leu Gly Gly Leu Arg Gly Asp Cys Ile Leu Ser Ala Gly
465                 470                 475                 480

Gly Tyr Val Phe Asn Thr Glu Ala His Pro Leu Asp Pro Ala Ala Leu
            485                 490                 495

His Cys Cys Ser Arg Glu Gln Gln Asp Arg Arg Glu Ile Gln Asp Ile
        500                 505                 510

Leu Leu Ser Phe Ser Gln Pro His Thr Glu Glu Pro Ser Arg Asp Gln
    515                 520                 525

Ser Ala Gly Gly Ser Pro Glu Ser Ile Ala Leu Lys Pro Gly Glu Gln
530                 535                 540

Arg Lys Ala Pro Val Leu Ser Cys Pro Thr Gln Pro Phe Ser Ala Lys
545                 550                 555                 560

Leu Ala Val Met Gly Gln Val Phe Ser Asp Asn Ser
            565                 570

<210> SEQ ID NO 8
<211> LENGTH: 579
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (12)..(12)

```
<223> OTHER INFORMATION: V or L
<220> FEATURE:
<221> NAME/KEY: MISC_FEATURE
<222> LOCATION: (14)..(14)
<223> OTHER INFORMATION: V or A
<220> FEATURE:
<221> NAME/KEY: MISC_FEATURE
<222> LOCATION: (15)..(15)
<223> OTHER INFORMATION: L or F
<220> FEATURE:
<221> NAME/KEY: MISC_FEATURE
<222> LOCATION: (26)..(26)
<223> OTHER INFORMATION: D or E
<220> FEATURE:
<221> NAME/KEY: MISC_FEATURE
<222> LOCATION: (28)..(28)
<223> OTHER INFORMATION: T or S
<220> FEATURE:
<221> NAME/KEY: MISC_FEATURE
<222> LOCATION: (57)..(57)
<223> OTHER INFORMATION: Y or F
<220> FEATURE:
<221> NAME/KEY: MISC_FEATURE
<222> LOCATION: (91)..(91)
<223> OTHER INFORMATION: T or V
<220> FEATURE:
<221> NAME/KEY: MISC_FEATURE
<222> LOCATION: (104)..(104)
<223> OTHER INFORMATION: N or S
<220> FEATURE:
<221> NAME/KEY: MISC_FEATURE
<222> LOCATION: (220)..(220)
<223> OTHER INFORMATION: V or L
<220> FEATURE:
<221> NAME/KEY: MISC_FEATURE
<222> LOCATION: (285)..(285)
<223> OTHER INFORMATION: K or R
<220> FEATURE:
<221> NAME/KEY: MISC_FEATURE
<222> LOCATION: (292)..(292)
<223> OTHER INFORMATION: H or R
<220> FEATURE:
<221> NAME/KEY: MISC_FEATURE
<222> LOCATION: (356)..(356)
<223> OTHER INFORMATION: P or A
<220> FEATURE:
<221> NAME/KEY: MISC_FEATURE
<222> LOCATION: (442)..(442)
<223> OTHER INFORMATION: H or D
<220> FEATURE:
<221> NAME/KEY: MISC_FEATURE
<222> LOCATION: (444)..(444)
<223> OTHER INFORMATION: N or T
<220> FEATURE:
<221> NAME/KEY: MISC_FEATURE
<222> LOCATION: (456)..(456)
<223> OTHER INFORMATION: S, T, or A
<220> FEATURE:
<221> NAME/KEY: MISC_FEATURE
<222> LOCATION: (458)..(458)
<223> OTHER INFORMATION: M or I
<220> FEATURE:
<221> NAME/KEY: MISC_FEATURE
<222> LOCATION: (461)..(461)
<223> OTHER INFORMATION: H or Y
<220> FEATURE:
<221> NAME/KEY: MISC_FEATURE
<222> LOCATION: (489)..(489)
<223> OTHER INFORMATION: R or Q
<220> FEATURE:
<221> NAME/KEY: MISC_FEATURE
<222> LOCATION: (502)..(502)
<223> OTHER INFORMATION: I or M
<220> FEATURE:
<221> NAME/KEY: MISC_FEATURE
<222> LOCATION: (503)..(503)
<223> OTHER INFORMATION: K or R
<220> FEATURE:
<221> NAME/KEY: MISC_FEATURE
```

```
<222> LOCATION: (505)..(505)
<223> OTHER INFORMATION: F or L
<220> FEATURE:
<221> NAME/KEY: MISC_FEATURE
<222> LOCATION: (506)..(506)
<223> OTHER INFORMATION: Y or H
<220> FEATURE:
<221> NAME/KEY: MISC_FEATURE
<222> LOCATION: (509)..(509)
<223> OTHER INFORMATION: K or R
<220> FEATURE:
<221> NAME/KEY: MISC_FEATURE
<222> LOCATION: (510)..(510)
<223> OTHER INFORMATION: Q or R
<220> FEATURE:
<221> NAME/KEY: MISC_FEATURE
<222> LOCATION: (513)..(513)
<223> OTHER INFORMATION: P or S
<220> FEATURE:
<221> NAME/KEY: MISC_FEATURE
<222> LOCATION: (514)..(516)
<223> OTHER INFORMATION: KRA, RA, or KF (one amino acid may be missing)
<220> FEATURE:
<221> NAME/KEY: MISC_FEATURE
<222> LOCATION: (518)..(518)
<223> OTHER INFORMATION: R or K
<220> FEATURE:
<221> NAME/KEY: MISC_FEATURE
<222> LOCATION: (519)..(519)
<223> OTHER INFORMATION: K or N
<220> FEATURE:
<221> NAME/KEY: MISC_FEATURE
<222> LOCATION: (522)..(522)
<223> OTHER INFORMATION: R or S
<220> FEATURE:
<221> NAME/KEY: MISC_FEATURE
<222> LOCATION: (529)..(529)
<223> OTHER INFORMATION: Q or P
<220> FEATURE:
<221> NAME/KEY: MISC_FEATURE
<222> LOCATION: (530)..(530)
<223> OTHER INFORMATION: S or A
<220> FEATURE:
<221> NAME/KEY: MISC_FEATURE
<222> LOCATION: (531)..(531)
<223> OTHER INFORMATION: G or R
<220> FEATURE:
<221> NAME/KEY: MISC_FEATURE
<222> LOCATION: (533)..(533)
<223> OTHER INFORMATION: A or G
<220> FEATURE:
<221> NAME/KEY: MISC_FEATURE
<222> LOCATION: (534)..(534)
<223> OTHER INFORMATION: T or S
<220> FEATURE:
<221> NAME/KEY: MISC_FEATURE
<222> LOCATION: (535)..(535)
<223> OTHER INFORMATION: L or P
<220> FEATURE:
<221> NAME/KEY: MISC_FEATURE
<222> LOCATION: (536)..(536)
<223> OTHER INFORMATION: S or F
<220> FEATURE:
<221> NAME/KEY: MISC_FEATURE
<222> LOCATION: (537)..(537)
<223> OTHER INFORMATION: S or A
<220> FEATURE:
<221> NAME/KEY: MISC_FEATURE
<222> LOCATION: (539)..(542)
<223> OTHER INFORMATION: AN, EN, GKQD, or ENHD (two amino acids may be
      missing)
<220> FEATURE:
<221> NAME/KEY: MISC_FEATURE
<222> LOCATION: (544)..(544)
<223> OTHER INFORMATION: P or A
<220> FEATURE:
<221> NAME/KEY: MISC_FEATURE
<222> LOCATION: (547)..(547)
<223> OTHER INFORMATION: K or R
```

```
<220> FEATURE:
<221> NAME/KEY: MISC_FEATURE
<222> LOCATION: (548)..(548)
<223> OTHER INFORMATION: Q or K
<220> FEATURE:
<221> NAME/KEY: MISC_FEATURE
<222> LOCATION: (551)..(551)
<223> OTHER INFORMATION: Q, R, or K
<220> FEATURE:
<221> NAME/KEY: MISC_FEATURE
<222> LOCATION: (553)..(553)
<223> OTHER INFORMATION: R or K
<220> FEATURE:
<221> NAME/KEY: MISC_FEATURE
<222> LOCATION: (554)..(554)
<223> OTHER INFORMATION: T, A, or V

<400> SEQUENCE: 8
```

Met Pro Phe Arg Leu Leu Ile Pro Leu Gly Leu Xaa Cys Xaa Xaa Leu
1               5                   10                  15

Pro Leu His His Gly Ala Pro Gly Pro Xaa Gly Xaa Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Xaa Asp Leu Arg Pro Leu Thr
50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Xaa Ser Glu Phe Gln Arg
            85                  90                  95

Val Val Glu Val Leu Gln Asp Xaa Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
            165                 170                 175

Asn Leu Leu His Gly Val Asn Pro Gly Glu Thr Pro Val Thr Cys Thr
        180                 185                 190

Ala Gly Ile Gly Thr Phe Ile Val Glu Phe Ala Thr Leu Ser Ser Leu
    195                 200                 205

Thr Gly Asp Pro Val Phe Glu Asp Val Ala Arg Xaa Ala Leu Met Arg
210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
            245                 250                 255

Val Asp Ser Tyr Phe Glu Tyr Leu Val Lys Gly Ala Ile Leu Leu Gln
        260                 265                 270

Asp Lys Lys Leu Met Ala Met Phe Leu Glu Tyr Asn Xaa Ala Ile Arg
    275                 280                 285

Asn Tyr Thr Xaa Phe Asp Asp Trp Tyr Leu Trp Val Gln Met Tyr Lys
290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
            325                 330                 335

Leu Asn Tyr Tyr Thr Val Trp Lys Gln Phe Gly Gly Leu Pro Glu Phe
        340                 345                 350

Tyr Asn Ile Xaa Gln Gly Tyr Thr Val Glu Lys Arg Glu Gly Tyr Pro
    355                 360                 365

Leu Arg Pro Glu Leu Ile Glu Ser Ala Met Tyr Leu Tyr Arg Ala Thr
370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe Xaa Pro Xaa Asn Phe Ile His
        435                 440                 445

Asn Asn Gly Ser Thr Phe Asp Xaa Val Xaa Thr Pro Xaa Gly Glu Cys
    450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Xaa Arg Leu Lys Glu Glu Gln Trp
                485                 490                 495

Glu Val Glu Asp Leu Xaa Xaa Glu Xaa Xaa Ser Leu Xaa Xaa Ser Arg
            500                 505                 510

Xaa Xaa Xaa Xaa Gln Xaa Xaa Thr Val Xaa Ser Gly Pro Trp Glu Pro
        515                 520                 525

Xaa Xaa Xaa Pro Xaa Xaa Xaa Xaa Pro Xaa Xaa Xaa Xaa Gln Xaa
    530                 535                 540

Arg Glu Xaa Xaa Pro Ala Xaa Gln Xaa Xaa Pro Leu Leu Ser Cys Pro
545                 550                 555                 560

Ser Gln Pro Phe Thr Ser Lys Leu Ala Leu Leu Gly Gln Val Phe Leu
                565                 570                 575

Asp Ser Ser

<210> SEQ ID NO 9
<211> LENGTH: 371
<212> TYPE: PRT
<213> ORGANISM: Mus musculus

<400> SEQUENCE: 9

Met Val Val Val Ala Ala Ala Pro Ser Ala Thr Ala Ala Pro Lys
1               5                   10                  15

Val Leu Leu Leu Ser Gly Gln Pro Ala Ser Gly Gly Arg Ala Leu Pro
            20                  25                  30

Leu Met Val Pro Gly Pro Arg Ala Ala Gly Ser Glu Ala Ser Gly Thr
        35                  40                  45

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn His Lys Leu Gln Leu Glu Asn Gln Leu Leu
            100                 105                 110

```
Arg Glu Lys Thr His Gly Leu Val Glu Asn Gln Glu Leu Arg Thr
            115                 120                 125

Arg Leu Gly Met Asp Thr Leu Asp Pro Asp Glu Val Pro Val Glu
130                 135                 140

Ala Lys Gly Ser Gly Val Arg Leu Val Ala Gly Ser Ala Glu Ser Ala
145                 150                 155                 160

Ala Gly Ala Gly Pro Val Val Thr Ser Pro Glu His Leu Pro Met Asp
                165                 170                 175

Ser Asp Thr Val Ala Ser Ser Asp Ser Glu Ser Asp Ile Leu Leu Gly
            180                 185                 190

Ile Leu Asp Lys Leu Asp Pro Val Met Phe Phe Lys Cys Pro Ser Pro
            195                 200                 205

Glu Ser Ala Ser Leu Glu Glu Leu Pro Glu Val Tyr Pro Glu Gly Pro
            210                 215                 220

Ser Ser Leu Pro Ala Ser Leu Ser Leu Ser Val Gly Thr Ser Ser Ala
225                 230                 235                 240

Lys Leu Glu Ala Ile Asn Glu Leu Ile Arg Phe Asp His Val Tyr Thr
                245                 250                 255

Lys Pro Leu Val Leu Glu Ile Pro Ser Glu Thr Glu Ser Gln Thr Asn
            260                 265                 270

Val Val Val Lys Ile Glu Glu Ala Pro Leu Ser Ser Ser Glu Glu Asp
            275                 280                 285

His Pro Glu Phe Ile Val Ser Val Lys Lys Glu Pro Leu Glu Asp Asp
            290                 295                 300

Phe Ile Pro Glu Leu Gly Ile Ser Asn Leu Leu Ser Ser Ser His Cys
305                 310                 315                 320

Leu Arg Pro Pro Ser Cys Leu Leu Asp Ala His Ser Asp Cys Gly Tyr
                325                 330                 335

Glu Gly Ser Pro Ser Pro Phe Ser Asp Met Ser Ser Pro Leu Gly Thr
            340                 345                 350

Asp His Ser Trp Glu Asp Thr Phe Ala Asn Glu Leu Phe Pro Gln Leu
            355                 360                 365

Ile Ser Val
    370

<210> SEQ ID NO 10
<211> LENGTH: 369
<212> TYPE: PRT
<213> ORGANISM: Cricetulus griseus

<400> SEQUENCE: 10

Met Val Val Val Ala Ala Ser Pro Ser Ala Ala Thr Ala Ala Pro Lys
1               5                   10                  15

Val Leu Leu Leu Ser Gly Gln Pro Ala Ala Asp Gly Arg Ala Leu Pro
            20                  25                  30

Leu Met Val Pro Gly Ser Arg Ala Ala Gly Ser Glu Ala Asn Gly Ala
        35                  40                  45

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn Gln Lys Leu Leu Leu Glu Asn Gln Leu Leu
            100                 105                 110
```

```
Arg Glu Lys Thr His Gly Leu Val Ile Glu Asn Gln Glu Leu Arg Thr
            115                 120                 125

Arg Leu Gly Met Asp Val Leu Thr Thr Glu Glu Ala Pro Glu Thr Glu
        130                 135                 140

Ser Lys Gly Asn Gly Val Arg Pro Val Ala Gly Ser Ala Glu Ser Ala
145                 150                 155                 160

Ala Gly Ala Gly Pro Val Val Thr Ser Pro Glu His Leu Pro Met Asp
                165                 170                 175

Ser Asp Thr Val Asp Ser Ser Asp Ser Glu Ser Asp Ile Leu Leu Gly
            180                 185                 190

Ile Leu Asp Lys Leu Asp Pro Val Met Phe Phe Lys Cys Pro Ser Pro
        195                 200                 205

Glu Ser Ala Asn Leu Glu Glu Leu Pro Glu Val Tyr Pro Gly Pro Ser
210                 215                 220

Ser Leu Pro Ala Ser Leu Ser Leu Ser Val Gly Thr Ser Ser Ala Lys
225                 230                 235                 240

Leu Glu Ala Ile Asn Glu Leu Ile Arg Phe Asp His Val Tyr Thr Lys
                245                 250                 255

Pro Leu Val Leu Glu Ile Pro Ser Glu Thr Glu Ser Gln Thr Asn Val
            260                 265                 270

Val Val Lys Ile Glu Glu Ala Pro Leu Ser Ser Ser Glu Glu Asp His
        275                 280                 285

Pro Glu Phe Ile Val Ser Val Lys Lys Glu Pro Glu Glu Asp Phe Ile
290                 295                 300

Pro Glu Pro Gly Ile Ser Asn Leu Leu Ser Ser Ser His Cys Leu Lys
305                 310                 315                 320

Pro Ser Ser Cys Leu Leu Asp Ala Tyr Ser Asp Cys Gly Tyr Glu Gly
                325                 330                 335

Ser Pro Ser Pro Phe Ser Asp Met Ser Ser Pro Leu Gly Ile Asp His
            340                 345                 350

Ser Trp Glu Asp Thr Phe Ala Asn Glu Leu Phe Pro Gln Leu Ile Ser
        355                 360                 365

Val

<210> SEQ ID NO 11
<211> LENGTH: 376
<212> TYPE: PRT
<213> ORGANISM: Homo sapiens

<400> SEQUENCE: 11

Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110
```

```
Leu Leu Glu Asn Gln Leu Leu Arg Glu Lys Thr His Gly Leu Val Val
            115                 120                 125

Glu Asn Gln Glu Leu Arg Gln Arg Leu Gly Met Asp Ala Leu Val Ala
        130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Asp Ser Glu Ser
            180                 185                 190

Asp Ile Leu Leu Gly Ile Leu Asp Asn Leu Asp Pro Val Met Phe Phe
        195                 200                 205

Lys Cys Pro Ser Pro Glu Pro Ala Ser Leu Glu Glu Leu Pro Glu Val
    210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
            260                 265                 270

Glu Ser Gln Ala Asn Val Val Lys Ile Glu Glu Ala Pro Leu Ser
        275                 280                 285

Pro Ser Glu Asn Asp His Pro Glu Phe Ile Val Ser Val Lys Glu Glu
    290                 295                 300

Pro Val Glu Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
        355                 360                 365

Leu Phe Pro Gln Leu Ile Ser Val
            370                 375

<210> SEQ ID NO 12
<211> LENGTH: 383
<212> TYPE: PRT
<213> ORGANISM: Danio rerio

<400> SEQUENCE: 12

Met Val Val Val Thr Ala Gly Thr Gly Gly Ala His Lys Val Leu Leu
1               5                   10                  15

Ile Ser Gly Lys Gln Ser Ala Ser Thr Gly Ala Thr Gln Gly Gly Tyr
            20                  25                  30

Ser Arg Ser Ile Ser Val Met Ile Pro Asn Gln Ala Ser Ser Asp Ser
        35                  40                  45

Asp Ser Thr Thr Ser Gly Pro Pro Leu Arg Lys Arg Gln Arg Leu Thr
    50                  55                  60

His Leu Ser Pro Glu Glu Lys Ala Leu Arg Arg Lys Leu Lys Asn Arg
65                  70                  75                  80

Val Ala Ala Gln Thr Ala Arg Asp Arg Lys Lys Ala Lys Met Gly Glu
                85                  90                  95

Leu Glu Gln Gln Val Leu Glu Leu Glu Leu Glu Asn Gln Lys Leu His
```

```
            100                 105                 110
Val Glu Asn Arg Leu Leu Arg Asp Lys Thr Ser Asp Leu Leu Ser Glu
        115                 120                 125

Asn Glu Glu Leu Arg Gln Arg Leu Gly Leu Asp Thr Leu Glu Thr Lys
    130                 135                 140

Glu Gln Val Gln Val Leu Glu Ser Ala Val Ser Asp Leu Gly Leu Val
145                 150                 155                 160

Thr Gly Ser Ser Glu Ser Ala Ala Gly Ala Gly Pro Ala Val Pro Lys
                165                 170                 175

Ser Glu Asp Phe Thr Met Asp Thr His Ser Pro Gly Pro Ala Asp Ser
            180                 185                 190

Glu Ser Asp Leu Leu Leu Gly Ile Leu Asp Ile Leu Asp Pro Glu Leu
        195                 200                 205

Phe Leu Lys Thr Asp Leu Pro Glu Ala Gln Glu Pro Gln Gln Glu Leu
    210                 215                 220

Val Leu Val Gly Gly Ala Gly Glu Gln Val Pro Ser Ser Ala Pro Ala
225                 230                 235                 240

Ala Leu Gly Pro Ala Pro Val Lys Leu Glu Ala Leu Asn Glu Leu Ile
                245                 250                 255

His Phe Asp His Ile Tyr Thr Lys Pro Ala Glu Val Leu Val Ser Glu
            260                 265                 270

Glu Ser Ile Cys Glu Val Lys Ala Glu Asp Ser Val Ala Phe Ser Glu
        275                 280                 285

Thr Glu Glu Glu Ile Gln Val Glu Asp Gln Thr Val Ser Val Lys Asp
    290                 295                 300

Glu Pro Glu Glu Val Val Ile Pro Ala Glu Asn Gln Asn Pro Asp Ala
305                 310                 315                 320

Ala Asp Asp Phe Leu Ser Asp Thr Ser Phe Gly Gly Tyr Glu Lys Ala
                325                 330                 335

Ser Tyr Leu Thr Asp Ala Tyr Ser Asp Ser Gly Tyr Glu Arg Ser Pro
            340                 345                 350

Ser Pro Phe Ser Asn Ile Ser Ser Pro Leu Cys Ser Glu Gly Ser Trp
        355                 360                 365

Asp Asp Met Phe Ala Ser Glu Leu Phe Pro Gln Leu Ile Ser Val
    370                 375                 380

<210> SEQ ID NO 13
<211> LENGTH: 373
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (7)..(7)
<223> OTHER INFORMATION: A or S
<220> FEATURE:
<221> NAME/KEY: MISC_FEATURE
<222> LOCATION: (9)..(9)
<223> OTHER INFORMATION: S or N
<220> FEATURE:
<221> NAME/KEY: MISC_FEATURE
<222> LOCATION: (10)..(10)
<223> OTHER INFORMATION: A or P
<220> FEATURE:
<221> NAME/KEY: MISC_FEATURE
<222> LOCATION: (12)..(12)
<223> OTHER INFORMATION: T or D
<220> FEATURE:
<221> NAME/KEY: MISC_FEATURE
<222> LOCATION: (13)..(13)
```

-continued

```
<223> OTHER INFORMATION: A or G
<220> FEATURE:
<221> NAME/KEY: MISC_FEATURE
<222> LOCATION: (14)..(14)
<223> OTHER INFORMATION: A or T
<220> FEATURE:
<221> NAME/KEY: MISC_FEATURE
<222> LOCATION: (26)..(26)
<223> OTHER INFORMATION: S or A
<220> FEATURE:
<221> NAME/KEY: MISC_FEATURE
<222> LOCATION: (27)..(27)
<223> OTHER INFORMATION: G, D, or A
<220> FEATURE:
<221> NAME/KEY: MISC_FEATURE
<222> LOCATION: (29)..(29)
<223> OTHER INFORMATION: R or Q
<220> FEATURE:
<221> NAME/KEY: MISC_FEATURE
<222> LOCATION: (37)..(37)
<223> OTHER INFORMATION: G or A
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: MISC_FEATURE
<222> LOCATION: (40)..(40)
<223> OTHER INFORMATION: A or G
<220> FEATURE:
<221> NAME/KEY: MISC_FEATURE
<222> LOCATION: (46)..(48)
<223> OTHER INFORMATION: S, N, or ASG (two amino acids may be missing)
<220> FEATURE:
<221> NAME/KEY: MISC_FEATURE
<222> LOCATION: (50)..(50)
<223> OTHER INFORMATION: T, A, or L
<220> FEATURE:
<221> NAME/KEY: MISC_FEATURE
<222> LOCATION: (105)..(105)
<223> OTHER INFORMATION: H or Q
<220> FEATURE:
<221> NAME/KEY: MISC_FEATURE
<222> LOCATION: (108)..(108)
<223> OTHER INFORMATION: Q or L
<220> FEATURE:
<221> NAME/KEY: MISC_FEATURE
<222> LOCATION: (123)..(123)
<223> OTHER INFORMATION: V or I
<220> FEATURE:
<221> NAME/KEY: MISC_FEATURE
<222> LOCATION: (130)..(130)
<223> OTHER INFORMATION: T or Q
<220> FEATURE:
<221> NAME/KEY: MISC_FEATURE
<222> LOCATION: (136)..(136)
<223> OTHER INFORMATION: T, V, or A
<220> FEATURE:
<221> NAME/KEY: MISC_FEATURE
<222> LOCATION: (138)..(138)
<223> OTHER INFORMATION: D, T, or V
<220> FEATURE:
<221> NAME/KEY: MISC_FEATURE
<222> LOCATION: (139)..(139)
<223> OTHER INFORMATION: P, T, or A
<220> FEATURE:
<221> NAME/KEY: MISC_FEATURE
<222> LOCATION: (140)..(140)
<223> OTHER INFORMATION: D or E
<220> FEATURE:
<221> NAME/KEY: MISC_FEATURE
<222> LOCATION: (142)..(142)
<223> OTHER INFORMATION: V, A, or none
<220> FEATURE:
<221> NAME/KEY: MISC_FEATURE
<222> LOCATION: (143)..(143)
<223> OTHER INFORMATION: P or none
<220> FEATURE:
<221> NAME/KEY: MISC_FEATURE
```

```
<222> LOCATION: (145)..(145)
<223> OTHER INFORMATION: V, T, or A
<220> FEATURE:
<221> NAME/KEY: MISC_FEATURE
<222> LOCATION: (147)..(147)
<223> OTHER INFORMATION: A or S
<220> FEATURE:
<221> NAME/KEY: MISC_FEATURE
<222> LOCATION: (150)..(150)
<223> OTHER INFORMATION: S or N
<220> FEATURE:
<221> NAME/KEY: MISC_FEATURE
<222> LOCATION: (151)..(151)
<223> OTHER INFORMATION: G or E
<220> FEATURE:
<221> NAME/KEY: MISC_FEATURE
<222> LOCATION: (154)..(154)
<223> OTHER INFORMATION: L or P
<220> FEATURE:
<221> NAME/KEY: MISC_FEATURE
<222> LOCATION: (171)..(171)
<223> OTHER INFORMATION: S or P
<220> FEATURE:
<221> NAME/KEY: MISC_FEATURE
<222> LOCATION: (180)..(180)
<223> OTHER INFORMATION: D or G
<220> FEATURE:
<221> NAME/KEY: MISC_FEATURE
<222> LOCATION: (181)..(181)
<223> OTHER INFORMATION: T or G
<220> FEATURE:
<221> NAME/KEY: MISC_FEATURE
<222> LOCATION: (182)..(182)
<223> OTHER INFORMATION: V or I
<220> FEATURE:
<221> NAME/KEY: MISC_FEATURE
<222> LOCATION: (183)..(183)
<223> OTHER INFORMATION: A or D
<220> FEATURE:
<221> NAME/KEY: MISC_FEATURE
<222> LOCATION: (198)..(198)
<223> OTHER INFORMATION: K or N
<220> FEATURE:
<221> NAME/KEY: MISC_FEATURE
<222> LOCATION: (212)..(212)
<223> OTHER INFORMATION: S or P
<220> FEATURE:
<221> NAME/KEY: MISC_FEATURE
<222> LOCATION: (214)..(214)
<223> OTHER INFORMATION: S or N
<220> FEATURE:
<221> NAME/KEY: MISC_FEATURE
<222> LOCATION: (224)..(224)
<223> OTHER INFORMATION: E or none
<220> FEATURE:
<221> NAME/KEY: MISC_FEATURE
<222> LOCATION: (256)..(256)
<223> OTHER INFORMATION: V or I
<220> FEATURE:
<221> NAME/KEY: MISC_FEATURE
<222> LOCATION: (273)..(273)
<223> OTHER INFORMATION: T or A
<220> FEATURE:
<221> NAME/KEY: MISC_FEATURE
<222> LOCATION: (286)..(286)
<223> OTHER INFORMATION: S or P
<220> FEATURE:
<221> NAME/KEY: MISC_FEATURE
<222> LOCATION: (289)..(289)
<223> OTHER INFORMATION: E or N
<220> FEATURE:
<221> NAME/KEY: MISC_FEATURE
<222> LOCATION: (300)..(300)
<223> OTHER INFORMATION: K or E
<220> FEATURE:
<221> NAME/KEY: MISC_FEATURE
<222> LOCATION: (303)..(303)
<223> OTHER INFORMATION: L, V, or none
<220> FEATURE:
```

```
<221> NAME/KEY: MISC_FEATURE
<222> LOCATION: (305)..(305)
<223> OTHER INFORMATION: D or E
<220> FEATURE:
<221> NAME/KEY: MISC_FEATURE
<222> LOCATION: (307)..(307)
<223> OTHER INFORMATION: F or L
<220> FEATURE:
<221> NAME/KEY: MISC_FEATURE
<222> LOCATION: (308)..(308)
<223> OTHER INFORMATION: I or V
<220> FEATURE:
<221> NAME/KEY: MISC_FEATURE
<222> LOCATION: (311)..(311)
<223> OTHER INFORMATION: L or P
<220> FEATURE:
<221> NAME/KEY: MISC_FEATURE
<222> LOCATION: (323)..(323)
<223> OTHER INFORMATION: L or P
<220> FEATURE:
<221> NAME/KEY: MISC_FEATURE
<222> LOCATION: (324)..(324)
<223> OTHER INFORMATION: R or K
<220> FEATURE:
<221> NAME/KEY: MISC_FEATURE
<222> LOCATION: (326)..(326)
<223> OTHER INFORMATION: P or S
<220> FEATURE:
<221> NAME/KEY: MISC_FEATURE
<222> LOCATION: (333)..(333)
<223> OTHER INFORMATION: H or Y
<220> FEATURE:
<221> NAME/KEY: MISC_FEATURE
<222> LOCATION: (339)..(339)
<223> OTHER INFORMATION: E or G
<220> FEATURE:
<221> NAME/KEY: MISC_FEATURE
<222> LOCATION: (342)..(342)
<223> OTHER INFORMATION: P or L
<220> FEATURE:
<221> NAME/KEY: MISC_FEATURE
<222> LOCATION: (351)..(351)
<223> OTHER INFORMATION: P or L
<220> FEATURE:
<221> NAME/KEY: MISC_FEATURE
<222> LOCATION: (354)..(354)
<223> OTHER INFORMATION: T, I, or V
<220> FEATURE:
<221> NAME/KEY: MISC_FEATURE
<222> LOCATION: (355)..(355)
<223> OTHER INFORMATION: D or N

<400> SEQUENCE: 13

Met Val Val Val Ala Ala Pro Xaa Xaa Ala Xaa Xaa Xaa Pro Lys
1               5                   10                  15

Val Leu Leu Leu Ser Gly Gln Pro Ala Xaa Xaa Gly Xaa Ala Leu Pro
            20                  25                  30

Leu Met Val Pro Xaa Xaa Arg Xaa Ala Gly Ser Glu Ala Xaa Xaa Xaa
        35                  40                  45

Gly Xaa Pro Gln Ala Arg Lys Arg Gln Arg Leu Thr His Leu Ser Pro
    50                  55                  60

Glu Glu Lys Ala Leu Arg Arg Lys Leu Lys Asn Arg Val Ala Ala Gln
65                  70                  75                  80

Thr Ala Arg Asp Arg Lys Lys Ala Arg Met Ser Glu Leu Glu Gln Gln
                85                  90                  95

Val Val Asp Leu Glu Glu Glu Asn Xaa Lys Leu Xaa Leu Glu Asn Gln
            100                 105                 110

Leu Leu Arg Glu Lys Thr His Gly Leu Val Xaa Glu Asn Gln Glu Leu
        115                 120                 125

Arg Xaa Arg Leu Gly Met Asp Xaa Leu Xaa Xaa Xaa Glu Xaa Xaa Glu
```

```
        130                 135                 140
Xaa Glu Xaa Lys Gly Xaa Xaa Val Arg Xaa Val Ala Gly Ser Ala Glu
145                 150                 155                 160

Ser Ala Ala Gly Ala Gly Pro Val Val Thr Xaa Pro Glu His Leu Pro
                165                 170                 175

Met Asp Ser Xaa Xaa Xaa Ser Ser Asp Ser Glu Ser Asp Ile Leu
            180                 185                 190

Leu Gly Ile Leu Asp Xaa Leu Asp Pro Val Met Phe Phe Lys Cys Pro
            195                 200                 205

Ser Pro Glu Xaa Ala Xaa Leu Glu Glu Leu Pro Glu Val Tyr Pro Xaa
            210                 215                 220

Gly Pro Ser Ser Leu Pro Ala Ser Leu Ser Leu Ser Val Gly Thr Ser
225                 230                 235                 240

Ser Ala Lys Leu Glu Ala Ile Asn Glu Leu Ile Arg Phe Asp His Xaa
                245                 250                 255

Tyr Thr Lys Pro Leu Val Leu Glu Ile Pro Ser Glu Thr Glu Ser Gln
            260                 265                 270

Xaa Asn Val Val Lys Ile Glu Glu Ala Pro Leu Ser Xaa Ser Glu
            275                 280                 285

Xaa Asp His Pro Glu Phe Ile Val Ser Val Lys Xaa Glu Pro Xaa Glu
            290                 295                 300

Xaa Asp Xaa Xaa Pro Glu Xaa Gly Ile Ser Asn Leu Leu Ser Ser Ser
305                 310                 315                 320

His Cys Xaa Xaa Pro Xaa Ser Cys Leu Leu Asp Ala Xaa Ser Asp Cys
                325                 330                 335

Gly Tyr Xaa Gly Ser Xaa Ser Pro Phe Ser Asp Met Ser Ser Xaa Leu
            340                 345                 350

Gly Xaa Xaa His Ser Trp Glu Asp Thr Phe Ala Asn Gly Leu Phe Pro
            355                 360                 365

Gln Leu Ile Ser Val
    370

<210> SEQ ID NO 14
<211> LENGTH: 7686
<212> TYPE: DNA
<213> ORGANISM: Artificial
<220> FEATURE:
<223> OTHER INFORMATION: Synthetic plasmid

<400> SEQUENCE: 14
aagcttatac tcgagctcta gattgggaac ccgggtctct cgaattcgat gccttttaga      60
ctcctgatac cattgggtct tgtttgcgtt ctcctccctc tccatcacgg cgccccaggt     120
ccagacggta ccgcacctga tcctgcccat taccgcgaac gcgttaaagc catgttctac     180
cacgcctatg actcctatct ggaaaatgca ttccccctatg atgagctccg acccttacc     240 tgcgatggtc atgatacttg gggctctttt tcccttaccc ttattgacgc tctggacaca     300
ctccttatcc tcggaaacac cagcgaattt caaagagtag ttgaagtact tcaggacaat     360
gtcgactttg acatcgatgt gaacgcatca gttttcgaaa caaatataag agtcgttgga     420
ggtctgctct ccgcccacct tctctctaaa aaagccggag tagaagttga agctggctgg     480
ccctgctccg gacccctcct tcgtatggct gaagaagctg cccgcaaact ccttcccgct     540
tttcagaccc caaccggtat gccctatggt actgttaacc tcctgcacgg agtaaatccc     600
ggcgaaaccc ccgtcacatg tacagccgga attggaacct ttattgtgga atttgcaacc     660
```

```
cttagcagcc tgaccggaga tcctgtattc gaagacgtgg ctcgggttgc cctgatgcga    720
ctgtgggaat ccaggtctga tatcggtctg gtcggtaacc atatagacgt actcactggt    780
aaatggttg cacaagacgc tggaattggg gcaggcgtgg attcttattt tgaatatctc    840
gtaaaagggg ccatactctt gcaggacaaa aaacttatgg ctatgttcct ggaatataac    900
aaagctatta ggaactacac acacttcgat gattggtatt tgtgggtcca aatgtataaa    960
ggaaccgttt ctatgcctgt ctttcagtca ctggaggctt attggcctgg tctgcaatcc    1020
ctgatcggag acattgacaa tgcaatgagg acattcctta attattacac tgtttggaag    1080
cagttcggcg gattgcccga attttacaac attcctcaag gctatacagt tgaaaaaaga    1140
gaaggatatc ccctgcgccc cgagcttatt gaaagcgcta tgtatctgta tcgtgcaaca    1200
ggtgatccaa ccctgcttga actgggacga acgccgtcg aatcaatcga aaaatttca    1260
aaagtggaat gcggctttgc aacaattaaa gatcttagag accacaaact ggataatcgc    1320
atggagtcat tcttttttggc tgagaccgtc aagtatctgt atctgctttt tcatcccaac    1380
aacttcatcc ataataacgg gtccaccttc gattcagtca tgacccctca cggtgaatgc    1440
atactcggag ctggaggcta tattttaac actgaagctc acccaattga cccagctgcc    1500
cttcattgtt gtcgacgtct gaaagaagaa caatgggagg ttgaagattt gatcaaagaa    1560
ttttactcac ttaaacaaag tcgacctaaa cgcgcacaga gaaaaactgt aagatctggt    1620
ccttgggaac ctcagtccgg cccagcaact cttttcatcc ccgccaacca accacgagaa    1680
aaacaaccag cccaacagag aaccccctg tcagctgcc cctctcagcc cttcacttca    1740
aaactcgccc tgcttggaca ggtgtttctg gactcctctt gatttaaaca cgcggccgct    1800
aatcagccat accacatttg tagaggtttt acttgcttta aaaaacctcc cacacctccc    1860
cctgaacctg aaacataaaa tgaatgcaat tgttgttgtt aacttgttta ttgcagctta    1920
taatggttac aaataaagca atagcatcac aaatttcaca aataaagcat tttttttcact    1980
gcattctagt tgtggtttgt ccaaactcat caatgtatct tatcatgtct accggtaggg    2040
cccctctctt catgtgagca aaaggccagc aaaaggccag gaaccgtaaa aaggccgcgt    2100
tgctggcgtt tttccatagg ctccgccccc ctgacgagca tcacaaaaat cgacgctcaa    2160
gtcagaggtg gcgaaacccg acaggactat aaagatacca ggcgtttccc cctggaagct    2220
ccctcgtgcg ctctcctgtt ccgaccctgc cgcttaccgg atacctgtcc gcctttctcc    2280
cttcgggaag cgtggcgctt tctcaatgct cacgctgtag gtatctcagt tcggtgtagg    2340
tcgttcgctc caagctgggc tgtgtgcacg aaccccccgt tcagcccgac cgctgcgcct    2400
tatccggtaa ctatcgtctt gagtccaacc cggtaagaca cgacttatcg ccactggcag    2460
cagccactgg taacaggatt agcagagcga ggtatgtagg cggtgctaca gagttcttga    2520
agtggtggcc taactacggc tacactagaa ggacagtatt tggtatctgc gctctgctga    2580
agccagttac cttcggaaaa agagttggta gctcttgatc cggcaaacaa accaccgctg    2640
gtagcggtgg ttttttttgtt tgcaagcagc agattacgcg cagaaaaaaa ggatctcaag    2700
aagatccttt gatcttttct acggggtctg acgctcagtg gaacgaaaac tcacgttaag    2760
ggatttggt catgggcgcg cctcatactc ctgcaggcat gagattatca aaaggatct    2820
tcacctagat ccttttaaat taaaaatgaa gttttaaatc aatctaaagt atatatgagt    2880
aaacttggtc tgacagttac caatgcttaa tcagtgaggc acctatctca gcgatctgtc    2940
tatttcgttc atccatagtt gcctgactcc ccgtcgtgta gataactacg atacgggagg    3000
gcttaccatc tggccccagt gctgcaatga taccgcgaga cccacgctca ccggctccag    3060
```

```
atttatcagc aataaaccag ccagccggaa gggccgagcg cagaagtggt cctgcaactt     3120
tatccgcctc catccagtct attaattgtt gccgggaagc tagagtaagt agttcgccag     3180
ttaatagttt gcgcaacgtt gttgccattg ctacaggcat cgtggtgtca cgctcgtcgt     3240
ttggtatggc ttcattcagc tccggttccc aacgatcaag gcgagttaca tgatccccca     3300
tgttgtgcaa aaaagcggtt agctccttcg gtcctccgat cgttgtcaga agtaagttgg     3360
ccgcagtgtt atcactcatg gttatggcag cactgcataa ttctcttact gtcatgccat     3420
ccgtaagatg cttttctgtg actggtgagt actcaaccaa gtcattctga aatagtgta     3480
tgcggcgacc gagttgctct tgcccggcgt caatacggga taataccgcg ccacatagca     3540
gaactttaaa agtgctcatc attggaaaac gttcttcggg gcgaaaactc tcaaggatct     3600
taccgctgtt gagatccagt tcgatgtaac ccactcgtgc acccaactga tcttcagcat     3660
cttttacttt caccagcgtt tctgggtgag caaaaacagg aaggcaaaat gccgcaaaaa     3720
agggaataag ggcgacacgg aaatgttgaa tactcatact cttcctttt caatattatt     3780
gaagcattta tcagggttat tgtctcatga gcggatacat atttgaatgt atttagaaaa     3840
ataaacaaat agggggttccg cgcacatttc cccgaaaagt gccacctgac gtcaggtacc     3900
aagcctaggc ctccaaaaaa gcctcctcac tacttctgga atagctcaga ggcagaggcg     3960
gcctcggcct ctgcataaat aaaaaaaatt agtcagccat ggggcggaga atgggcggaa     4020
ctgggcggag ttaggggcgg gatgggcgga gttaggggcg ggactatggt tgctgactaa     4080
ttgagatgca tgcttttgcat acttctgcct gctggggagc ctggggactt tccacacctg     4140
gttgctgact aattgagatg catgctttgc atacttctgc ctgctgggga gcctggggac     4200
tttccacacc ggatccacca tgggatcggc cattgaacaa gatggattgc acgcaggttc     4260
tccggccgct tgggtggaga ggctattcgg ctatgactgg gcacaacaga caatcggctg     4320
ctctgatgcc gccgtgttcc ggctgtcagc gcagggcgc ccggttctt tgtcaagac      4380
cgacctgtcc ggtgccctga tgaactgca ggacgaggca gcgcggctat cgtggctggc     4440
cacgacgggc gttccttgcg cagctgtgct cgacgttgtc actgaagcgg gaagggactg     4500
gctgctattg ggcgaagtgc cggggcagga tctcctgtca tctcaccttg ctcctgccga     4560
gaaagtatcc atcatggctg atgcaatgcg gcggctgcat acgcttgatc cggctacctg     4620
cccattcgac caccaagcga aacatcgcat cgagcgagca cgtactcgga tggaagccgg     4680
tcttgtcgat caggatgatc tggacgaaga gcatcagggg ctcgcgccag ccgaactgtt     4740
cgccaggctc aaggcgcgca tgcccgacgg cgatgatctc gtcgtgaccc atggcgatgc     4800
ctgcttgccg aatatcatgg tggaaaatgg ccgcttttct ggattcatcg actgtggccg     4860
gctgggtgtg gcggaccgct atcaggacat agcgttggct acccgtgata ttgctgaaga     4920
gcttggcggc gaatgggctg accgcttcct cgtgctttac ggtatcgccg ctcccgattc     4980
gcagcgcatc gccttctatc gccttcttga cgagttcttc tgaacgcgtg ctgtaagtct     5040
gcagaaattg atgatctatt aaacaataaa gatgtccact aaaatggaag ttttttcctgt    5100
catactttgt taagaagggt gagaacagag tacctacatt ttgaatggaa ggattggagc     5160
tacgggggtg ggggtgggt gggattagat aaatgcctgc tctttactga aggctcttta     5220
ctattgcttt atgataatgt ttcatagttg gatatcataa tttaaacaag caaaaccaaa     5280
ttaagggcca gctcattcct cccactcatg atctatggat ctatagatct ctcgtgcagc     5340
tggggctcta gggggtatcc ccacgcgccc tgtagcggcg cattaagcgc ggcgggtgtg     5400
```

```
gtggttacgc gcagcgtgac cgctacactt gccagcgccc tagcgcccgc tcctttcgct    5460
ttcttccctt cctttctcgc cacgttcgcc ggctttcccc gtcaagctct aaatcggggg    5520
ctcccttag ggttccgatt tagtgcttta cggcacctcg accccaaaaa acttgattag    5580
ggtgatggtt cacgtagtgg gccatcgccc tgatagacgg ttttcgccc tttgacgttg    5640
gagtccacgt tctttaatag tggactcttg ttccaaactg gaacaacact caaccctatc    5700
tcggtctatt cttttgattt ataagggatt ttgccgattt cggcctattg gttaaaaaat    5760
gagctgattt aacaaaaatt taacgcgaat taattctgtg gaatgtgtgt cagttagtcg    5820
cgaggcctcc gcgccgggtt ttggcgcctc ccgcgggcgc cccctcctc acggcgagcg    5880
ctgccacgtc agacgaaggg cgcagcgagc gtcctgatcc ttccgcccgg acgctcagga    5940
cagcggcccg ctgctcataa gactcggcct tagaacccca gtatcagcag aaggacattt    6000
taggacggga cttgggtgac tctagggcac tggttttctt tccagagagc ggaacaggcg    6060
aggaaaagta gtcccttctc ggcgattctg cggaggggatc tccgtggggc ggtgaacgcc    6120
gatgattata taaggacgcg ccgggtgtgg cacagctagt tccgtcgcag ccggatttg    6180
ggtcgcggtt cttgttttgtg gatcgctgtg atcgtcactt ggtgagtagc gggctgctgg    6240
gctggccggg gctttcgtgg ccgccgggcc gctcggtggg acggaagcgt gtggagagac    6300
cgccaagggc tgtagtctgg gtccgcgagc aaggttgccc tgaactgggg gttgggggga    6360
gcgcagcaaa atggcggctg ttcccgagtc ttgaatggaa gacgcttgtg aggcgggctg    6420
tgaggtcgtt gaaacaaggt gggggggcatg gtgggcggca agaacccaag gtcttgaggc    6480
cttcgctaat gcgggaaagc tcttattcgg gtgagatggg ctgggcacc atctggggac    6540
cctgacgtga agtttgtcac tgactggaga actcggtttg tcgtctgttg cgggggcggc    6600
agttatggcg gtgccgttgg gcagtgcacc cgtacctttg ggagcgcgcg ccctcgtcgt    6660
gtcgtgacgt caccgttct gttggcttat aatgcagggt ggggccacct gccggtaggt    6720
gtgcggtagg ctttctccg tcgcaggacg caggggtcgg gcctagggta ggctctcctg    6780
aatcgacagg cgccggacct ctggtgaggg gagggataag tgaggcgtca gtttctttgg    6840
tcggttttat gtacctatct tcttaagtag ctgaagctcc ggttttgaac tatgcgctcg    6900
gggttggcga gtgtgttttg tgaagttttt taggcaccct ttgaaatgta atcatttggg    6960
tcaatatgta atttcagtg ttagactagt aaattgtccg ctaaattctg gccgtttttg    7020
gcttttttgt tagacgtcga ccgatcctga gaacttcagg gtgagtttgg ggacccttga    7080
ttgttctttc tttttcgcta ttgtaaaatt catgttatat ggaggggca aagttttcag    7140
ggtgttgttt agaatgggaa gatgtcccct gtatcaccat ggaccctcat gataattttg    7200
tttctttcac tttctactct gttgacaacc attgtctcct cttatttct tttcatttc    7260
tgtaactttt tcgttaaact ttagcttgca tttgtaacga attttaaat tcacttttgt    7320
ttatttgtca gattgtaagt actttctcta atcacttttt tttcaaggca atcagggtat    7380
attatattgt acttcagcac agttttagag aacaattgtt ataattaaat gataaggtag    7440
aatatttctg catataaatt ctggctggcg tggaaatatt cttattggta gaaacaacta    7500
caccctggtc atcatcctgc cttttctttt atggttacaa tgatatacac tgtttgagat    7560
gaggataaaa tactctgagt ccaaaccggg cccctctgct aaccatgttc atgccttctt    7620
ctcttttccta cagctcctgg gcaacgtgct ggttgttgtg ctgtctcatc attttggcaa    7680
agaatt                                                                7686
```

<210> SEQ ID NO 15
<211> LENGTH: 7257
<212> TYPE: DNA
<213> ORGANISM: Artificial
<220> FEATURE:
<223> OTHER INFORMATION: Synthetic plasmid

<400> SEQUENCE: 15

| | | | | | |
|---|---|---|---|---|---|
| aagcttatac | tcgagctcta | gattgggaac | ccgggtctct | cgaattcgat | gccttttaga | 60 |
| ctcctgatac | cattgggtct | tgtttgcgtt | ctcctccctc | tccatcacgg | cgccccaggt | 120 |
| ccagacggta | ccgcacctga | tcctgcccat | taccgcgaac | gcgttaaagc | catgttctac | 180 |
| cacgcctatg | actcctatct | ggaaaatgca | ttccccatg | atgagctccg | acccttacc | 240 |
| tgcgatggtc | atgatacttg | gggctctttt | tcccttaccc | ttattgacgc | tctggacaca | 300 |
| ctccttatcc | tcggaaacac | cagcgaattt | caaagagtag | ttgaagtact | tcaggacaat | 360 |
| gtcgactttg | acatcgatgt | gaacgcatca | gttttcgaaa | caaatataag | agtcgttgga | 420 |
| ggtctgctct | ccgcccacct | tctctctaaa | aagccggag | tagaagttga | agctggctgg | 480 |
| ccctgctccg | gacccctcct | tcgtatggct | gaagaagctg | cccgcaaact | ccttcccgct | 540 |
| tttcagaccc | caaccggtat | gccctatggt | actgttaacc | tcctgcacgg | agtaaatccc | 600 |
| ggcgaaaccc | ccgtcacatg | tacagccgga | attggaacct | ttattgtgga | atttgcaacc | 660 |
| cttagcagcc | tgaccggaga | tcctgtattc | gaagacgtgg | ctcgggttgc | cctgatgcga | 720 |
| ctgtgggaat | ccaggtctga | tatcggtctg | gtcggtaacc | atatagacgt | actcactggt | 780 |
| aaatggttg | cacaagacgc | tggaattggg | gcaggcgtgg | attcttattt | tgaatatctc | 840 |
| gtaaaagggg | ccatactctt | gcaggacaaa | aaacttatgg | ctatgttcct | ggaatataac | 900 |
| aaagctatta | ggaactacac | acacttcgat | gattggtatt | tgtgggtcca | aatgtataaa | 960 |
| ggaaccgttt | ctatgcctgt | ctttcagtca | ctggaggctt | attggcctgg | tctgcaatcc | 1020 |
| ctgatcggag | acattgacaa | tgcaatgagg | acattcctta | attattacac | tgtttggaag | 1080 |
| cagttcggcg | gattgcccga | attttacaac | attcctcaag | gctatacagt | tgaaaaaga | 1140 |
| gaaggatatc | ccctgcgccc | cgagcttatt | gaaagcgcta | tgtatctgta | tcgtgcaaca | 1200 |
| ggtgatccaa | ccctgcttga | actgggacga | gacgccgtcg | aatcaatcga | gaaaatttca | 1260 |
| aaagtggaat | gcggctttgc | aacaattaaa | gatcttagag | accacaaact | ggataatcgc | 1320 |
| atggagtcat | tctttttggc | tgagaccgtc | aagtatctgt | atctgctttt | tcatcccaac | 1380 |
| aacttcatcc | ataataacgg | gtccaccttc | gattcagtca | tgaccctca | cggtgaatgc | 1440 |
| atactcggag | ctggaggcta | tatttttaac | actgaagctc | acccaattga | cccagctgcc | 1500 |
| cttcattgtt | gtcgacgtct | gaaagaagaa | caatgggagg | ttgaagattt | gatcaaagaa | 1560 |
| ttttactcac | ttaaacaaag | tcgacctaaa | cgcgcacaga | gaaaaactgt | aagatctggt | 1620 |
| ccttgggaac | tcagtccgg | cccagcaact | cttttcatcc | ccgccaacca | accacgagaa | 1680 |
| aaacaaccag | cccaacagag | aaccccctg | ctcagctgcc | cctctcagcc | cttcacttca | 1740 |
| aaactcgccc | tgcttggaca | ggtgtttctg | gactcctctt | gatttaaaca | cgcggccgct | 1800 |
| aatcagccat | accacatttg | tagaggtttt | acttgcttta | aaaaacctcc | cacacctccc | 1860 |
| cctgaacctg | aaacataaaa | tgaatgcaat | tgttgttgtt | aacttgttta | ttgcagctta | 1920 |
| taatggttac | aaataaagca | atagcatcac | aaatttcaca | aataaagcat | tttttcact | 1980 |
| gcattctagt | tgtggtttgt | ccaaactcat | caatgtatct | tatcatgtct | accggtaggg | 2040 |
| ccctctctt | catgtgagca | aaaggccagc | aaaaggccag | gaaccgtaaa | aaggccgcgt | 2100 |

```
tgctggcgtt tttccatagg ctccgccccc ctgacgagca tcacaaaaat cgacgctcaa    2160
gtcagaggtg gcgaaacccg acaggactat aaagatacca ggcgtttccc cctggaagct    2220
ccctcgtgcg ctctcctgtt ccgaccctgc cgcttaccgg atacctgtcc gcctttctcc    2280
cttcgggaag cgtggcgctt tctcatagct cacgctgtag gtatctcagt tcggtgtagg    2340
tcgttcgctc caagctgggc tgtgtgcacg aaccccccgt tcagcccgac cgctgcgcct    2400
tatccggtaa ctatcgtctt gagtccaacc cggtaagaca cgacttatcg ccactggcag    2460
cagccactgg taacaggatt agcagagcga ggtatgtagg cggtgctaca gagttcttga    2520
agtggtggcc taactacggc tacactagaa ggacagtatt tggtatctgc gctctgctga    2580
agccagttac cttcggaaaa agagttggta gctcttgatc cggcaaacaa accaccgctg    2640
gtagcggtgg ttttttttgtt tgcaagcagc agattacgcg cagaaaaaaa ggatctcaag    2700
aagatccttt gatcttttct acgggtctg acgctcagtg aacgaaaac tcacgttaag    2760 ggatttggt catgggcgcg cctcatactc ctgcaggcat gagattatca aaaggatct    2820 tcacctagat cctttaaat taaaaatgaa gttttaaatc aatctaaagt atatatgagt    2880
aaacttggtc tgacagttac caatgcttaa tcagtgaggc acctatctca gcgatctgtc    2940
tatttcgttc atccatagtt gcctgactcc ccgtcgtgta gataactacg atacgggagg    3000
gcttaccatc tggccccagt gctgcaatga taccgcgaga cccacgctca ccggctccag    3060
atttatcagc aataaaccag ccagccggaa gggccgagcg cagaagtggt cctgcaactt    3120
tatccgcctc catccagtct attaattgtt gccgggaagc tagagtaagt agttcgccag    3180
ttaatagttt gcgcaacgtt gttgccattg ctacaggcat cgtggtgtca cgctcgtcgt    3240
ttggtatggc ttcattcagc tccggttccc aacgatcaag gcgagttaca tgatccccca    3300
tgttgtgcaa aaaagcggtt agctccttcg gtcctccgat cgttgtcaga agtaagttgg    3360
ccgcagtgtt atcactcatg gttatggcag cactgcataa ttctcttact gtcatgccat    3420
ccgtaagatg cttttctgtg actggtgagt actcaaccaa gtcattctga aatagtgta    3480 tgcggcgacc gagttgctct tgcccggcgt caatacggga taataccgcg ccacatagca    3540
gaactttaaa agtgctcatc attggaaaac gttcttcggg gcgaaaactc tcaaggatct    3600
taccgctgtt gagatccagt tcgatgtaac ccactcgtgc acccaactga tcttcagcat    3660
cttttacttt caccagcgtt tctgggtgag caaaaacagg aaggcaaaat gccgcaaaaa    3720
agggaataag ggcgacacgg aaatgttgaa tactcatact cttcctttt caatattatt    3780 gaagcattta tcagggttat tgtctcatga gcggatacat atttgaatgt atttagaaaa    3840
ataaacaaat aggggttccg cgcacatttc cccgaaaagt gccacctgac gtcaggtacc    3900
aagcctaggc ctccaaaaaa gcctcctcac tacttctgga atagctcaga ggcagaggcg    3960
gcctcggcct ctgcataaat aaaaaaaatt agtcagccat ggggcggaga atgggcggaa    4020
ctgggcggag ttaggggcgg gatgggcgga gttaggggcg ggactatggt tgctgactaa    4080
ttgagatgca tgctttgcat acttctgcct gctggggagc ctggggactt ccacacctg    4140 gttgctgact aattgagatg catgctttgc atacttctgc ctgctgggga gcctggggac    4200
tttccacacc ggatccacca tggccaagtt gaccagtgcc gttccggtgc tcaccgcgcg    4260
cgacgtcgcc ggagcggtcg agttctggac cgaccggctc gggttctccc gggacttcgt    4320
ggaggacgac ttcgccggtg tggtccggga cgacgtgacc ctgttcatca gcgcggtcca    4380
ggaccaggtg gtgccggaca cacccctggc ctgggtgtgg gtgcgcggcc tggacgagct    4440
gtacgccgag tggtcggagg tcgtgtccac gaacttccgg gacgcctccg ggccggccat    4500
```

```
gaccgagatc ggcgagcagc cgtgggggcg ggagttcgcc ctgcgcgacc cggccggcaa    4560
ctgcgtgcac ttcgtggccg aggagcagga ctgaacgcgt gctgtaagtc tgcagaaatt    4620
gatgatctat aaacaataa agatgtccac taaaatggaa gttttcctg tcatactttg     4680 ttaagaaggg tgagaacaga gtacctacat tttgaatgga aggattggag ctacgggggt    4740
gggggtgggg tgggattaga taaatgcctg ctctttactg aaggctcttt actattgctt    4800
tatgataatg tttcatagtt ggatatcata atttaaacaa gcaaaaccaa attaagggcc    4860
agctcattcc tcccactcat gatctatgga tctatagatc tctcgtgcag ctggggctct    4920
agggggtatc cccacgcgcc ctgtagcggc gcattaagcg cggcgggtgt ggtggttacg    4980
cgcagcgtga ccgctacact tgccagcgcc ctagcgcccg ctcctttcgc tttcttccct    5040
tcctttctcg ccacgttcgc cggctttccc cgtcaagctc taaatcgggg ctcccttta    5100 gggttccgat ttagtgcttt acggcacctc gaccccaaaa aacttgatta gggtgatggt    5160
tcacgtagtg ggccatcgcc ctgatagacg gtttttcgcc ctttgacgtt ggagtccacg    5220
ttctttaata gtggactctt gttccaaact ggaacaacac tcaaccctat ctcggtctat    5280
tcttttgatt tataagggat tttgccgatt tcggcctatt ggttaaaaaa tgagctgatt    5340
taacaaaaat ttaacgcgaa ttaattctgt ggaatgtgtg tcagttagtc gcgaggcctc    5400
cgcgccgggt tttggcgcct cccgcgggcg ccccctcct cacggcgagc gctgccacgt     5460
cagacgaagg gcgcagcgag cgtcctgatc cttccgcccg gacgctcagg acagcggccc    5520
gctgctcata agactcggcc ttagaacccc agtatcagca gaaggacatt ttaggacggg    5580
acttgggtga ctctagggca ctggttttct ttccagagag cggaacaggc gaggaaaagt    5640
agtcccttct cggcgattct gcggagggat ctccgtgggg cggtgaacgc cgatgattat    5700
ataaggacgc gccgggtgtg gcacagctag ttccgtcgca gccgggatt gggtcgcggt     5760 tcttgtttgt ggatcgctgt gatcgtcact tggtgagtag cgggctgctg ggctggccgg    5820
ggctttcgtg gccgccgggc cgctcggtgg gacggaagcg tgtggagaga ccgccaaggg    5880
ctgtagtctg ggtccgcgag caaggttgcc ctgaactggg ggttgggggg agcgcagcaa    5940
aatggcggct gttcccgagt cttgaatgga agacgcttgt gaggcgggct gtgaggtcgt    6000
tgaaacaagg tgggggcat ggtgggcggc aagaacccaa ggtcttgagg ccttcgctaa    6060
tgcgggaaag ctcttattcg ggtgagatgg gctgggcac catctgggga ccctgacgtg     6120
aagtttgtca ctgactggag aactcggttt gtcgtctgtt gcggggggcgg cagttatggc    6180 ggtgccgttg ggcagtgcac ccgtaccttt gggagcgcgc gccctcgtcg tgtcgtgacg    6240
tcacccgttc tgttggctta taatgcaggg tggggccacc tgccggtagg tgtgcggtag    6300
gcttttctcc gtcgcaggac gcaggggtcg ggcctaggggt aggctctcct gaatcgacag    6360
gcgccggacc tctggtgagg ggagggataa gtgaggcgtc agtttctttg gtcggtttta    6420
tgtacctatc ttcttaagta gctgaagctc cggttttgaa ctatgcgctc ggggttggcg    6480
agtgtgtttt gtgaagtttt ttaggcacct tttgaaatgt aatcatttgg gtcaatatgt    6540
aattttcagt gttagactag taaattgtcc gctaaattct ggccgttttt ggcttttttg    6600
ttagacgtcg accgatcctg agaacttcag ggtgagtttg ggacccttg attgttcttt     6660 cttttttcgct attgtaaaat tcatgttata tggaggggc aaagttttca gggtgttgtt    6720
tagaatggga agatgtccct tgtatcacca tggaccctca tgataatttt gtttctttca    6780
ctttctactc tgttgacaac cattgtctcc tcttattttc tttcattttt ctgtaacttt    6840
```

```
ttcgttaaac tttagcttgc atttgtaacg aattttaaa ttcactttg tttatttgtc    6900 agattgtaag tactttctct aatcactttt ttttcaaggc aatcagggta tattatattg    6960
tacttcagca cagttttaga gaacaattgt tataattaaa tgataaggta gaatatttct    7020
gcatataaat tctggctggc gtggaaatat tcttattggt agaaacaact acaccctggt    7080
catcatcctg cctttctctt tatggttaca atgatataca ctgtttgaga tgaggataaa    7140
atactctgag tccaaaccgg gcccctctgc taaccatgtt catgccttct tctctttcct    7200
acagctcctg ggcaacgtgc tggttgttgt gctgtctcat catttggca aagaatt       7257
```

<210> SEQ ID NO 16
<211> LENGTH: 3892
<212> TYPE: DNA
<213> ORGANISM: Artificial
<220> FEATURE:
<223> OTHER INFORMATION: Synthetic construct

<400> SEQUENCE: 16

```
aggcctccgc gccgggtttt ggcgcctccc gcgggcgccc ccctcctcac ggcgagcgct      60
gccacgtcag acgaagggcg cagcgagcgt cctgatcctt ccgcccggac gctcaggaca     120
gcggcccgct gctcataaga ctcggcctta aacccccagt atcagcagaa ggacatttta     180
ggacgggact tgggtgactc tagggcactg gttttctttc cagagagcgg aacaggcgag     240
gaaaagtagt cccttctcgg cgattctgcg gagggatctc cgtggggcgg tgaacgccga     300
tgattatata aggacgcgcc gggtgtggca cagctagttc cgtcgcagcc gggatttggg     360
tcgcggttct tgtttgtgga tcgctgtgat cgtcacttgg tgagtagcgg gctgctgggc     420
tggccggggc tttcgtggcc gccgggccgc tcggtgggac ggaagcgtgt ggagagaccg     480
ccaagggctg tagtctgggt ccgcgagcaa ggttgccctg aactgggggt tgggggagc      540 gcagcaaaat ggcggctgtt cccgagtctt gaatggaaga cgcttgtgag gcgggctgtg     600
aggtcgttga acaaggtgg ggggcatggt gggcggcaag aacccaaggt cttgaggcct      660
tcgctaatgc gggaaagctc ttattcgggt gagatgggct ggggcaccat ctggggaccc    720
tgacgtgaag tttgtcactg actgagaaac tcggtttgtc gtctgttgcg ggggcggcag    780
ttatggcggt gccgttgggc agtgcacccg tacctttggg agcgcgcgcc ctcgtcgtgt    840
cgtgacgtca cccgttctgt tggcttataa tgcagggtgg ggccacctgc cggtaggtgt    900
gcggtaggct tttctccgtc gcaggacgca gggttcgggc ctagggtagg ctctcctgaa    960
tcgacaggcg ccggacctct ggtgagggga gggataagtg aggcgtcagt ttctttggtc   1020
ggttttatgt acctatcttc ttaagtagct gaagctccgg ttttgaacta tgcgctcggg   1080
gttggcgagt gtgttttgtg aagtttttta ggcaccttt gaaatgtaat catttgggtc   1140
aatatgtaat tttcagtgtt agactagtaa attgtccgct aaattctggc cgttttggc    1200 tttttgtta gacgtcgacc gatcctgaga acttcagggt gagtttgggg acccttgatt   1260
gttctttctt tttcgctatt gtaaaattca tgttatatgg aggggcaaa gttttcaggg    1320 tgttgtttag aatgggaaga tgtcccttgt atcaccatgg accctcatga taattttgtt   1380
tctttcactt tctactctgt tgacaaccat tgtctcctct tatttctttt tcattttctg    1440
taactttttc gttaaacttt agcttgcatt tgtaacgaat ttttaaattc acttttgttt    1500
atttgtcaga ttgtaagtac tttctctaat cactttttt tcaaggcaat cagggtatat    1560
tatattgtac ttcagcacag ttttagagaa caattgttat aattaaatga taaggtagaa    1620
tatttctgca tataaattct ggctggcgtg gaaatattct tattggtaga aacaactaca    1680
```

```
cctggtcat catcctgcct ttctctttat ggttacaatg atatacactg tttgagatga    1740
ggataaaata ctctgagtcc aaaccgggcc cctctgctaa ccatgttcat gccttcttct    1800
ctttcctaca gctcctgggc aacgtgctgg ttgttgtgct gtctcatcat tttggcaaag    1860
aattaagctt atactcgagc tctagattgg gaacccgggt ctctcgaatt cgatgccttt    1920
tagactcctg ataccattgg gtcttgtttg cgttctcctc cctctccatc acggcgcccc    1980
aggtccagac ggtaccgcac ctgatcctgc ccattaccgc gaacgcgtta aagccatgtt    2040
ctaccacgcc tatgactcct atctggaaaa tgcattcccc tatgatgagc tccgacccct    2100
tacctgcgat ggtcatgata cttggggctc ttttccctt acccttattg acgctctgga     2160
cacactcctt atcctcggaa acaccagcga atttcaaaga gtagttgaag tacttcagga    2220
caatgtcgac tttgacatcg atgtgaacgc atcagttttc gaaacaaata taagagtcgt    2280
tggaggtctg ctctccgccc accttctctc taaaaaagcc ggagtagaag ttgaagctgg    2340 ctggcccctgc tccggacccc tccttcgtat ggctgaagaa gctgcccgca aactccttcc    2400
cgcttttcag accccaaccg gtatgcccta tggtactgtt aacctcctgc acggagtaaa    2460
tcccggcgaa accccgtca catgtacagc cggaattgga acctttattg tggaatttgc     2520
aacccttagc agcctgaccg gagatcctgt attcgaagac gtggctcggg ttgccctgat    2580
gcgactgtgg gaatccaggt ctgatatcgg tctggtcggt aaccatatag acgtactcac    2640
tggtaaatgg gttgcacaag acgctggaat tggggcaggc gtggattctt attttgaata    2700
tctcgtaaaa ggggccatac tcttgcagga caaaaaactt atggctatgt tcctggaata    2760
taacaaagct attaggaact acacacactt cgatgattgg tatttgtggg tccaaatgta    2820
taaaggaacc gtttctatgc ctgtctttca gtcactggag gcttattggc ctggtctgca    2880
atccctgatc ggagacattg acaatgcaat gaggacattc cttaattatt acactgtttg    2940
gaagcagttc ggcggattgc ccgaatttta caacattcct caaggctata cagttgaaaa    3000
aagagaagga tatcccctgc gccccgagct tattgaaagc gctatgtatc tgtatcgtgc    3060
aacaggtgat ccaaccctgc ttgaactggg acgagacgcc gtcgaatcaa tcgagaaaat    3120
ttcaaaagtg gaatgcggct tgcaacaat taaagatctt agagaccaca aactggataa      3180
tcgcatggag tcattctttt tggctgagac cgtcaagtat ctgtatctgc ttttcatcc     3240 caacaacttc atccataata acgggtccac cttcgattca gtcatgaccc ctcacggtga    3300
atgcatactc ggagctggag gctatatttt taacactgaa gctcacccaa ttgacccagc    3360
tgcccttcat tgttgtcgac gtctgaaaga agaacaatgg gaggttgaag atttgatcaa    3420 agaatttac tcacttaaac aaagtcgacc taaacgcgca cagagaaaaa ctgtaagatc      3480
tggtccttgg gaacctcagt ccggcccagc aactctttca tcccccgcca accaaccacg    3540
agaaaaacaa ccagcccaac agagaacccc cctgctcagc tgcccctctc agcccttcac    3600
ttcaaaactc gccctgcttg acaggtgtt tctggactcc tcttgattta aacacgcggc      3660
cgctaatcag ccataccaca tttgtagagg ttttacttgc tttaaaaaac ctcccacacc    3720
tccccctgaa cctgaaacat aaaatgaatg caattgttgt tgttaacttg tttattgcag    3780
cttataatgg ttacaaataa agcaaatagca tcacaaattt cacaaataaa gcatttttt    3840 cactgcattc tagttgtggt ttgtccaaac tcatcaatgt atcttatcat gt             3892
```

<210> SEQ ID NO 17
<211> LENGTH: 6629
<212> TYPE: DNA

<213> ORGANISM: Artificial
<220> FEATURE:
<223> OTHER INFORMATION: Synthetic plasmid

<400> SEQUENCE: 17

```
aagcttatac tcgagctcta gattgggaac ccgggtctct cgaattcatg gtggtggtgg      60
ctgctgctcc ttctgctgct acagctgctc ctaaggtgct gctgctgtct ggacagcctg     120
cttctggagg aagagctctg cctctgatgg tgcctggacc tagagctgct ggatctgagg     180
cttctggaac acctcaggct agaaagagac agagactgac acatctgtct cctgaagaaa     240
aggctctgag aagaaagctg aagaatagag tggctgctca gacagctaga gatagaaaga     300
aggctagaat gtctgaactg gaacagcagg tggtggatct ggaagaagaa aatcataagc     360
tgcagctgga aaatcagctg ctgagagaaa agacacatgg actggtggtg aaaaatcagg     420
aactgagaac aagactggga atggatacac tggatcctga tgaagtgcct gaagtggaag     480
ctaagggatc tggagtgaga ctggtggctg atctgctgac atctgctgct ggagctggac     540
ctgtggtgac atctcctgaa catctgccta tggattctga tacagtggct tcttctgatt     600
ctgaatctga tatcctgctg ggaatcctgg ataagctgga tcctgtgatg tttttttaagt     660
gtccttctcc tgaatctgct tctctggaag aactgcctga agtgtatcct gaaggacctt     720
cttctctgcc tgcttctctg tctctgtctg tgggaacatc ttctgctaag ctggaagcta     780
tcaatgaact gatcagattt gatcatgtgt atacaaagcc tctggtgctg aaaatccctt     840
ctgaaacaga atctcagaca atgtggtgg tgaagatcga agaagctcct ctgtcttctt     900
ctgaagaaga tcatcctgaa tttatcgtgt ctgtgaagaa ggaacctctg aagatgatt     960
ttatccctga actgggaatc tctaatctgc tgtcttcttc tcattgtctg agacctcctt    1020
cttgtctgct ggatgctcat tctgattgtg gatatgaagg atctccttct ccttttttctg    1080
atatgtcttc tcctctggga acagatcatt cttgggaaga tacatttgct aatgaactgt    1140
ttcctcagct gatctctgtg tgagcggccg ctaatcagcc ataccacatt tgtagaggtt    1200
ttacttgctt taaaaaacct cccacacctc cccctgaacc tgaaacataa aatgaatgca    1260
attgttgttg ttaacttgtt tattgcagct tataatggtt acaaataaag caatagcatc    1320
acaaatttca caaataaagc atttttttca ctgcattcta gttgtggttt gtccaaactc    1380
atcaatgtat cttatcatgt ctaccggtag ggccctctc ttcatgtgag caaaaggcca    1440
gcaaaaggcc aggaaccgta aaaaggccgc gttgctggcg ttttttccata ggctccgccc    1500
ccctgacgag catcacaaaa atcgacgctc aagtcagagg tggcgaaacc cgacaggact    1560
ataaagatac caggcgtttc ccctggaag ctccctcgtg cgctctcctg ttccgaccct    1620
gccgcttacc ggatacctgt ccgcctttct cccttcggga agcgtggcgc tttctcatag    1680
ctcacgctgt aggtatctca gttcggtgta ggtcgttcgc tccaagctgg gctgtgtgca    1740
cgaaccccc gttcagcccg accgctgcgc cttatccggt aactatcgtc ttgagtccaa    1800
cccggtaaga cacgacttat cgccactggc agcagccact ggtaacagga ttagcagagc    1860
gaggtatgta ggcggtgcta cagagttctt gaagtggtgg cctaactacg gctacactag    1920
aaggacagta tttggtatct gcgctctgct gaagccagtt accttcggaa aaagagttgg    1980
tagctcttga tccggcaaac aaaccaccgc tggtagcggt ggtttttttg tttgcaagca    2040
gcagattacg cgcagaaaaa aaggatctca agaagatcct ttgatctttt ctacggggtc    2100
tgacgctcag tggaacgaaa actcacgtta agggattttg gtcatgggcg cgcctcatac    2160
tcctgcaggc atgagattat caaaaaggat cttcacctag atccttttaa attaaaaatg    2220
```

```
aagttttaaa tcaatctaaa gtatatatga gtaaacttgg tctgacagtt accaatgctt    2280
aatcagtgag gcacctatct cagcgatctg tctatttcgt tcatccatag ttgcctgact    2340
ccccgtcgtg tagataacta cgatacggga gggcttacca tctggcccca gtgctgcaat    2400
gataccgcga gacccacgct caccggctcc agatttatca gcaataaacc agccagccgg    2460
aagggccgag cgcagaagtg gtcctgcaac tttatccgcc tccatccagt ctattaattg    2520
ttgccgggaa gctagagtaa gtagttcgcc agttaatagt ttgcgcaacg ttgttgccat    2580
tgctacaggc atcgtggtgt cacgctcgtc gtttggtatg gcttcattca gctccggttc    2640
ccaacgatca aggcgagtta catgatcccc catgttgtgc aaaaaagcgg ttagctcctt    2700
cggtcctccg atcgttgtca gaagtaagtt ggccgcagtg ttatcactca tggttatggc    2760
agcactgcat aattctctta ctgtcatgcc atccgtaaga tgcttttctg tgactggtga    2820
gtactcaacc aagtcattct gagaatagtg tatgcggcga ccgagttgct cttgcccggc    2880
gtcaatacgg gataataccg cgccacatag cagaacttta aaagtgctca tcattggaaa    2940
acgttcttcg gggcgaaaac tctcaaggat cttaccgctg ttgagatcca gttcgatgta    3000
acccactcgt gcacccaact gatcttcagc atcttttact ttcaccagcg tttctgggtg    3060
agcaaaaaca ggaaggcaaa atgccgcaaa aaagggaata agggcgacac ggaaatgttg    3120
aatactcata ctcttccttt ttcaatatta ttgaagcatt tatcagggtt attgtctcat    3180
gagcggatac atatttgaat gtatttagaa aaataaacaa ataggggttc cgcgcacatt    3240
tccccgaaaa gtgccacctg acgtcaggta ccaagcctag gcctccaaaa aagcctcctc    3300
actacttctg gaatagctca gaggcagagg cggcctcggc ctctgcataa ataaaaaaaa    3360
ttagtcagcc atggggcgga gaatgggcgg aactgggcgg agttaggggc gggatgggcg    3420
gagttagggg cgggactatg gttgctgact aattgagatg catgctttgc atacttctgc    3480
ctgctgggga gcctggggac tttccacacc tggttgctga ctaattgaga tgcatgcttt    3540
gcatacttct gcctgctggg gagcctgggg actttccaca ccggatccac catggccaag    3600
ttgaccagtg ccgttccggt gctcaccgcg cgcgacgtcg ccggagcggt cgagttctgg    3660
accgaccggc tcgggttctc ccgggacttc gtggaggacg acttcgccgg tgtggtccgg    3720
gacgacgtga ccctgttcat cagcgcggtc caggaccagg tggtgccgga caacaccctg    3780
gcctgggtgt gggtgcgcgg cctggacgag ctgtacgccg agtggtcgga ggtcgtgtcc    3840
acgaacttcc gggacgcctc cgggccggcc atgaccgaga tcggcgagca gccgtgggggg    3900
cgggagttcg ccctgcgcga cccggccggc aactgcgtgc acttcgtggc cgaggagcag    3960
gactgaacgc gtgctgtaag tctgcagaaa ttgatgatct attaaacaat aaagatgtcc    4020
actaaaatgg aagttttttcc tgtcatactt tgttaagaag ggtgagaaca gagtacctac    4080
attttgaatg gaaggattgg agctacgggg gtgggggtgg ggtgggatta gataaatgcc    4140
tgctctttac tgaaggctct ttactattgc tttatgataa tgtttcatag ttggatatca    4200
taatttaaac aagcaaaacc aaattaaggg ccagctcatt cctcccactc atgatctatg    4260
gatctataga tctctcgtgc agctggggct ctagggggta tccccacgcg ccctgtagcg    4320
gcgcattaag cgcggcgggt gtggtggtta cgcgcagcgt gaccgctaca cttgccagcg    4380
ccctagcgcc cgctcctttc gctttcttcc cttcctttct cgccacgttc gccggctttc    4440
cccgtcaagc tctaaatcgg gggctccctt tagggttccg atttagtgct ttacggcacc    4500
tcgacccaa aaaacttgat tagggtgatg gttcacgtag tgggccatcg ccctgataga    4560
```

```
cggttttttcg cccttttgacg ttggagtcca cgttctttaa tagtggactc ttgttccaaa    4620
ctggaacaac actcaaccct atctcggtct attcttttga tttataaggg attttgccga    4680
tttcggccta ttggttaaaa aatgagctga tttaacaaaa atttaacgcg aattaattct    4740
gtggaatgtg tgtcagttag tcgcgaggcc tccgcgccgg ttttggcgc ctcccgcggg    4800
cgccccctc ctcacggcga gcgctgccac gtcagacgaa gggcgcagcg agcgtcctga    4860
tccttccgcc cggacgctca ggacagcggc ccgctgctca taagactcgg ccttagaacc    4920
ccagtatcag cagaaggaca ttttaggacg ggacttgggt gactctaggg cactggtttt    4980
cttttccagag agcggaacag gcgaggaaaa gtagtccctt ctcggcgatt ctgcggaggg    5040
atctccgtgg ggcggtgaac gccgatgatt atataaggac gcgccgggtg tggcacagct    5100
agttccgtcg cagccgggat ttgggtcgcg gttcttgttt gtggatcgct gtgatcgtca    5160
cttggtgagt agcgggctgc tgggctgcc ggggctttcg tggccgccgg gccgctcggt    5220
gggacggaag cgtgtggaga gaccgccaag ggctgtagtc tgggtccgcg agcaaggttg    5280
ccctgaactg ggggttgggg ggagcgcagc aaaatggcgg ctgttcccga gtcttgaatg    5340
gaagacgctt gtgaggcggg ctgtgaggtc gttgaaacaa ggtgggggc atggtgggcg    5400
gcaagaaccc aaggtcttga ggccttcgct aatgcggaaa agctcttatt cgggtgagat    5460
gggctggggc accatctggg gaccctgacg tgaagtttgt cactgactgg agaactcggt    5520
ttgtcgtctg ttgcggggc ggcagttatg gcggtgccgt tgggcagtgc acccgtacct    5580
ttgggagcgc gcgccctcgt cgtgtcgtga cgtcacccgt tctgttggct tataatgcag    5640
ggtggggcca cctgccggta ggtgtgcggt aggcttttct ccgtcgcagg acgcagggtt    5700
cgggcctagg gtaggctctc ctgaatcgac aggcgccgga cctctggtga ggggagggat    5760
aagtgaggcg tcagtttctt tggtcggttt tatgtaccta tcttcttaag tagctgaagc    5820
tccggttttg aactatgcgc tcggggttgg cgagtgtgtt ttgtgaagtt ttttaggcac    5880
cttttgaaat gtaatcattt gggtcaatat gtaattttca gtgttagact agtaaattgt    5940
ccgctaaatt ctggccgttt ttggcttttt tgttagacgt cgaccgatcc tgagaacttc    6000
agggtgagtt tggggaccct tgattgttct ttcttttttcg ctattgtaaa attcatgtta    6060
tatggagggg gcaaagtttt cagggtgttg tttagaatgg gaagatgtcc cttgtatcac    6120
catgacccct catgataatt ttgtttcttt cactttctac tctgttgaca accattgtct    6180
cctcttattt tccttttcatt ttctgtaact ttttcgttaa actttagctt gcatttgtaa    6240
cgaattttta aattcacttt tgtttatttg tcagattgta agtactttct ctaatcactt    6300
tttttttcaag gcaatcaggg tatattatat tgtacttcag cacagtttta gagaacaatt    6360
gttataatta aatgataagg tagaatattt ctgcatataa attctggctg gcgtggaaat    6420
attcttattg gtagaaacaa ctacaccctg gtcatcatcc tgcctttctc tttatggtta    6480
caatgatata cactgtttga gatgaggata aaatactctg agtccaaacc gggcccctct    6540
gctaaccatg ttcatgcctt cttctctttc ctacagctcc tgggcaacgt gctggttgtt    6600
gtgctgtctc atcattttgg caaagaatt                                       6629
```

<210> SEQ ID NO 18
<211> LENGTH: 3264
<212> TYPE: DNA
<213> ORGANISM: Artificial
<220> FEATURE:
<223> OTHER INFORMATION: Synthetic construct

<400> SEQUENCE: 18

```
ggcctccgcg ccgggttttg gcgcctcccg cgggcgcccc cctcctcacg gcgagcgctg    60
ccacgtcaga cgaagggcgc agcgagcgtc ctgatccttc cgcccggacg ctcaggacag   120
cggcccgctg ctcataagac tcggccttag aaccccagta tcagcagaag gacattttag   180
gacgggactt gggtgactct agggcactgg ttttctttcc agagagcgga acaggcgagg   240
aaaagtagtc ccttctcggc gattctgcgg agggatctcc gtgggcggt gaacgccgat   300 gattatataa ggacgcgccg ggtgtggcac agctagttcc gtcgcagccg ggatttgggt   360
cgcggttctt gtttgtggat cgctgtgatc gtcacttggt gagtagcggg ctgctgggct   420
ggccggggct ttcgtggccg ccgggccgct cggtgggacg gaagcgtgtg gagagaccgc   480
caagggctgt agtctgggtc cgcgagcaag gttgccctga actgggggtt gggggagcg   540 cagcaaaatg gcggctgttc ccgagtcttg aatggaagac gcttgtgagg cgggctgtga   600
ggtcgttgaa acaaggtggg gggcatggtg ggcggcaaga acccaaggtc ttgaggcctt   660
cgctaatgcg ggaaagctct tattcgggtg agatgggctg gggcaccatc tggggaccct   720
gacgtgaagt ttgtcactga ctggagaact cggtttgtcg tctgttgcgg gggcggcagt   780
tatggcggtg ccgttgggca gtgcacccgt acctttggga gcgcgcgccc tcgtcgtgtc   840
gtgacgtcac ccgttctgtt ggcttataat gcagggtggg gccacctgcc ggtaggtgtg   900
cggtaggctt ttctccgtcg caggacgcag ggttcgggcc tagggtaggc tctcctgaat   960
cgacaggcgc cggacctctg gtgaggggag ggataagtga ggcgtcagtt tctttggtcg  1020
gttttatgta cctatcttct taagtagctg aagctccggt tttgaactat gcgctcgggg  1080
ttggcgagtg tgttttgtga agttttttag gcacctttg aaatgtaatc atttgggtca  1140
atatgtaatt ttcagtgtta gactagtaaa ttgtccgcta aattctggcc gttttttggct  1200 tttttgttag acgtcgaccg atcctgagaa cttcagggtg agtttgggga cccttgattg  1260
ttctttcttt ttcgctattg taaaattcat gttatatgga gggggcaaag ttttcagggt  1320
gttgtttaga atgggaagat gtcccttgta tcaccatgga ccctcatgat aattttgttt  1380
ctttcacttt ctactctgtt gacaaccatt gtctcctctt attttctttt cattttctgt  1440 aacttttcg ttaaacttta gcttgcattt gtaacgaatt tttaaattca cttttgttta  1500
tttgtcagat tgtaagtact ttctctaatc actttttttt caaggcaatc agggtatatt  1560
atattgtact tcagcacagt tttagagaac aattgttata attaaatgat aaggtagaat  1620
atttctgcat ataaattctg gctggcgtgg aaatattctt attggtagaa acaactacac  1680
cctggtcatc atcctgcctt tctctttatg gttacaatga tatacactgt ttgagatgag  1740
gataaaatac tctgagtcca aaccgggccc ctctgctaac catgttcatg ccttcttctc  1800
tttcctacag ctcctgggca acgtgctggt tgttgtgctg tctcatcatt ttggcaaaga  1860
attaagctta tactcgagct ctagattggg aacccgggtc tctcgaattc atggtggtgg  1920
tggctgctgc tccttctgct gctacagctg ctcctaaggt gctgctgctg tctggacagc  1980
ctgcttctgg aggaagagct ctgcctctga tggtgcctgg acctagagct gctggatctg  2040
aggcttctgg aacacctcag gctagaaaga gacagagact gacacatctg tctcctgaag  2100
aaaaggctct gagaagaaag ctgaagaata gagtggctgc tcagacagct agagatagaa  2160
agaaggctag aatgtctgaa ctggaacagc aggtggtgga tctggaagaa gaaaatcata  2220
agctgcagct ggaaaatcag ctgctgagag aaaagacaca tggactggtg gtggaaaatc  2280
aggaactgag aacaagactg ggaatggata cactggatcc tgatgaagtg cctgaagtgg  2340
```

```
aagctaaggg atctggagtg agactggtgg ctggatctgc tgaatctgct gctggagctg    2400
gacctgtggt gacatctcct gaacatctgc ctatggattc tgatacagtg gcttcttctg    2460
attctgaatc tgatatcctg ctgggaatcc tggataagct ggatcctgtg atgtttttta    2520
agtgtccttc tcctgaatct gcttctctgg aagaactgcc tgaagtgtat cctgaaggac    2580
cttcttctct gcctgcttct ctgtctctgt ctgtgggaac atcttctgct aagctggaag    2640
ctatcaatga actgatcaga tttgatcatg tgtatacaaa gcctctggtg ctggaaatcc    2700
cttctgaaac agaatctcag acaaatgtgg tggtgaagat cgaagaagct cctctgtctt    2760
cttctgaaga agatcatcct gaatttatcg tgtctgtgaa gaaggaacct ctggaagatg    2820
attttatccc tgaactggga atctctaatc tgctgtcttc ttctcattgt ctgagacctc    2880
cttcttgtct gctggatgct cattctgatt gtggatatga aggatctcct tctcctttt    2940 ctgatatgtc ttctcctctg ggaacagatc attcttggga agatacattt gctaatgaac    3000
tgtttcctca gctgatctct gtgtgagcgg ccgctaatca gccataccac atttgtagag    3060
gttttacttg ctttaaaaaa cctcccacac ctcccccctga acctgaaaca taaaatgaat    3120
gcaattgttg ttgttaactt gtttattgca gcttataatg gttacaaata aagcaatagc    3180
atcacaaatt tcacaaataa agcatttttt tcactgcatt ctagttgtgg tttgtccaaa    3240
ctcatcaatg tatcttatca tgtc                                          3264
```

<210> SEQ ID NO 19
<211> LENGTH: 447
<212> TYPE: PRT
<213> ORGANISM: Homo sapiens

<400> SEQUENCE: 19

Glu Val Gln Val Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Trp Lys Met Ser Gly Leu Asp Val Trp Gly Gln
            100                 105                 110

Gly Thr Thr Val Ile Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

```
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225             230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 20
<211> LENGTH: 110
<212> TYPE: PRT
<213> ORGANISM: Homo sapiens

<400> SEQUENCE: 20

Glu Ser Gly Gly Asp Leu Val Gln Pro Gly Gly Ser Leu Arg Leu Ser
1               5                   10                  15

Cys Ala Ala Ser Gly Phe Thr Phe Ser Ala Tyr Ala Met Thr Trp Val
                20                  25                  30

Arg Gln Ala Pro Gly Lys Gly Leu Glu Trp Val Ser Ala Ile Ser Gly
            35                  40                  45

Ser Gly Gly Ser Ala Tyr Tyr Ala Asp Ser Val Lys Gly Arg Phe Thr
        50                  55                  60

Ile Ser Arg Asp Asn Ser Lys Asn Thr Val Tyr Leu Gln Met Asn Ser
65                  70                  75                  80

Leu Arg Ala Glu Asp Thr Ala Val Tyr Tyr Cys Ala Lys Asp Gly Ala
                85                  90                  95

Trp Lys Ser Gly Leu Asp Val Trp Gly Gln Gly Thr Thr
                100                 105                 110

<210> SEQ ID NO 21
<211> LENGTH: 214
<212> TYPE: PRT
<213> ORGANISM: Homo sapiens
```

<400> SEQUENCE: 21

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 22
<211> LENGTH: 100
<212> TYPE: PRT
<213> ORGANISM: Homo sapiens

<400> SEQUENCE: 22

Gln Ser Pro Ala Ser Leu Ser Ala Ser Val Gly Asp Arg Val Thr Ile
1               5                   10                  15

Thr Cys Arg Ala Ser Gln Asp Ile Ser Asp Tyr Leu Ala Trp Tyr Gln
            20                  25                  30

Gln Lys Pro Gly Lys Ile Pro Arg Leu Leu Ile Tyr Thr Thr Ser Thr
        35                  40                  45

Leu Gln Ser Gly Val Pro Ser Arg Phe Arg Gly Ser Gly Ser Gly Thr
50                  55                  60

Asp Phe Thr Leu Thr Ile Ser Ser Leu Gln Pro Glu Asp Val Ala Thr
65                  70                  75                  80

Tyr Tyr Cys Gln Lys Tyr Asp Ser Ala Pro Leu Thr Phe Gly Gly Gly
                85                  90                  95

Thr Lys Val Glu
            100

<210> SEQ ID NO 23
<211> LENGTH: 2971
<212> TYPE: DNA
<213> ORGANISM: Artificial
<220> FEATURE:
<223> OTHER INFORMATION: Synthetic construct

<400> SEQUENCE: 23

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctca tgatagaagc actctactat cgtcgaccg      600
atcctgagaa cttcagggtg agtttgggga cccttgattg ttctttcttt ttcgctattg     660
taaaattcat gttatatgga gggggcaaag ttttcagggt gttgtttaga atgggaagat     720
gtcccttgta tcaccatgga ccctcatgat aattttgttt ctttcacttt ctactctgtt     780
gacaaccatt gtctcctctt attttctttt catttctgt aacttttttcg ttaaactta      840
gcttgcattt gtaacgaatt tttaaattca cttttgttta tttgtcagat tgtaagtact     900
ttctctaatc actttttttt caaggcaatc agggtatatt atattgtact tcagcacagt     960
tttagagaac aattgttata attaaatgat aaggtagaat atttctgcat ataaattctg    1020
gctggcgtgg aaatattctt attggtagaa acaactacac cctggtcatc atcctgcctt    1080
tctctttatg gttacaatga tatacactgt ttgagatgag gataaaatac tctgagtcca    1140
aaccgggccc ctctgctaac catgttcatg ccttcttctc tttcctacag ctcctgggca    1200
acgtgctggt tgttgtgctg tctcatcatt ttggcaaaga attaagctta tactcgagct    1260
ctagattggg aacccgggtc tctcgaattc gagatctcca ccatgcacag acctagacgt    1320
cgtggaactc gtccacctcc actggcactg ctcgctgctc cctcctggc tgcacgtggt     1380
gctgatgcag aggtgcaggt gttggagtct gggggagact tggtacagcc tggggggtcc    1440
ctgagactct cctgtgcagc ctctggattc acctttagtg cctatgccat gacctgggtc    1500
cgccaggctc cagggaaggg gctggagtgg gtctcagcta ttagtggtag tggtggtagc    1560
gcatactacg cagactccgt gaagggccgg ttcaccatct ccagagacaa ttccaagaac    1620
acggtatatc tgcagatgaa cagcctgaga gccgaggaca cggccgtata ttactgtgcg    1680
aaagatgggg cctggaaaat gtccggtttg gacgtctggg gccaagggac cacggtcatc    1740
gtctcctcag cctccaccaa gggcccatcg gtcttccccc tggcgccctg ctccaggagc    1800
acctccgaga gcacagccgc cctgggctgc ctggtcaagg actacttccc cgaaccggtg    1860
acggtgtcgt ggaactcagg cgccctgacc agcggcgtgc acaccttccc ggctgtccta    1920
cagtcctcag gactctactc cctcagcagc gtggtgaccg tgccctccag cagcttgggc    1980
acgaagacct acacctgcaa cgtagatcac aagcccagca acaccaaggt ggacaagaga    2040
gttgagtcca aatatggtcc cccatgccca cctgcccag cacctgagtt cctgggggga    2100
ccatcagtct tcctgttccc cccaaaaccc aaggacactc tcatgatctc ccggaccctt    2160
gaggtcacgt gcgtggtggt ggacgtgagc caggaagacc ccgaggtcca gttcaactgg    2220
```

| | |
|---|---|
| tacgtggatg gcgtggaggt gcataatgcc aagacaaagc cgcgggagga gcagttcaac | 2280 |
| agcacgtacc gtgtggtcag cgtcctcacc gtcctgcacc aggactggct gaacggcaag | 2340 |
| gagtacaagt gcaaggtctc caacaaaggc ctcccgtcct ccatcgagaa aaccatctcc | 2400 |
| aaagccaaag ggcagccccg agagccacag gtgtacaccc tgcccccatc ccaggaggag | 2460 |
| atgaccaaga accaggtcag cctgacctgc ctggtcaaag gcttctaccc cagcgacatc | 2520 |
| gccgtggagt gggagagcaa tgggcagccg gagaacaact acaagaccac gcctcccgtg | 2580 |
| ctggactccg acggctcctt cttcctctac agcaggctca ccgtggacaa gagcaggtgg | 2640 |
| caggagggga atgtcttctc atgctccgtg atgcatgagg ctctgcacaa ccactacaca | 2700 |
| cagaagtccc tctccctgtc tctgggtaaa tgagcggccg ctaatcagcc ataccacatt | 2760 |
| tgtagaggtt ttacttgctt taaaaaacct cccacacctc cccctgaacc tgaaacataa | 2820 |
| aatgaatgca attgttgttg ttaacttgtt tattgcagct tataatggtt acaaataaag | 2880 |
| caatagcatc acaaatttca caaataaagc atttttttca ctgcattcta gttgtggttt | 2940 |
| gtccaaactc atcaatgtat cttatcatgt c | 2971 |

<210> SEQ ID NO 24
<211> LENGTH: 7013
<212> TYPE: DNA
<213> ORGANISM: Artificial
<220> FEATURE:
<223> OTHER INFORMATION: Synthetic plasmid

<400> SEQUENCE: 24

| | |
|---|---|
| tcgcgatgtg tgactagtta gttattaata gtaatcaatt acggggtcat tagttcatag | 60 |
| cccatatatg gagttccgcg ttacataact tacggtaaat ggcccgcctg gctgaccgcc | 120 |
| caacgacccc cgcccattga cgtcaataat gacgtatgtt cccatagtaa cgccaatagg | 180 |
| gactttccat tgacgtcaat gggtggagta tttacggtaa actgcccact tggcagtaca | 240 |
| tcaagtgtat catatgccaa gtacgccccc tattgacgtc aatgacggta aatggcccgc | 300 |
| ctggcattat gcccagtaca tgaccttatg ggactttcct acttggcagt acatctacgt | 360 |
| attagtcatc gctattacca tggtgatgcg gttttggcag tacatcaatg ggcgtggata | 420 |
| gcggtttgac tcacggggat ttccaagtct ccaccccatt gacgtcaatg ggagtttgtt | 480 |
| ttggcaccaa aatcaacggg actttccaaa atgtcgtaac aactccgccc cattgacgca | 540 |
| aatgggcggt aggcgtgtac ggtgggaggt ctatataagc agagctcatg atagaagcac | 600 |
| tctactattc gtcgaccgat cctgagaact tcagggtgag tttggggacc cttgattgtt | 660 |
| ctttcttttt cgctattgta aaattcatgt tatatggagg gggcaaagtt ttcagggtgt | 720 |
| tgtttagaat gggaagatgt cccttgtatc accatggacc ctcatgataa ttttgtttct | 780 |
| ttcactttct actctgttga caaccattgt ctcctcttat tttcttttca ttttctgtaa | 840 |
| cttttcgtt aaactttagc ttgcatttgt aacgaatttt taaattcact tttgtttatt | 900 |
| tgtcagattg taagtacttt ctctaatcac ttttttttca aggcaatcag ggtatattat | 960 |
| attgtacttc agcacagttt tagagaacaa ttgttataat aaatgataaa ggtagaatat | 1020 |
| ttctgcatat aaattctggc tggcgtggaa atattcttat tggtagaaac aactacaccc | 1080 |
| tggtcatcat cctgcctttc tctttatggt tacaatgata tacactgttt gagatgagga | 1140 |
| taaaatactc tgagtccaaa ccgggcccct ctgctaacca tgttcatgcc ttcttctctt | 1200 |
| tcctacagct cctgggcaac gtgctggttg ttgtgctgtc tcatcatttt ggcaaagaat | 1260 |
| taagcttata ctcgagctct agattgggaa cccgggctctc tcgaattcga gatctccacc | 1320 |

```
atgcacagac ctagacgtcg tggaactcgt ccacctccac tggcactgct cgctgctctc    1380
ctcctggctg cacgtggtgc tgatgcagag gtgcaggtgt tggagtctgg gggagacttg    1440
gtacagcctg gggggtccct gagactctcc tgtgcagcct ctggattcac ctttagtgcc    1500
tatgccatga cctgggtccg ccaggctcca gggaaggggc tggagtgggt ctcagctatt    1560
agtggtagtg gtggtagcgc atactacgca gactccgtga agggccggtt caccatctcc    1620
agagacaatt ccaagaacac ggtatatctg cagatgaaca gcctgagagc cgaggacacg    1680
gccgtatatt actgtgcgaa agatggggcc tggaaaatgt ccggtttgga cgtctgggc    1740
caagggacca cggtcatcgt ctcctcagcc tccaccaagg gcccatcggt cttcccctg    1800
gcgccctgct ccaggagcac ctccgagagc acagccgccc tgggctgcct ggtcaaggac    1860
tacttccccg aaccggtgac ggtgtcgtgg aactcaggcg ccctgaccag cggcgtgcac    1920
accttcccgg ctgtcctaca gtcctcagga ctctactccc tcagcagcgt ggtgaccgtg    1980
ccctccagca gcttgggcac gaagacctac acctgcaacg tagatcacaa gcccagcaac    2040
accaaggtgg acaagagagt tgagtccaaa tatggtcccc catgcccacc ctgcccagca    2100
cctgagttcc tggggggacc atcagtcttc ctgttccccc caaaacccaa ggacactctc    2160
atgatctccc ggacccctga ggtcacgtgc gtggtggtgg acgtgagcca ggaagacccc    2220
gaggtccagt tcaactggta cgtggatggc gtggaggtgc ataatgccaa gacaaagccg    2280
cgggaggagc agttcaacag cacgtaccgt gtggtcagcg tcctcaccgt cctgcaccag    2340
gactggctga acggcaagga gtacaagtgc aaggtctcca acaaaggcct cccgtcctcc    2400
atcgagaaaa ccatctccaa agccaaaggg cagccccgag agccacaggt gtacaccctg    2460
cccccatccc aggaggagat gaccaagaac caggtcagcc tgacctgcct ggtcaaaggc    2520
ttctacccca gcgacatcgc cgtggagtgg gagagcaatg ggcagccgga gaacaactac    2580
aagaccacgc ctcccgtgct ggactccgac ggctccttct tcctctacag caggctcacc    2640
gtggacaaga gcaggtggca ggaggggaat gtcttctcat gctccgtgat gcatgaggct    2700
ctgcacaacc actacacaca gaagtccctc tccctgtctc tgggtaaatg agcggccgct    2760
aatcagccat accacatttg tagaggtttt acttgcttta aaaaacctcc cacacctccc    2820
cctgaacctg aaacataaaa tgaatgcaat tgttgttgtt aacttgttta ttgcagctta    2880
taatggttac aaataaagca atagcatcac aaatttcaca aataaagcat tttttcact    2940
gcattctagt tgtggtttgt ccaaactcat caatgtatct tatcatgtct accggtcctg    3000
cagggcccct ctcttcatgt gagcaaaagg ccagcaaaag ccaggaacc gtaaaaaggc    3060
cgcgttgctg gcgttttcc ataggctccg cccccctgac gagcatcaca aaaatcgacg    3120
ctcaagtcag aggtggcgaa acccgacagg actataaaga taccaggcgt ttccccctgg    3180
aagctccctc gtgcgctctc ctgttccgac cctgccgctt accggatacc tgtccgcctt    3240
tctcccttcg ggaagcgtgg cgctttctca atgctcacgc tgtaggtatc tcagttcggt    3300
gtaggtcgtt cgctccaagc tgggctgtgt gcacgaaccc cccgttcagc ccgaccgctg    3360
cgccttatcc ggtaactatc gtcttgagtc aacccggta agacacgact tatcgccact    3420
ggcagcagcc actggtaaca ggattagcag agcgaggtat gtaggcggtg ctacagagtt    3480
cttgaagtgg tggcctaact acggctacac tagaaggaca gtatttggta tctgcgctct    3540
gctgaagcca gttaccttcg gaaaaagagt tggtagctct tgatccggca aacaaaccac    3600
cgctggtagc ggtggttttt tgtttgcaa gcagcagatt acgcgcagaa aaaaggatc    3660
```

```
tcaagaagat cctttgatct tttctacggg gtctgacgct cagtggaacg aaaactcacg    3720
ttaagggatt ttggtcatgg gcgcgcctca tactcctgca ggcatgagat tatcaaaaag    3780
gatcttcacc tagatccttt taaattaaaa atgaagtttt aaatcaatct aaagtatata    3840
tgagtaaact tggtctgaca gttaccaatg cttaatcagt gaggcaccta tctcagcgat    3900
ctgtctattt cgttcatcca tagttgcctg actccccgtc gtgtagataa ctacgatacg    3960
ggagggctta ccatctggcc ccagtgctgc aatgataccg cgagacccac gctcaccggc    4020
tccagattta tcagcaataa accagccagc cggaagggcc gagcgcagaa gtggtcctgc    4080
aactttatcc gcctccatcc agtctattaa ttgttgccgg gaagctagag taagtagttc    4140
gccagttaat agtttgcgca acgttgttgc cattgctaca ggcatcgtgg tgtcacgctc    4200
gtcgtttggt atggcttcat tcagctccgg ttcccaacga tcaaggcgag ttacatgatc    4260
ccccatgttg tgcaaaaaag cggttagctc cttcggtcct ccgatcgttg tcagaagtaa    4320
gttggccgca gtgttatcac tcatggttat ggcagcactg cataattctc ttactgtcat    4380
gccatccgta agatgctttt ctgtgactgg tgagtactca accaagtcat tctgagaata    4440
gtgtatgcgg cgaccgagtt gctcttgccc ggcgtcaata cgggataata ccgcgccaca    4500
tagcagaact ttaaaagtgc tcatcattgg aaaacgttct cgggggcgaa aactctcaag    4560
gatcttaccg ctgttgagat ccagttcgat gtaacccact cgtgcaccca actgatcttc    4620
agcatctttt actttcacca gcgtttctgg gtgagcaaaa acaggaaggc aaaatgccgc    4680
aaaaaaggga ataagggcga cacggaaatg ttgaatactc atactcttcc ttttcaata    4740
ttattgaagc atttatcagg gttattgtct catgagcgga tacatatttg aatgtattta    4800
gaaaaataaa caaatagggg ttccgcgcac atttccccga aaagtgccac ctgacgtcag    4860
gtaccaagcc taggcctcca aaaaagcctc ctcactactt ctggaatagc tcagaggcag    4920
aggcggcctc ggcctctgca taaataaaaa aaattagtca gccatggggc ggagaatggg    4980
cggaactggg cggagttagg ggcgggatgg gcggagttag gggcgggact atggttgctg    5040
actaattgag atgcatgctt tgcatacttc tgcctgctgg ggagcctggg gactttccac    5100
acctggttgc tgactaattg agatgcatgc tttgcatact tctgcctgct ggggagcctg    5160
gggactttcc acaccggatc caccatggat agatccggaa agcctgaact caccgcgacg    5220
tctgtcgaga gtttctgatc gaaaagttcg acagcgtctc cgacctgat gcagctctcg    5280
gagggcgaag aatctcgtgc tttcagcttc gatgtaggag ggcgtggata tgtcctgcgg    5340
gtaaatagct cgccgatgg tttctacaaa gatcgttatg tttatcggca ctttgcatcg    5400
gccgcgctcc cgattccgga agtgcttgac attggggagt tcagcgagag cctgacctat    5460
tgcatctccc gccgtgcaca gggtgtcacg ttgcaagacc tgcctgaaac cgaactgccc    5520
gctgttctgc agccggtcgc ggaggccatg gatgcgatcg ctgcggccga tcttagccag    5580
acgagcgggt tcggcccatt cggaccgcaa ggaatcggtc aatacactac atggcgtgat    5640
ttcatatgcg cgattgctga tccccatgtg tatcactggc aaactgtgat ggacgacacc    5700
gtcagtgcgt ccgtcgcgca ggctctcgat gagctgatgc tttgggccga ggactgcccc    5760
gaagtccggc acctcgtgca cgcggattc ggctccaaca atgtcctgac ggacaatggc    5820
cgcataacag cggtcattga ctggagcgag gcgatgttcg gggattccca atacgaggtc    5880
gccaacatct tcttctggag gccgtggttg gcttgtatgg agcagcagac gcgctacttc    5940
gagcggaggc atccggagct tgcaggatcg ccgcggctcc gggcgtatat gctccgcatt    6000
ggtcttgacc aactctatca gagcttggtt gacggcaatt tcgatgatgc agcttgggcg    6060
```

```
cagggtcgat gcgacgcaat cgtccgatcc ggagccggga ctgtcgggcg tacacaaatc    6120
gcccgcagaa gcgcggccgt ctggaccgat ggctgtgtag aagtactcgc cgatagtgga    6180
aaccgacgcc ccagcactcg tccgagggca aggaataga cgcgtgctgt aagtctgcag    6240
aaattgatga tctattaaac aataaagatg tccactaaaa tggaagtttt tcctgtcata    6300
ctttgttaag aagggtgaga acagagtacc tacattttga atggaaggat tggagctacg    6360
ggggtggggg tggggtggga ttagataaat gcctgctctt tactgaaggc tctttactat    6420
tgctttatga taatgtttca tagttggata tcataattta aacaagcaaa accaaattaa    6480
gggccagctc attcctccca ctcatgatct atggatctat agatctctcg tgcagctggg    6540
gctctagggg gtatccccac gcgccctgta gcggcgcatt aagcgcggcg ggtgtggtgg    6600
ttacgcgcag cgtgaccgct acacttgcca gcgccctagc gcccgctcct ttcgctttct    6660
tcccttcctt tctcgccacg ttcgccggct ttccccgtca agctctaaat cggggggctcc    6720 ctttagggtt ccgatttagt gctttacggc acctcgaccc caaaaaactt gattagggtg    6780
atggttcacg tagtgggcca tcgccctgat agacggtttt tcgccctttg acgttggagt    6840
ccacgttctt taatagtgga ctcttgttcc aaactggaac aacactcaac cctatctcgg    6900
tctattcttt tgatttataa gggattttgc cgatttcggc ctattggtta aaaaatgagc    6960
tgatttaaca aaaatttaac gcgaattaat tctgtggaat gtgtgtcagt tag           7013
```

<210> SEQ ID NO 25
<211> LENGTH: 2272
<212> TYPE: DNA
<213> ORGANISM: Artificial
<220> FEATURE:
<223> OTHER INFORMATION: Synthetic construct

<400> SEQUENCE: 25

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctca tgatagaagc actctactat tcgtcgaccg     600
atcctgagaa cttcagggtg agtttgggga cccttgattg ttctttcttt ttcgctattg     660
taaaattcat gttatatgga gggggcaaag ttttcagggt gttgtttaga atgggaagat     720
gtcccttgta tcaccatgga ccctcatgat aattttgttt ctttcacttt ctactctgtt     780
gacaaccatt gtctcctctt attttctttt cattttctgt aacttttttcg ttaaactttta     840 gcttgcattt gtaacgaatt tttaaattca cttttgtttat tttgtcagat tgtaagtact     900
ttctctaatc acttttttttt caaggcaatc agggtatatt atattgtact tcagcacagt     960
tttagagaac aattgttata attaaatgat aaggtagaat atttctgcat ataaattctg    1020
gctggcgtgg aaatattctt attggtagaa acaactacac cctggtcatc atcctgcctt    1080
```

```
tctctttatg gttacaatga tatacactgt ttgagatgag gataaaatac tctgagtcca    1140
aaccgggccc ctctgctaac catgttcatg ccttcttctc tttcctacag ctcctgggca    1200
acgtgctggt tgttgtgctg tctcatcatt ttggcaaaga attaagctta tactcgagct    1260
ctagattggg aacccgggtc tctcgaattc gagatctcca ccatgcacag acctagacgt    1320
cgtggaactc gtccacctcc actggcactg ctcgctgctc tcctcctggc tgcacgtggt    1380
gctgatgcag acatccagat gacccagtct ccagcctccc tgtctgcatc tgttggagac    1440
agagtcacca tcacttgtcg ggcgagtcag gacattagcg attatttagc ctggtatcag    1500
cagaaaccag ggaaaattcc taggctcctg atctatacta catccacttt gcaatcaggg    1560
gtcccatctc ggttccgtgg cagtgggtct gggacagatt tcactctcac catcagcagc    1620
ctgcagcctg aagatgttgc aacttattac tgtcagaagt atgacagtgc cccgctcact    1680
ttcggcggag ggaccaaggt ggagatcaaa cgaactgtgg ctgcaccatc tgtcttcatc    1740
ttcccgccat ctgatgagca gttgaaatct ggaactgcct ctgttgtgtg cctgctgaat    1800
aacttctatc ccagagaggc caaagtacag tggaaggtgg ataacgccct ccaatcgggt    1860
aactcccagg agagtgtcac agagcaggac agcaaggaca gcacctacag cctcagcagc    1920
accctgacgc tgagcaaagc agactacgag aaacacaaag tctacgcctg cgaagtcacc    1980
catcagggcc tgagctcgcc cgtcacaaag agcttcaaca ggggagagtg ttaggcggcc    2040
gctaatcagc cataccacat ttgtagaggt tttacttgct ttaaaaaacc tcccacacct    2100
cccccctgaac ctgaaacata aaatgaatgc aattgttgtt gttaacttgt ttattgcagc    2160
ttataatggt tacaaataaa gcaatagcat cacaaatttc acaaataaag cattttttc    2220
actgcattct agttgtggtt tgtccaaact catcaatgta tcttatcatg tc            2272
```

<210> SEQ ID NO 26
<211> LENGTH: 6335
<212> TYPE: DNA
<213> ORGANISM: Artificial
<220> FEATURE:
<223> OTHER INFORMATION: Synthetic plasmid

<400> SEQUENCE: 26

```
tcgagctcta gattgggaac ccgggtctct cgaattcgag atctccacca tgcacagacc     60
tagacgtcgt ggaactcgtc cacctccact ggcactgctc gctgctctcc tcctggctgc    120
acgtggtgct gatgcagaca tccagatgac ccagtctcca gcctccctgt ctgcatctgt    180
tggagacaga gtcaccatca cttgtcgggc gagtcaggac attagcgatt atttagcctg    240
gtatcagcag aaaccaggga aaattcctag gctcctgatc tatactacat ccactttgca    300
atcaggggtc ccatctcggt tccgtggcag tgggtctggg acagatttca ctctcaccat    360
cagcagcctg cagcctgaag atgttgcaac ttattactgt cagaagtatg acagtgcccc    420
gctcactttc ggcggaggga ccaaggtgga gatcaaacga actgtggctg caccatctgt    480
cttcatcttc ccgccatctg atgagcagtt gaaatctgga actgcctctg ttgtgtgcct    540
gctgaataac ttctatccca gagaggccaa agtacagtgg aaggtggata acgccctcca    600
atcgggtaac tccaggaga gtgtcacaga gcaggacagc aaggacagca cctacagcct    660
cagcagcacc ctgacgctga gcaaagcaga ctacgagaaa cacaaagtct acgcctgcga    720
agtcacccat cagggcctga gctcgcccgt cacaaagagc ttcaacaggg gagagtgtta    780
ggcggccgct aatcagccat accacatttg tagaggtttt acttgcttta aaaaacctcc    840
cacacctccc cctgaacctg aaacataaaa tgaatgcaat tgttgttgtt aacttgttta    900
```

| | |
|---|---|
| ttgcagctta taatggttac aaataaagca atagcatcac aaatttcaca aataaagcat | 960 |
| ttttttcact gcattctagt tgtggtttgt ccaaactcat caatgtatct tatcatgtct | 1020 |
| accggtaggg cccctctctt catgtgagca aaaggccagc aaaaggccag gaaccgtaaa | 1080 |
| aaggccgcgt tgctggcgtt tttccatagg ctccgccccc ctgacgagca tcacaaaaat | 1140 |
| cgacgctcaa gtcagaggtg gcgaaacccg acaggactat aaagatacca ggcgtttccc | 1200 |
| cctggaagct ccctcgtgcg ctctcctgtt ccgaccctgc cgcttaccgg atacctgtcc | 1260 |
| gcctttctcc cttcgggaag cgtggcgctt tctcaatgct cacgctgtag gtatctcagt | 1320 |
| tcggtgtagg tcgttcgctc caagctgggc tgtgtgcacg aacccccgt tcagcccgac | 1380 |
| cgctgcgcct tatccggtaa ctatcgtctt gagtccaacc cggtaagaca cgacttatcg | 1440 |
| ccactggcag cagccactgg taacaggatt agcagagcga gtatgtagg cggtgctaca | 1500 |
| gagttcttga agtggtggcc taactacggc tacactagaa ggacagtatt tggtatctgc | 1560 |
| gctctgctga agccagttac cttcggaaaa agagttggta gctcttgatc cggcaaacaa | 1620 |
| accaccgctg gtagcggtgg ttttttttgtt tgcaagcagc agattacgcg cagaaaaaaa | 1680 |
| ggatctcaag aagatccttt gatcttttct acggggtctg acgctcagtg gaacgaaaac | 1740 |
| tcacgttaag ggattttggt catgggcgcg gcatgagat tatcaaaaag gatcttcacc | 1800 |
| tagatccttt taaattaaaa atgaagtttt aaatcaatct aaagtatata tgagtaaact | 1860 |
| tggtctgaca gttaccaatg cttaatcagt gaggcaccta tctcagcgat ctgtctattt | 1920 |
| cgttcatcca tagttgcctg actccccgtc gtgtagataa ctacgatacg ggagggctta | 1980 |
| ccatctggcc ccagtgctgc aatgatcccg cgagacccac gctcaccggc tccagattta | 2040 |
| tcagcaataa accagccagc cggaagggcc gagcgcagaa gtggtcctgc aactttatcc | 2100 |
| gcctccatcc agtctattaa ttgttgccgg gaagctagag taagtagttc gccagttaat | 2160 |
| agtttgcgca acgttgttgc cattgctaca ggcatcgtgg tgtcacgctc gtcgtttggt | 2220 |
| atggcttcat tcagctccgg ttcccaacga tcaaggcgag ttacatgatc ccccatgttg | 2280 |
| tgcaaaaaag cggttagctc cttcggtcct ccgatcgttg tcagaagtaa gttggccgca | 2340 |
| gtgttatcac tcatggttat ggcagcactg cataattctc ttactgtcat gccatccgta | 2400 |
| agatgctttt ctgtgactgg tgagtactca accaagtcat tctgagaata gtgtatgcgg | 2460 |
| cgaccgagtt gctcttgccc ggcgtcaata cgggataata ccgcgccaca tagcagaact | 2520 |
| ttaaaagtgc tcatcattgg aaaacgttct tcggggcgaa aactctcaag gatcttaccg | 2580 |
| ctgttgagat ccagttcgat gtaacccact cgtgcaccca actgatcttc agcatctttt | 2640 |
| actttcacca gcgtttctgg gtgagcaaaa acaggaaggc aaaatgccgc aaaaaaggga | 2700 |
| ataagggcga cacggaaatg ttgaatactc atactcttcc ttttcaata ttattgaagc | 2760 |
| atttatcagg gttattgtct catgagcgga tacatatttg aatgtattta gaaaaataaa | 2820 |
| caaatagggg ttccgcgcac atttccccga aaagtgccac ctgacgtcag gtacacttag | 2880 |
| gcgcgccatt agagttcctg caggctacat ggtaccaagc ctaggcctcc aaaaaagcct | 2940 |
| cctcactact tctggaatag ctcagaggca gaggcggcct cggcctctgc ataaataaaa | 3000 |
| aaaattagtc agccatgggg cggagaatgg gcggaactgg gcggagttag ggcgggatg | 3060 |
| ggcggagtta ggggcgggac tatggttgct gactaattga gatgcatgct ttgcatactt | 3120 |
| ctgcctgctg gggagcctgg ggactttcca cacctggttg ctgactaatt gagatgcatg | 3180 |
| ctttgcatac ttctgcctgc tggggagcct ggggactttc cacaccggat ccaccatgga | 3240 |

```
tagatccgga aagcctgaac tcaccgcgac gtctgtcgag aagtttctga tcgaaaagtt   3300
cgacagcgtc tccgacctga tgcagctctc ggagggcgaa gaatctcgtg ctttcagctt   3360
cgatgtagga gggcgtggat atgtcctgcg ggtaaatagc tgcgccgatg gtttctacaa   3420
agatcgttat gtttatcggc actttgcatc ggccgcgctc ccgattccgg aagtgcttga   3480
cattggggag ttcagcgaga gcctgaccta ttgcatctcc cgccgtgcac agggtgtcac   3540
gttgcaagac ctgcctgaaa ccgaactgcc cgctgttctg cagccggtcg cggaggccat   3600
ggatgcgatc gctgcggccg atcttagcca gacgagcggg ttcggcccat tcggaccgca   3660
aggaatcggt caatacacta catggcgtga tttcatatgc gcgattgctg atccccatgt   3720
gtatcactgg caaactgtga tggacgacac cgtcagtgcg tccgtcgcgc aggctctcga   3780
tgagctgatg ctttgggccg aggactgccc cgaagtccgg cacctcgtgc acgcggattt   3840
cggctccaac aatgtcctga cggacaatgg ccgcataaca gcggtcattg actggagcga   3900
ggcgatgttc ggggattccc aatacgaggt cgccaacatc ttcttctgga ggccgtggtt   3960
ggcttgtatg gagcagcaga cgcgctactt cgagcggagg catccggagc ttgcaggatc   4020
gccgcggctc cgggcgtata tgctccgcat tggtcttgac caactctatc agagcttggt   4080
tgacggcaat ttcgatgatg cagcttgggc gcagggtcga tgcgacgcaa tcgtccgatc   4140
cggagccggg actgtcgggc gtacacaaat cgcccgcaga agcgcggccg tctggaccga   4200
tggctgtgta gaagtactcg ccgatagtgg aaaccgacgc cccagcactc gtccgagggc   4260
aaaggaatag acgcgtgctg taagtctgca gaaattgatg atctattaaa caataaagat   4320
gtccactaaa atggaagttt ttcctgtcat actttgttaa gaagggtgag aacagagtac   4380
ctacattttg aatggaagga ttggagctac gggggtgggg gtggggtggg attagataaa   4440
tgcctgctct ttactgaagg ctctttacta ttgctttatg ataatgtttc atagttggat   4500
atcataattt aaacaagcaa accaaattaa agggccagct cattcctccc actcatgatc   4560
tatgatctat agatctctc gtgcagctgg ggctctaggg ggtatcccca cgcgccctgt   4620
agcggcgcat taagcgcggc gggtgtggtg gttacgcgca gcgtgaccgc tacacttgcc   4680
agcgccctag cgcccgctcc tttcgctttc ttcccttcct ttctcgccac gttcgccggc   4740
tttccccgtc aagctctaaa tcgggggctc cctttagggt tccgatttag tgctttacgg   4800
cacctcgacc ccaaaaaact tgattagggt gatggttcac gtagtgggcc atcgccctga   4860
tagacggttt ttcgcccttt gacgttggag tccacgttct ttaatagtgg actcttgttc   4920
caaactggaa caacactcaa ccctatctcg gtctattctt ttgatttata agggattttg   4980
ccgatttcgg cctattggtt aaaaaatgag ctgatttaac aaaaatttaa cgcgaattaa   5040
ttctgtggaa tgtgtgtcag ttagtcgcga tgtgtgacta gttagttatt aatagtaatc   5100
aattacgggg tcattagttc atagcccata tatggagttc cgcgttacat aacttacggt   5160
aaatggcccg cctggctgac cgcccaacga ccccgcccca ttgacgtcaa taatgacgta   5220
tgttcccata gtaacgccaa tagggacttt ccattgacgt caatgggtgg agtatttacg   5280
gtaaactgcc cacttggcag tacatcaagt gtatcatatg ccaagtacgc cccctattga   5340
cgtcaatgac ggtaaatggc ccgcctggca ttatgcccag tacatgacct tatgggactt   5400
tcctacttgg cagtacatct acgtattagt catcgctatt accatggtga tgcggttttg   5460
gcagtacatc aatgggcgtg gatagcggtt tgactcacgg ggatttccaa gtctccaccc   5520
cattgacgtc aatgggagtt tgttttggca ccaaaatcaa cgggactttc caaaatgtcg   5580
taacaactcc gccccattga cgcaaatggg cggtaggcgt gtacggtggg aggtctatat   5640
```

-continued

```
aagcagagct catgatagaa gcactctact attcgtcgac cgatcctgag aacttcaggg    5700
tgagtttggg gacccttgat tgttctttct ttttcgctat tgtaaaattc atgttatatg    5760
gagggggcaa agttttcagg gtgttgttta gaatgggaag atgtcccttg tatcaccatg    5820
gaccctcatg ataattttgt ttctttcact ttctactctg ttgacaacca ttgtctcctc    5880 ttatttctt tcattttct gtaacttttt cgttaaactt tagcttgcat tgtaacgaa       5940 tttttaaatt cactttgtt tatttgtcag attgtaagta ctttctctaa tcactttttt    6000
ttcaaggcaa tcagggtata ttatattgta cttcagcaca gttttagaga acaattgtta    6060
taattaaatg ataaggtaga atatttctgc atataaattc tggctggcgt ggaaatattc    6120
ttattggtag aaacaactac accctggtca tcatcctgcc tttctcttta tggttacaat    6180
gatatacact gtttgagatg aggataaaat actctgagtc caaaccgggc ccctctgcta    6240
accatgttca tgccttcttc tctttcctac agctcctggg caacgtgctg gttgttgtgc    6300
tgtctcatca ttttggcaaa gaattaagct tatac                               6335
```

<210> SEQ ID NO 27
<211> LENGTH: 452
<212> TYPE: PRT
<213> ORGANISM: Homo sapiens

<400> SEQUENCE: 27

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
```

```
                      245                 250                 255
Met Ile Ser Arg Thr Pro Glu Val Thr Cys Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 28
<211> LENGTH: 112
<212> TYPE: PRT
<213> ORGANISM: Homo sapiens

<400> SEQUENCE: 28

Glu Ser Gly Gly Gly Leu Val Gln Pro Gly Gly Ser Leu Arg Leu Ser
1               5                   10                  15

Cys Ala Ala Ser Gly Phe Thr Phe Ser Ser Tyr Asp Ile His Trp Val
            20                  25                  30

Arg Gln Ala Thr Gly Lys Gly Leu Glu Trp Val Ser Ala Ile Gly Pro
        35                  40                  45

Ala Gly Asp Thr Tyr Tyr Pro Gly Ser Val Lys Gly Arg Phe Thr Ile
    50                  55                  60

Ser Arg Glu Asn Ala Lys Asn Ser Leu Tyr Leu Gln Met Asn Ser Leu
65                  70                  75                  80

Arg Ala Gly Asp Thr Ala Val Tyr Tyr Cys Ala Arg Gly Leu Ile Thr
                85                  90                  95

Phe Gly Gly Leu Ile Ala Pro Phe Asp Tyr Trp Gly Gln Gly Thr Leu
            100                 105                 110

<210> SEQ ID NO 29
<211> LENGTH: 214
<212> TYPE: PRT
<213> ORGANISM: Homo sapiens

<400> SEQUENCE: 29

Glu Ile Val Leu Thr Gln Ser Pro Gly Thr Leu Ser Leu Ser Pro Gly
```

```
                1               5                      10                      15
            Glu Arg Ala Thr Leu Ser Cys Arg Ala Ser Gln Ser Val Ser Ser Thr
                            20                      25                      30

Tyr Leu Ala Trp Tyr Gln Gln Lys Pro Gly Gln Ala Pro Arg Leu Leu
                            35                      40                      45

Ile Tyr Gly Ala Ser Ser Arg Ala Thr Gly Ile Pro Asp Arg Phe Ser
                            50                      55                      60

Gly Ser Gly Ser Gly Thr Asp Phe Thr Leu Thr Ile Ser Arg Leu Glu
             65                      70                      75                      80

Pro Glu Asp Phe Ala Val Tyr Tyr Cys Gln His Tyr Asp Asn Ser Gln
                            85                      90                      95

Thr Phe Gly Gln Gly Thr Lys Val Glu Ile Lys Arg Thr Val Ala Ala
                            100                     105                     110

Pro Ser Val Phe Ile Phe Pro Pro Ser Asp Glu Gln Leu Lys Ser Gly
                            115                     120                     125

Thr Ala Ser Val Val Cys Leu Leu Asn Asn Phe Tyr Pro Arg Glu Ala
                            130                     135                     140

Lys Val Gln Trp Lys Val Asp Asn Ala Leu Gln Ser Gly Asn Ser Gln
            145                     150                     155                     160

Glu Ser Val Thr Glu Gln Asp Ser Lys Asp Ser Thr Tyr Ser Leu Ser
                            165                     170                     175

Ser Thr Leu Thr Leu Ser Lys Ala Asp Tyr Glu Lys His Lys Val Tyr
                            180                     185                     190

Ala Cys Glu Val Thr His Gln Gly Leu Ser Ser Pro Val Thr Lys Ser
                            195                     200                     205

Phe Asn Arg Gly Glu Cys
                            210

<210> SEQ ID NO 30
<211> LENGTH: 107
<212> TYPE: PRT
<213> ORGANISM: Homo sapiens

<400> SEQUENCE: 30

Ile Val Leu Thr Gln Ser Pro Gly Thr Leu Ser Leu Ser Pro Gly Glu
             1               5                      10                      15

Arg Ala Thr Leu Ser Cys Arg Ala Ser Gln Ser Val Ser Ser Thr Tyr
                            20                      25                      30

Leu Ala Trp Tyr Gln Gln Lys Pro Gly Gln Ala Pro Arg Leu Leu Ile
                            35                      40                      45

Tyr Gly Ala Ser Ser Arg Ala Thr Gly Ile Pro Asp Arg Phe Ser Gly
             50                      55                      60

Ser Gly Ser Gly Thr Asp Phe Thr Leu Thr Ile Ser Arg Leu Glu Pro
             65                      70                      75                      80

Glu Asp Phe Ala Val Tyr Tyr Cys Gln His Tyr Asp Asn Ser Gln Thr
                            85                      90                      95

Phe Gly Gln Gly Thr Lys Val Glu Ile Lys Arg
                            100                     105

<210> SEQ ID NO 31
<211> LENGTH: 2986
<212> TYPE: DNA
<213> ORGANISM: Artificial
<220> FEATURE:
<223> OTHER INFORMATION: Synthetic construct

<400> SEQUENCE: 31
```

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtgggag gtctatataa gcagagctca tgatagaagc actctactat tcgtcgaccg   600
atcctgagaa cttcagggtg agtttgggga cccttgattg ttctttcttt ttcgctattg   660
taaaattcat gttatatgga gggggcaaag ttttcagggt gttgtttaga atgggaagat   720
gtcccttgta tcaccatgga ccctcatgat aattttgttt ctttcacttt ctactctgtt   780
gacaaccatt gtctcctctt attttctttt cattttctgt aacttttttcg ttaaacttta   840 gcttgcattt gtaacgaatt tttaaattca cttttgttta tttgtcagat tgtaagtact   900
ttctctaatc actttttttt caaggcaatc agggtatatt atattgtact tcagcacagt   960
tttagagaac aattgttata attaaatgat aaggtagaat atttctgcat ataaattctg  1020
gctggcgtgg aaatattctt attggtagaa acaactacac cctggtcatc atcctgcctt  1080
tctctttatg gttacaatga tatacactgt ttgagatgag gataaaatac tctgagtcca  1140
aaccgggccc ctctgctaac catgttcatg ccttcttctc tttcctacag ctcctgggca  1200
acgtgctggt tgttgtgctg tctcatcatt ttggcaaaga attaagctta tactcgagct  1260
ctagattggg aacccgggtc tctcgaattc gagatctcca ccatgcacag acctagacgt  1320
cgtggaactc gtccacctcc actggcactg ctcgctgctc tcctcctggc tgcacgtggt  1380
gctgatgcag aggtgcagct ggtggagtct gggggaggct tggtacagcc ggggggggtcc  1440 ctgagactct cctgtgcagc ctctggattc accttcagta gctacgacat acactgggtc  1500
cgtcaagcta caggaaaagg tctggagtgg gtctcagcta ttggtcctgc tggtgacaca  1560
tactatccag gctccgtgaa gggccgattc accatctcca gagaaaatgc caagaactcc  1620
ttgtatcttc aaatgaacag cctgagagcc ggggacacgg ctgtgtatta ctgtgcaaga  1680
ggtttgatta cgtttggggg gcttatcgcc ccgtttgact actggggcca gggaaccctg  1740
gtcaccgtct cctcagcctc caccaagggc ccatcggtct tccccctggc accctcctcc  1800
aagagcacct ctgggggcac agcggccctg ggctgcctgg tcaaggacta cttccccgaa  1860
ccggtgacgg tgtcgtggaa ctcaggcgcc ctgaccagcg gcgtgcacac cttcccggct  1920
gtcctacagt cctcaggact ctactccctc agcagcgtgg tgaccgtgcc ctccagcagc  1980
ttgggcaccc agacctacat ctgcaacgtg aatcacaagc ccagcaacac caaggtggac  2040
aagaaagttg agcccaaatc ttgtgacaaa actcacacat gcccaccgtg cccagcacct  2100
gaactcctgg ggggaccgtc agtcttcctc ttccccccaa acccaaggac acccctcatg  2160
atctcccgga cccctgaggt cacatgcgtg gtggtggacg tgagccacga agaccctgag  2220
gtcaagttca actggtacgt ggacggcgtg gaggtgcata atgccaagac aaagccgcgg  2280
gaggagcagt acaacagcac gtaccgtgtg gtcagcgtcc tcaccgtcct gcaccaggac  2340
```

| | |
|---|---|
| tggctgaatg gcaaggagta caagtgcaag gtctccaaca aagccctccc agccccatc | 2400 |
| gagaaaacca tctccaaagc caaagggcag ccccgagaac cacaggtgta caccctgccc | 2460 |
| ccatcccggg atgagctgac caagaaccag gtcagcctga cctgcctggt caaaggcttc | 2520 |
| tatcccagcg acatcgccgt ggagtgggag agcaatgggc agccggagaa caactacaag | 2580 |
| accacgcctc ccgtgctgga ctccgacggc tccttcttcc tctacagcaa gctcaccgtg | 2640 |
| gacaagagca ggtggcagca ggggaacgtc ttctcatgct ccgtgatgca tgaggctctg | 2700 |
| cacaaccact acacgcagaa gtccctctcc ctgtctccgg gtaaatgagc ggccgctaat | 2760 |
| cagccatacc acatttgtag aggttttact tgctttaaaa aacctcccac acctcccct | 2820 |
| gaacctgaaa cataaaatga atgcaattgt tgttgttaac ttgtttattg cagcttataa | 2880 |
| tggttacaaa taaagcaata gcatcacaaa tttcacaaat aaagcatttt tttcactgca | 2940 |
| ttctagttgt ggtttgtcca aactcatcaa tgtatcttat catgtc | 2986 |

<210> SEQ ID NO 32
<211> LENGTH: 7028
<212> TYPE: DNA
<213> ORGANISM: Artificial
<220> FEATURE:
<223> OTHER INFORMATION: Synthetic plasmid

<400> SEQUENCE: 32

| | |
|---|---|
| tcgcgatgtg tgactagtta gttattaata gtaatcaatt acggggtcat tagttcatag | 60 |
| cccatatatg gagttccgcg ttacataact tacggtaaat ggcccgcctg gctgaccgcc | 120 |
| caacgacccc cgcccattga cgtcaataat gacgtatgtt cccatagtaa cgccaatagg | 180 |
| gactttccat tgacgtcaat gggtggagta tttacggtaa actgcccact tggcagtaca | 240 |
| tcaagtgtat catatgccaa gtacgccccc tattgacgtc aatgacggta aatggcccgc | 300 |
| ctggcattat gcccagtaca tgaccttatg gactttcct acttggcagt acatctacgt | 360 |
| attagtcatc gctattacca tggtgatgcg gttttggcag tacatcaatg ggcgtggata | 420 |
| gcggtttgac tcacggggat ttccaagtct ccaccccatt gacgtcaatg ggagtttgtt | 480 |
| ttggcaccaa aatcaacggg actttccaaa atgtcgtaac aactccgccc cattgacgca | 540 |
| aatgggcggt aggcgtgtac ggtgggaggt ctatataagc agagctcatg atagaagcac | 600 |
| tctactattc gtcgaccgat cctgagaact tcagggtgag tttggggacc cttgattgtt | 660 |
| ctttctttt cgctattgta aaattcatgt tatatggagg gggcaaagtt ttcagggtgt | 720 |
| tgtttagaat gggaagatgt cccttgtatc accatggacc ctcatgataa ttttgtttct | 780 |
| ttcactttct actctgttga caaccattgt ctcctcttat tttcttttca ttttctgtaa | 840 |
| cttttcgtt aaactttagc ttgcatttgt aacgaatttt taaattcact tttgtttatt | 900 |
| tgtcagattg taagtacttt ctctaatcac tttttttca aggcaatcag ggtatattat | 960 |
| attgtacttc agcacagttt tagagaacaa ttgttataat taaatgataa ggtagaatat | 1020 |
| ttctgcatat aaattctggc tggcgtggaa atattcttat tggtagaaac aactacaccc | 1080 |
| tggtcatcat cctgcctttc tctttatggt tacaatgata tacactgttt gagatgagga | 1140 |
| taaaatactc tgagtccaaa ccgggcccct ctgctaacca tgttcatgcc ttcttctctt | 1200 |
| tcctacagct cctgggcaac gtgctggttg ttgtgctgtc tcatcatttt ggcaaagaat | 1260 |
| taagcttata ctcgagctct agattgggaa cccgggtctc tcgaattcga gatctccacc | 1320 |
| atgcacagac ctagacgtcg tggaactcgt ccacctccac tggcactgct cgctgctctc | 1380 |
| ctcctggctg cacgtggtgc tgatgcagag gtgcagctgg tggagtctgg gggaggcttg | 1440 |

```
gtacagccgg gggggtccct gagactctcc tgtgcagcct ctggattcac cttcagtagc    1500
tacgacatac actgggtccg tcaagctaca ggaaaaggtc tggagtgggt ctcagctatt    1560
ggtcctgctg gtgacacata ctatccaggc tccgtgaagg gccgattcac catctccaga    1620
gaaaatgcca agaactcctt gtatcttcaa atgaacagcc tgagagccgg gacacggct    1680 gtgtattact gtgcaagagg tttgattacg tttgggggc ttatcgcccc gtttgactac    1740
tggggccagg gaaccctggt caccgtctcc tcagcctcca ccaagggccc atcggtcttc    1800
cccctggcac cctcctccaa gagcacctct ggggggcacag cggccctggg ctgcctggtc    1860
aaggactact ccccgaacc ggtgacggtg tcgtggaact caggcgccct gaccagcggc    1920
gtgcacacct tcccggctgt cctacagtcc tcaggactct actccctcag cagcgtggtg    1980
accgtgccct ccagcagctt gggcacccag acctacatct gcaacgtgaa tcacaagccc    2040
agcaacacca aggtggacaa gaaagttgag cccaaatctt gtgacaaaac tcacacatgc    2100
ccaccgtgcc cagcacctga actcctgggg gaccgtcag tcttcctctt ccccccaaaa    2160
cccaaggaca ccctcatgat ctcccggacc cctgaggtca catgcgtggt ggtggacgtg    2220
agccacgaag accctgaggt caagttcaac tggtacgtgg acggcgtgga ggtgcataat    2280
gccaagacaa agccgcggga ggagcagtac aacagcacgt accgtgtggt cagcgtcctc    2340
accgtcctgc accaggactg gctgaatggc aaggagtaca gtgcaaggt ctccaacaaa    2400 gccctcccag cccccatcga gaaaaccatc tccaaagcca agggcagcc ccgagaacca    2460 caggtgtaca ccctgccccc atcccgggat gagctgacca gaaccaggt cagcctgacc    2520 tgcctggtca aaggcttcta tcccagcgac atcgccgtgg agtgggagag caatgggcag    2580
ccggagaaca actacaagac cacgcctccc gtgctggact ccgacggctc cttcttcctc    2640
tacagcaagc tcaccgtgga caagagcagg tggcagcagg ggaacgtctt ctcatgctcc    2700
gtgatgcatg aggctctgca caaccactac acgcagaagt ccctctccct gtctccgggt    2760
aaatgagcgg ccgctaatca gccataccac atttgtagag gttttacttg ctttaaaaaa    2820
cctcccacac ctcccctga acctgaaaca taaaatgaat gcaattgttg ttgttaactt    2880
gtttattgca gcttataatg gttacaaata aagcaatagc atcacaaatt tcacaaataa    2940
agcatttttt tcactgcatt ctagttgtgg tttgtccaaa ctcatcaatg tatcttatca    3000
tgtctaccgg tcctgcaggg cccctctctt catgtgagca aaaggccagc aaaaggccag    3060
gaaccgtaaa aaggccgcgt tgctggcgtt tttccatagg ctccgccccc ctgacgagca    3120
tcacaaaaat cgacgctcaa gtcagaggtg gcgaaacccg acaggactat aaagatacca    3180
ggcgtttccc cctggaagct ccctcgtgcg ctctcctgtt ccgaccctgc cgcttaccgg    3240
atacctgtcc gcctttctcc cttcgggaag cgtggcgctt tctcaatgct cacgctgtag    3300
gtatctcagt tcggtgtagg tcgttcgctc caagctgggc tgtgtgcacg aaccccccgt    3360
tcagcccgac cgctgcgcct tatccggtaa ctatcgtctt gagtccaacc cggtaagaca    3420
cgacttatcg ccactggcag cagccactgg taacaggatt agcagagcga ggtatgtagg    3480
cggtgctaca gagttcttga agtggtggcc taactacggc tacactagaa ggacagtatt    3540
tggtatctgc gctctgctga agccagttac cttcggaaaa agagttggta gctcttgatc    3600
cggcaaacaa accaccgctg gtagcggtgg tttttttgtt tgcaagcagc agattacgcg    3660
cagaaaaaaa ggatcaag aagatccttt gatcttttct acgggtctg acgctcagtg    3720 gaacgaaaac tcacgttaag ggattttggt catgggcgcg cctcatactc ctgcaggcat    3780
```

```
gagattatca aaaaggatct tcacctagat ccttttaaat taaaaatgaa gttttaaatc   3840
aatctaaagt atatatgagt aaacttggtc tgacagttac caatgcttaa tcagtgaggc   3900
acctatctca gcgatctgtc tatttcgttc atccatagtt gcctgactcc ccgtcgtgta   3960
gataactacg atacgggagg gcttaccatc tggccccagt gctgcaatga taccgcgaga   4020
cccacgctca ccggctccag atttatcagc aataaaccag ccagccggaa gggccgagcg   4080
cagaagtggt cctgcaactt tatccgcctc catccagtct attaattgtt gccgggaagc   4140
tagagtaagt agttcgccag ttaatagttt gcgcaacgtt gttgccattg ctacaggcat   4200
cgtggtgtca cgctcgtcgt ttggtatggc ttcattcagc tccggttccc aacgatcaag   4260
gcgagttaca tgatccccca tgttgtgcaa aaaagcggtt agctccttcg gtcctccgat   4320
cgttgtcaga agtaagttgg ccgcagtgtt atcactcatg gttatggcag cactgcataa   4380
ttctcttact gtcatgccat ccgtaagatg cttttctgtg actggtgagt actcaaccaa   4440
gtcattctga aatagtgta tgcggcgacc gagttgctct tgcccggcgt caatacggga   4500
taataccgcg ccacatagca gaactttaaa agtgctcatc attggaaaac gttcttcggg   4560
gcgaaaactc tcaaggatct taccgctgtt gagatccagt tcgatgtaac ccactcgtgc   4620
acccaactga tcttcagcat cttttacttt caccagcgtt tctgggtgag caaaaacagg   4680
aaggcaaaat gccgcaaaaa agggaataag ggcgacacgg aaatgttgaa tactcatact   4740
cttcctttt caatattatt gaagcattta tcagggttat tgtctcatga gcggatacat   4800
atttgaatgt atttagaaaa ataaacaaat aggggttccg cgcacatttc cccgaaaagt   4860
gccacctgac gtcaggtacc aagcctaggc ctccaaaaaa gcctcctcac tacttctgga   4920
atagctcaga ggcagaggcg gcctcggcct ctgcataaat aaaaaaaatt agtcagccat   4980
ggggcggaga atgggcggaa ctgggcggag ttaggggcgg gatgggcgga gttaggggcg   5040
ggactatggt tgctgactaa ttgagatgca tgctttgcat acttctgcct gctggggagc   5100
ctggggactt tccacacctg gttgctgact aattgagatg catgctttgc atacttctgc   5160
ctgctgggga gcctggggac tttccacacc ggatccacca tggatagatc cggaaagcct   5220
gaactcaccg cgacgtctgt cgagaagttt ctgatcgaaa agttcgacag cgtctccgac   5280
ctgatgcagc tctcggaggg cgaagaatct cgtgctttca gcttcgatgt aggagggcgt   5340
ggatatgtcc tgcgggtaaa tagctgcgcc gatggtttct acaaagatcg ttatgtttat   5400
cggcactttg catcggccgc gctcccgatt ccggaagtgc ttgacattgg ggagttcagc   5460
gagagcctga cctattgcat ctcccgccgt gcacagggtg tcacgttgca agacctgcct   5520
gaaaccgaac tgcccgctgt tctgcagccg gtcgcggagg ccatggatgc gatcgctgcg   5580
gccgatctta gccagacgag cgggttcggc ccattcggac cgcaaggaat cggtcaatac   5640
actacatggc gtgatttcat atgcgcgatt gctgatcccc atgtgtatca ctggcaaact   5700
gtgatggacg acaccgtcag tgcgtccgtc gcgcaggctc tcgatgagct gatgctttgg   5760
gccgaggact gccccgaagt ccggcacctc gtgcacgcgg atttcggctc caacaatgtc   5820
ctgacggaca atggccgcat aacagcggtc attgactgga gcgaggcgat gttcggggat   5880
tcccaatacg aggtcgccaa catcttcttc tggaggccgt ggttggcttg tatggagcag   5940
cagacgcgct acttcgagcg gaggcatccg gagcttgcag atcgccgcg gctccgggcg   6000
tatatgctcc gcattggtct tgaccaactc tatcagagct tggttgacgg caatttcgat   6060
gatgcagctt gggcgcaggg tcgatgcgac gcaatcgtcc gatccggagc cgggactgtc   6120
gggcgtacac aaatcgcccg cagaagcgcg gccgtctgga ccgatggctg tgtagaagta   6180
```

```
ctcgccgata gtggaaaccg acgccccagc actcgtccga gggcaaagga atagacgcgt     6240
gctgtaagtc tgcagaaatt gatgatctat taaacaataa agatgtccac taaaatggaa     6300 gttttttcctg tcatactttg ttaagaaggg tgagaacaga gtacctacat tttgaatgga    6360
aggattggag ctacgggggt gggggtgggg tgggattaga taaatgcctg ctctttactg     6420
aaggctcttt actattgctt tatgataatg tttcatagtt ggatatcata atttaaacaa     6480
gcaaaaccaa attaagggcc agctcattcc tcccactcat gatctatgga tctatagatc     6540
tctcgtgcag ctggggctct aggggggtatc cccacgcgcc ctgtagcggc gcattaagcg    6600
cggcgggtgt ggtggttacg cgcagcgtga ccgctacact tgccagcgcc ctagcgcccg     6660
ctcctttcgc tttcttccct tcctttctcg ccacgttcgc cggctttccc cgtcaagctc     6720
taaatcgggg gctccctta ggggttccgat ttagtgcttt acggcacctc gaccccaaaa    6780
aacttgatta gggtgatggt tcacgtagtg ggccatcgcc ctgatagacg gttttttcgcc   6840 ctttgacgtt ggagtccacg ttctttaata gtggactctt gttccaaact ggaacaacac    6900
tcaaccctat ctcggtctat tcttttgatt tataagggat tttgccgatt tcggcctatt    6960
ggttaaaaaa tgagctgatt taacaaaaat ttaacgcgaa ttaattctgt ggaatgtgtg    7020
tcagttag                                                             7028

<210> SEQ ID NO 33
<211> LENGTH: 2272
<212> TYPE: DNA
<213> ORGANISM: Artificial
<220> FEATURE:
<223> OTHER INFORMATION: Synthetic construct

<400> SEQUENCE: 33
tagttattaa tagtaatcaa ttacggggtc attagttcat agcccatata tggagttccg       60
cgttacataa cttacggtaa atggcccgcc tggctgaccg cccaacgacc cccgcccatt      120
gacgtcaata atgacgtatg ttcccatagt aacgccaata gggactttcc attgacgtca      180
atgggtggag tatttacggt aaactgccca cttggcagta catcaagtgt atcatatgcc      240
aagtacgccc cctattgacg tcaatgacgg taaatggccc gcctggcatt atgcccagta      300
catgacctta tgggactttc ctacttggca gtacatctac gtattagtca tcgctattac      360
catggtgatg cggttttggc agtacatcaa tgggcgtgga tagcggtttg actcacgggg      420
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctca tgatagaagc actctactat cgtcgaccg      600 atcctgagaa cttcagggtg agtttgggga cccttgattg ttctttcttt ttcgctattg      660
taaaattcat gttatatgga gggggcaaag ttttcagggt gttgtttaga atgggaagat      720
gtcccttgta tcaccatgga ccctcatgat aattttgttt ctttcacttt ctactctgtt      780
gacaaccatt gtctcctctt atttttcttt cattttctgt aacttttttcg ttaaacttta     840 gcttgcattt gtaacgaatt tttaaattca cttttgtttta tttgtcagat tgtaagtact      900
ttctctaatc actttttttt caaggcaatc agggtatatt atattgtact tcagcacagt      960
tttagagaac aattgttata attaaatgat aaggtagaat atttctgcat ataaattctg     1020
gctggcgtgg aaatattctt attggtagaa acaactacac cctggtcatc atcctgcctt     1080
tctctttatg gttacaatga tatacactgt ttgagatgag gataaaatac tctgagtcca    1140
```

```
aaccgggccc ctctgctaac catgttcatg ccttcttctc tttcctacag ctcctgggca   1200
acgtgctggt tgttgtgctg tctcatcatt ttggcaaaga attaagctta tactcgagct   1260
ctagattggg aacccgggtc tctcgaattc gagatctcca ccatgcacag acctagacgt   1320
cgtggaactc gtccacctcc actggcactg ctcgctgctc tcctcctggc tgcacgtggt   1380
gctgatgcag aaattgtgtt gacgcagtct ccaggcaccc tgtctttgtc tccagggaa    1440 agagccaccc tctcctgcag ggccagtcag agtgttagca gcacctactt agcctggtac   1500
cagcagaaac ctggccaggc tcccaggctc ctcatctatg gtgcatccag cagggccact   1560
ggcatcccag acaggttcag tggcagtggg tctgggacag acttcactct caccatcagc   1620
agactggagc ctgaagattt tgcagtgtat tactgtcagc attatgataa ctcacaaacg   1680
ttcggccaag ggaccaaggt ggagatcaaa cgaactgtgg ctgcaccatc tgtcttcatc   1740
ttcccgccat ctgatgagca gttgaaatct ggaactgcct ctgttgtgtg cctgctgaat   1800
aacttctatc ccagagaggc caaagtacag tggaaggtgg ataacgccct ccaatcgggt   1860
aactcccagg agagtgtcac agagcaggac agcaaggaca gcacctacag cctcagcagc   1920
accctgacgc tgagcaaagc agactacgag aaacacaaag tctacgcctg cgaagtcacc   1980
catcagggcc tgagctcgcc cgtcacaaag agcttcaaca ggggagagtg ttaggcggcc   2040
gctaatcagc cataccacat ttgtagaggt tttacttgct ttaaaaaacc tcccacacct   2100 cccccctgaac ctgaaacata aatgaatgc aattgttgtt gttaacttgt ttattgcagc   2160
ttataatggt tacaaataaa gcaatagcat cacaaatttc acaaataaag cattttttc    2220 actgcattct agttgtggtt tgtccaaact catcaatgta tcttatcatg tc           2272

<210> SEQ ID NO 34
<211> LENGTH: 6335
<212> TYPE: DNA
<213> ORGANISM: Artificial
<220> FEATURE:
<223> OTHER INFORMATION: Synthetic plasmid

<400> SEQUENCE: 34
tcgagctcta gattgggaac ccgggtctct cgaattcgag atctccacca tgcacagacc     60
tagacgtcgt ggaactcgtc cacctccact ggcactgctc gctgctctcc tcctggctgc    120
acgtggtgct gatgcagaaa ttgtgttgac gcagtctcca ggcaccctgt ctttgtctcc    180
aggggaaaga gccacccttct cctgcagggc cagtcagagt gttagcagca cctacttagc    240
ctggtaccag cagaaacctg gccaggctcc caggctcctc atctatggtg catccagcag    300
ggccactggc atcccagaca ggttcagtgg cagtgggtct gggacagact tcactctcac    360
catcagcaga ctggagcctg aagattttgc agtgtattac tgtcagcatt atgataactc    420
acaaacgttc ggccaaggga ccaaggtgga gatcaaacga actgtggctg caccatctgt    480
cttcatcttc ccgccatctg atgagcagtt gaaatctgga actgcctctg ttgtgtgcct    540
gctgaataac ttctatccca gagaggccaa agtacagtgg aaggtggata acgccctcca    600
atcgggtaac tcccaggaga gtgtcacaga gcaggacagc aaggacagca cctacagcct    660
cagcagcacc ctgacgctga gcaaagcaga ctacgagaaa cacaaagtct acgcctgcga    720
agtcacccat cagggcctga gctcgcccgt cacaaagagc ttcaacaggg gagagtgtta    780
ggcggccgct aatcagccat accacatttg tagaggtttt acttgcttta aaaaacctcc    840
cacacctccc cctgaacctg aaacataaaa tgaatgcaat tgttgttgtt aacttgttta    900
ttgcagctta atggttac aaataaagca atagcatcac aaatttcaca ataaagcat       960
```

```
tttttttcact gcattctagt tgtggtttgt ccaaactcat caatgtatct tatcatgtct   1020
accggtaggg cccctctctt catgtgagca aaaggccagc aaaaggccag gaaccgtaaa   1080
aaggccgcgt tgctggcgtt tttccatagg ctccgccccc ctgacgagca tcacaaaaat   1140
cgacgctcaa gtcagaggtg gcgaaacccg acaggactat aaagatacca ggcgtttccc   1200
cctggaagct ccctcgtgcg ctctcctgtt ccgaccctgc cgcttaccgg atacctgtcc   1260
gcctttctcc cttcgggaag cgtggcgctt tctcaatgct cacgctgtag gtatctcagt   1320
tcggtgtagg tcgttcgctc caagctgggc tgtgtgcacg aaccccccgt tcagcccgac   1380
cgctgcgcct tatccggtaa ctatcgtctt gagtccaacc cggtaagaca cgacttatcg   1440
ccactggcag cagccactgg taacaggatt agcagagcga ggtatgtagg cggtgctaca   1500
gagttcttga agtggtggcc taactacggc tacactagaa ggacagtatt tggtatctgc   1560
gctctgctga agccagttac cttcggaaaa agagttggta gctcttgatc cggcaaacaa   1620
accaccgctg gtagcggtgg ttttttgtt tgcaagcagc agattacgcg cagaaaaaaa   1680
ggatctcaag aagatccttt gatcttttct acggggtctg acgctcagtg aacgaaaac   1740 tcacgttaag ggattttggt catgggcgcg gcatgagat tatcaaaaag gatcttcacc   1800
tagatccttt taaattaaaa atgaagtttt aaatcaatct aaagtatata tgagtaaact   1860
tggtctgaca gttaccaatg cttaatcagt gaggcaccta tctcagcgat ctgtctattt   1920
cgttcatcca tagttgcctg actccccgtc gtgtagataa ctacgatacg ggagggctta   1980
ccatctggcc ccagtgctgc aatgatacccg cgagacccac gctcaccggc tccagattta   2040
tcagcaataa accagccagc cggaagggcc gagcgcagaa gtggtcctgc aactttatcc   2100
gcctccatcc agtctattaa ttgttgccgg gaagctagag taagtagttc gccagttaat   2160
agtttgcgca acgttgttgc cattgctaca ggcatcgtgg tgtcacgctc gtcgtttggt   2220
atggcttcat tcagctccgg ttcccaacga tcaaggcgag ttacatgatc ccccatgttg   2280
tgcaaaaaag cggttagctc cttcggtcct ccgatcgttg tcagaagtaa gttggccgca   2340
gtgttatcac tcatggttat ggcagcactg cataattctc ttactgtcat gccatccgta   2400
agatgctttt ctgtgactgg tgagtactca accaagtcat tctgagaata gtgtatgcgg   2460
cgaccgagtt gctcttgccc ggcgtcaata cgggataata ccgcgccaca tagcagaact   2520
ttaaaagtgc tcatcattgg aaaacgttct tcggggcgaa aactctcaag gatcttaccg   2580
ctgttgagat ccagttcgat gtaacccact cgtgcaccca actgatcttc agcatctttt   2640
actttcacca gcgtttctgg gtgagcaaaa acaggaaggc aaaatgccgc aaaaaaggga   2700
ataagggcga cacggaaatg ttgaatactc atactcttcc tttttcaata ttattgaagc   2760
atttatcagg gttattgtct catgagcgga tacatatttg aatgtattta gaaaaataaa   2820 caaataggg ttccgcgcac atttccccga aaagtgccac ctgacgtcag gtacacttag   2880
gcgcgccatt agagttcctg caggctacat ggtaccaagc ctaggcctcc aaaaaagcct   2940
cctcactact tctggaatag ctcagaggca gaggcggcct cggcctctgc ataaataaaa   3000
aaaattagtc agccatgggg cggagaatgg gcggaactgg gcggagttag ggcgggatg   3060 ggcggagtta gggcgggac tatggttgct gactaattga gatgcatgct ttgcatactt   3120
ctgcctgctg gggagcctgg ggactttcca cacctggttg ctgactaatt gagatgcatg   3180
ctttgcatac ttctgcctgc tggggagcct ggggactttc cacaccggat ccaccatgga   3240
tagatccgga aagcctgaac tcaccgcgac gtctgtcgag aagtttctga tcgaaaagtt   3300
```

```
cgacagcgtc tccgacctga tgcagctctc ggagggcgaa gaatctcgtg ctttcagctt    3360
cgatgtagga gggcgtggat atgtcctgcg ggtaaatagc tgcgccgatg gtttctacaa    3420
agatcgttat gtttatcggc actttgcatc ggccgcgctc ccgattccgg aagtgcttga    3480
cattggggag ttcagcgaga gcctgaccta ttgcatctcc cgccgtgcac agggtgtcac    3540
gttgcaagac ctgcctgaaa ccgaactgcc cgctgttctg cagccggtcg cggaggccat    3600
ggatgcgatc gctgcggccg atcttagcca gacgagcggg ttcggcccat tcggaccgca    3660
aggaatcggt caatacacta catggcgtga tttcatatgc gcgattgctg atccccatgt    3720
gtatcactgg caaactgtga tggacgacac cgtcagtgcg tccgtcgcgc aggctctcga    3780
tgagctgatg ctttgggccg aggactgccc cgaagtccgg cacctcgtgc acgcggattt    3840
cggctccaac aatgtcctga cggacaatgg ccgcataaca gcggtcattg actggagcga    3900
ggcgatgttc ggggattccc aatacgaggt cgccaacatc ttcttctgga ggccgtggtt    3960
ggcttgtatg gagcagcaga cgcgctactt cgagcggagg catccggagc ttgcaggatc    4020
gccgcggctc cgggcgtata tgctccgcat tggtcttgac caactctatc agagcttggt    4080
tgacggcaat ttcgatgatg cagcttgggc gcagggtcga tgcgacgcaa tcgtccgatc    4140
cggagccggg actgtcgggc gtacacaaat cgcccgcaga agcgcggccg tctggaccga    4200
tggctgtgta aagtactcg ccgatagtgg aaaccgacgc cccagcactc gtccgagggc    4260
aaaggaatag acgcgtgctg taagtctgca gaaattgatg atctattaaa caataaagat    4320
gtccactaaa atggaagttt ttcctgtcat actttgttaa gaagggtgag aacagagtac    4380
ctacattttg aatggaagga ttggagctac ggggtgggg gtgggtggg attagataaa    4440
tgcctgctct ttactgaagg ctcttttacta ttgctttatg ataatgtttc atagttggat    4500
atcataattt aaacaagcaa aaccaaatta agggccagct cattcctccc actcatgatc    4560
tatggatcta tagatctctc gtgcagctgg ggctctaggg ggtatcccca cgcgccctgt    4620
agcggcgcat taagcgcggc gggtgtggtg gttacgcgca gcgtgaccgc tacacttgcc    4680
agcgccctag cgcccgctcc tttcgctttc ttcccttcct ttctcgccac gttcgccggc    4740
tttccccgtc aagctctaaa tcgggggctc cctttagggt tccgatttag tgctttacgg    4800
cacctcgacc ccaaaaaact tgattagggt gatggttcac gtagtgggcc atcgccctga    4860
tagacggttt ttcgcccttt gacgttggag tccacgttct ttaatagtgg actcttgttc    4920
caaactggaa caacactcaa ccctatctcg gtctattctt ttgatttata agggattttg    4980
ccgatttcgg cctattggtt aaaaaatgag ctgatttaac aaaaatttaa cgcgaattaa    5040
ttctgtggaa tgtgtgtcag ttagtcgcga tgtgtgacta gttagttatt aatagtaatc    5100
aattacgggg tcattagttc atagcccata tatggagttc cgcgttacat aacttacggt    5160
aaatggcccg cctggctgac cgcccaacga cccccgccca ttgacgtcaa taatgacgta    5220
tgttcccata gtaacgccaa tagggacttt ccattgacgt caatgggtgg agtatttacg    5280
gtaaactgcc cacttggcag tacatcaagt gtatcatatg ccaagtacgc ccctattga    5340
cgtcaatgac ggtaaatggc ccgcctggca ttatgcccag tacatgacct tatgggactt    5400
tcctacttgg cagtacatct acgtattagt catcgctatt accatggtga tgcggttttg    5460
gcagtacatc aatgggcgtg atagcggttt tgactcacgg ggatttccaa gtctccaccc    5520
cattgacgtc aatgggagtt tgttttggca ccaaaatcaa cgggactttc caaaatgtcg    5580
taacaactcc gccccattga cgcaaatggg cggtaggcgt gtacggtggg aggtctatat    5640
aagcagagct catgatagaa gcactctact attcgtcgac cgatcctgag aacttcaggg    5700
```

```
tgagtttggg gaccccttgat tgttctttct ttttcgctat tgtaaaattc atgttatatg   5760
gaggggcaa agttttcagg gtgttgttta gaatgggaag atgtcccttg tatcaccatg     5820
gaccctcatg ataattttgt ttcttttcact ttctactctg ttgacaacca ttgtctcctc   5880
ttattttctt ttcattttct gtaacttttt cgttaaactt tagcttgcat ttgtaacgaa   5940
tttttaaatt cacttttgtt tatttgtcag attgtaagta ctttctctaa tcactttttt   6000
ttcaaggcaa tcagggtata ttatattgta cttcagcaca gttttagaga acaattgtta   6060
taattaaatg ataaggtaga atatttctgc atataaattc tggctggcgt ggaaatattc   6120
ttattggtag aaacaactac accctggtca tcatcctgcc tttctcttta tggttacaat   6180
gatatacact gtttgagatg aggataaaat actctgagtc caaaccgggc ccctctgcta   6240
accatgttca tgccttcttc tctttcctac agctcctggg caacgtgctg gttgttgtgc   6300
tgtctcatca ttttggcaaa gaattaagct tatac                              6335
```

<210> SEQ ID NO 35
<211> LENGTH: 449
<212> TYPE: PRT
<213> ORGANISM: Homo sapiens

<400> SEQUENCE: 35

```
Gln Val Gln Leu Gln Gln Ser Gly Ala Gly Leu Leu Lys Pro Ser Glu
1               5                   10                  15

Thr Leu Ser Leu Thr Cys Thr Val Tyr Gly Gly Ser Phe Ser Ile His
            20                  25                  30

His Trp Thr Trp Ile Arg His Pro Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ala Val Thr Ala Ala Asp Thr Ala Val Tyr Tyr Cys Ala
                85                  90                  95

Arg Gly Leu Arg Phe Leu Asp Trp Leu Ser Ser Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 36
<211> LENGTH: 103
<212> TYPE: PRT
<213> ORGANISM: Homo sapiens

<400> SEQUENCE: 36

Gln Ser Gly Ala Gly Leu Leu Lys Pro Ser Glu Thr Leu Ser Leu Thr
1               5                   10                  15

Cys Thr Val Tyr Gly Gly Ser Phe Ser Ile His His Trp Thr Trp Ile
            20                  25                  30

Arg His Pro Pro Gly Lys Gly Leu Glu Trp Ile Gly Glu Ile Asn His
        35                  40                  45

Arg Gly Ser Thr Asn Tyr Asn Pro Ser Leu Lys Ser Arg Val Thr Ile
    50                  55                  60

Ser Ile Asp Thr Ser Lys Asn Gln Phe Ser Leu Lys Leu Ser Ala Val
65                  70                  75                  80

Thr Ala Ala Asp Thr Ala Val Tyr Tyr Cys Ala Arg Gly Leu Arg Phe
                85                  90                  95

Leu Asp Trp Leu Ser Ser Tyr
            100

<210> SEQ ID NO 37
<211> LENGTH: 214
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asp Tyr
```

```
                    20                  25                  30
Leu Ala Trp Tyr Gln Gln Lys Pro Gly Lys Val Pro Asn Leu Leu Ile
            35                  40                  45
Tyr Ala Ala Ser Ala Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Cys Gln Asn Tyr Asn Thr Ala Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 38
<211> LENGTH: 107
<212> TYPE: PRT
<213> ORGANISM: Homo sapiens

<400> SEQUENCE: 38

Ile Gln Met Thr Gln Ser Pro Ser Ser Leu Ser Ala Ser Val Gly Asp
 1               5                  10                  15
Arg Val Thr Ile Thr Cys Arg Ala Ser Gln Gly Ile Ser Asp Tyr Leu
                20                  25                  30
Ala Trp Tyr Gln Gln Lys Pro Gly Lys Val Pro Asn Leu Leu Ile Tyr
            35                  40                  45
Ala Ala Ser Ala Leu Gln Ser Gly Val Pro Ser Arg Phe Ser Gly Ser
 50                  55                  60
Gly Ser Gly Thr Asp Phe Thr Leu Thr Ile Ser Ser Leu Gln Pro Glu
 65                  70                  75                  80
Asp Val Ala Thr Tyr Tyr Cys Gln Asn Tyr Asn Thr Ala Pro Leu Thr
                85                  90                  95
Phe Gly Gly Gly Thr Lys Val Glu Ile Lys Arg
            100                 105

<210> SEQ ID NO 39
<211> LENGTH: 2977
<212> TYPE: DNA
<213> ORGANISM: Artificial
<220> FEATURE:
<223> OTHER INFORMATION: Synthetic construct

<400> SEQUENCE: 39
tagttattaa tagtaatcaa ttacggggtc attagttcat agcccatata tggagttccg    60
```

-continued

| | |
|---|---|
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta acaactccgc cccattgacg caaatgggcg gtaggcgtgt | 540 |
| acggtgggag gtctatataa gcagagctca tgatagaagc actctactat tcgtcgaccg | 600 |
| atcctgagaa cttcagggtg agtttgggga cccttgattg ttctttcttt ttcgctattg | 660 |
| taaaattcat gttatatgga gggggcaaag ttttcagggt gttgtttaga atgggaagat | 720 |
| gtcccttgta tcaccatgga ccctcatgat aattttgttt ctttcacttt ctactctgtt | 780 |
| gacaaccatt gtctcctctt attttctttt cattttctgt aacttttttcg ttaaacttta | 840 |
| gcttgcattt gtaacgaatt tttaaattca cttttgttta tttgtcagat tgtaagtact | 900 |
| ttctctaatc acttttttt caaggcaatc agggtatatt atattgtact tcagcacagt | 960 |
| tttagagaac aattgttata attaaatgat aaggtagaat atttctgcat ataaattctg | 1020 |
| gctggcgtgg aaatattctt attggtagaa acaactacac cctggtcatc atcctgcctt | 1080 |
| tctctttatg gttacaatga tatacactgt ttgagatgag gataaaatac tctgagtcca | 1140 |
| aaccgggccc ctctgctaac catgttcatg ccttcttctc tttcctacag ctcctgggca | 1200 |
| acgtgctggt tgttgtgctg tctcatcatt ttggcaaaga attaagctta tactcgagct | 1260 |
| ctagattggg aacccgggtc tctcgaattc gagatctcca ccatgcacag acctagacgt | 1320 |
| cgtggaactc gtccacctcc actggcactg ctcgctgctc tcctcctggc tgcacgtggt | 1380 |
| gctgatgcac aggtacagct gcagcagtcg ggcgcaggac tgttgaagcc ttcggagacc | 1440 |
| ctgtccctca cctgcactgt ctatggtgga tccttcagta ttcatcactg gacctggatc | 1500 |
| cgccatcccc cagggaaggg gctggagtgg attggggaga tcaatcatcg tggaagcacc | 1560 |
| aactacaacc cgtccctcaa gagtcgagtc accatatcaa tagacacgtc caagaaccag | 1620 |
| ttctccctga agctgagcgc tgtgaccgcc gcggacacgg ctgtatatta ctgtgcgaga | 1680 |
| ggcttacgat tttggactg gttatcgtcc tactttgact actggggcca gggaaccctg | 1740 |
| gtcaccgtct cctcagcctc caccaagggc ccatcggtct tccccctggc gcctgctcc | 1800 |
| aggagcacct ccgagagcac agccgccctg ggctgcctgg tcaaggacta cttccccgaa | 1860 |
| ccggtgacgg tgtcgtggaa ctcaggcgcc ctgaccagcg gcgtgcacac cttcccggct | 1920 |
| gtcctacagt cctcaggact ctactccctc agcagcgtgg tgaccgtgcc ctccagcagc | 1980 |
| ttgggcacga agacctacac ctgcaacgta gatcacaagc ccagcaacac caaggtggac | 2040 |
| aagagagttg agtccaaata tggtccccca tgcccaccct gcccagcacc tgagttcctg | 2100 |
| gggggaccat cagtcttcct gttcccccca aaacccaagg acactctcat gatctcccgg | 2160 |
| acccctgagg tcacgtgcgt ggtggtggac gtgagccagg aagaccccga ggtccagttc | 2220 |
| aactggtacg tggatggcgt ggaggtgcat aatgccaaga caaagccgcg ggaggagcag | 2280 |
| ttcaacagca cgtaccgtgt ggtcagcgtc ctcaccgtcc tgcaccagga ctggctgaac | 2340 |
| ggcaaggagt acaagtgcaa ggtctccaac aaaggcctcc cgtcctccat cgagaaaacc | 2400 |
| atctccaaag ccaaagggca gccccgagag ccacaggtgt acaccctgcc cccatcccag | 2460 |

```
gaggagatga ccaagaacca ggtcagcctg acctgcctgg tcaaaggctt ctaccccagc    2520
gacatcgccg tggagtggga gagcaatggg cagccggaga caactacaa gaccacgcct    2580 cccgtgctgg actccgacgg ctccttcttc ctctacagca ggctcaccgt ggacaagagc    2640
aggtggcagg aggggaatgt cttctcatgc tccgtgatgc atgaggctct gcacaaccac    2700
tacacacaga gtccctctc cctgtctctg ggtaaatgag cggccgctaa tcagccatac    2760
cacatttgta gaggttttac ttgctttaaa aaacctccca cacctccccc tgaacctgaa    2820
acataaaatg aatgcaattg ttgttgttaa cttgtttatt gcagcttata atggttacaa    2880
ataaagcaat agcatcacaa atttcacaaa taaagcattt ttttcactgc attctagttg    2940
tggtttgtcc aaactcatca atgtatctta tcatgtc                            2977

<210> SEQ ID NO 40
<211> LENGTH: 7019
<212> TYPE: DNA
<213> ORGANISM: Artificial
<220> FEATURE:
<223> OTHER INFORMATION: Synthetic plasmid

<400> SEQUENCE: 40
tcgcgatgtg tgactagtta gttattaata gtaatcaatt acggggtcat tagttcatag      60
cccatatatg gagttccgcg ttacataact tacggtaaat ggcccgcctg gctgaccgcc     120
caacgacccc cgcccattga cgtcaataat gacgtatgtt cccatagtaa cgccaatagg     180
gactttccat tgacgtcaat gggtggagta tttacggtaa actgcccact tggcagtaca     240
tcaagtgtat catatgccaa gtacgccccc tattgacgtc aatgacggta aatggcccgc     300
ctggcattat gcccagtaca tgaccttatg ggactttcct acttggcagt acatctacgt     360
attagtcatc gctattacca tggtgatgcg gttttggcag tacatcaatg ggcgtggata     420
gcggtttgac tcacggggat ttccaagtct ccaccccatt gacgtcaatg ggagtttgtt     480
ttggcaccaa aatcaacggg actttccaaa atgtcgtaac aactccgccc cattgacgca     540
aatgggcggt aggcgtgtac ggtgggaggt ctatataagc agagctcatg atagaagcac     600
tctactattc gtcgaccgat cctgagaact tcagggtgag tttggggacc cttgattgtt     660 ctttctttt cgctattgta aaattcatgt tatatggagg gggcaaagtt ttcagggtgt     720
tgtttagaat gggaagatgt cccttgtatc accatggacc ctcatgataa ttttgtttct     780
ttcactttct actctgttga caaccattgt ctcctcttat tttcttttca ttttctgtaa     840 cttttcgtt aaactttagc ttgcatttgt aacgaatttt taaattcact tttgtttatt     900
tgtcagattg taagtacttt ctctaatcac ttttttttca aggcaatcag ggtatattat     960
attgtacttc agcacagttt tagagaacaa ttgttataat taaatgataa ggtagaatat    1020
ttctgcatat aaattctggc tggcgtggaa atattcttat tggtagaaac aactacaccc    1080
tggtcatcat cctgcctttc tctttatggt tacaatgata tacactgttt gagatgagga    1140
taaaatactc tgagtccaaa ccgggcccct ctgctaacca tgttcatgcc ttcttctctt    1200
tcctacagct cctgggcaac gtgctggttg ttgtgctgtc tcatcatttt ggcaaagaat    1260
taagcttata ctcgagctct agattgggaa cccgggtctc tcgaattcga gatctccacc    1320
atgcacagac ctagacgtcg tggaactcgt ccacctccac tggcactgct cgctgctctc    1380
ctcctggctg cacgtggtgc tgatgcacag gtacagctgc agcagtcggg cgcaggactg    1440
ttgaagcctt cggagaccct gtccctcacc tgcactgtct atggtggatc cttcagtatt    1500
```

-continued

```
catcactgga cctggatccg ccatccccca gggaaggggc tggagtggat tggggagatc    1560
aatcatcgtg gaagcaccaa ctacaacccg tccctcaaga gtcgagtcac catatcaata    1620
gacacgtcca agaaccagtt ctccctgaag ctgagcgctg tgaccgccgc ggacacggct    1680
gtatattact gtgcgagagg cttacgattt ttggactggt tatcgtccta ctttgactac    1740
tggggccagg gaaccctggt caccgtctcc tcagcctcca caagggccc atcggtcttc    1800
cccctggcgc cctgctccag gagcacctcc gagagcacag ccgccctggg ctgcctggtc    1860
aaggactact cccccgaacc ggtgacggtg tcgtggaact caggcgccct gaccagcggc    1920
gtgcacacct tcccggctgt cctacagtcc tcaggactct actccctcag cagcgtggtg    1980
accgtgccct ccagcagctt gggcacgaag acctacacct gcaacgtaga tcacaagccc    2040
agcaacacca aggtggacaa gagagttgag tccaaatatg gtcccccatg cccaccctgc    2100
ccagcacctg agttcctggg gggaccatca gtcttcctgt tccccccaaa acccaaggac    2160
actctcatga tctcccggac ccctgaggtc acgtgcgtgg tggtggacgt gagccaggaa    2220
gaccccgagg tccagttcaa ctggtacgtg gatggcgtgg aggtgcataa tgccaagaca    2280
aagccgcggg aggagcagtt caacagcacg taccgtgtgg tcagcgtcct caccgtcctg    2340
caccaggact ggctgaacgg caaggagtac aagtgcaagg tctccaacaa aggcctcccg    2400
tcctccatcg agaaaaccat ctccaaagcc aaagggcagc cccgagagcc acaggtgtac    2460
accctgcccc catcccagga ggagatgacc aagaaccagg tcagcctgac ctgcctggtc    2520
aaaggcttct accccagcga catcgccgtg gagtgggaga gcaatgggca gccggagaac    2580
aactacaaga ccacgcctcc cgtgctggac tccgacggct ccttcttcct ctacagcagg    2640
ctcaccgtgg acaagagcag gtggcaggag gggaatgtct tctcatgctc cgtgatgcat    2700
gaggctctgc acaaccacta cacacagaag tccctctccc tgtctctggg taaatgagcg    2760
gccgctaatc agccatacca catttgtaga ggttttactt gctttaaaaa acctcccaca    2820
cctcccctg aacctgaaac ataaaatgaa tgcaattgtt gttgttaact tgtttattgc    2880
agcttataat ggttacaaat aaagcaatag catcacaaat ttcacaaata aagcattttt    2940
ttcactgcat tctagttgtg gtttgtccaa actcatcaat gtatcttatc atgtctaccg    3000
gtcctgcagg gcccctctct tcatgtgagc aaaaggccag caaaaggcca ggaaccgtaa    3060
aaaggccgcg ttgctggcgt ttttccatag gctccgcccc cctgacgagc atcacaaaaa    3120
tcgacgctca agtcagaggt ggcgaaaccc gacaggacta taaagatacc aggcgtttcc    3180
ccctggaagc tccctcgtgc gctctcctgt tccgaccctg ccgcttaccg gatacctgtc    3240
cgcctttctc ccttcgggaa gcgtggcgct ttctcaatgc tcacgctgta ggtatctcag    3300
ttcggtgtag gtcgttcgct ccaagctggg ctgtgtgcac gaaccccccg ttcagcccga    3360
ccgctgcgcc ttatccggta actatcgtct tgagtccaac ccggtaagac acgacttatc    3420
gccactggca gcagccactg gtaacaggat tagcagagcg aggtatgtag gcggtgctac    3480
agagttcttg aagtggtggc ctaactacgg ctacactaga aggacagtat ttggtatctg    3540
cgctctgctg aagccagtta ccttcggaaa aagagttggt agctcttgat ccggcaaaca    3600
aaccaccgct ggtagcggtg gtttttttgt ttgcaagcag cagattacgc gcagaaaaaa    3660
aggatctcaa gaagatcctt tgatcttttc tacggggtct gacgctcagt ggaacgaaaa    3720
ctcacgttaa gggattttgg tcatgggcgc gcctcatact cctgcaggca tgagattatc    3780
aaaaaggatc ttcacctaga tccttttaaa ttaaaaatga agttttaaat caatctaaag    3840
tatatatgag taaacttggt ctgacagtta ccaatgctta atcagtgagg cacctatctc    3900
```

```
agcgatctgt ctatttcgtt catccatagt tgcctgactc cccgtcgtgt agataactac    3960
gatacgggag ggcttaccat ctggccccag tgctgcaatg ataccgcgag acccacgctc    4020
accggctcca gatttatcag caataaacca gccagccgga agggccgagc gcagaagtgg    4080
tcctgcaact ttatccgcct ccatccagtc tattaattgt tgccgggaag ctagagtaag    4140
tagttcgcca gttaatagtt tgcgcaacgt tgttgccatt gctacaggca tcgtggtgtc    4200
acgctcgtcg tttggtatgg cttcattcag ctccggttcc caacgatcaa ggcgagttac    4260
atgatccccc atgttgtgca aaaaagcggt tagctccttc ggtcctccga tcgttgtcag    4320
aagtaagttg gccgcagtgt tatcactcat ggttatggca gcactgcata attctcttac    4380
tgtcatgcca tccgtaagat gcttttctgt gactggtgag tactcaacca agtcattctg    4440
agaatagtgt atgcggcgac cgagttgctc ttgcccggcg tcaatacggg ataataccgc    4500
gccacatagc agaactttaa aagtgctcat cattggaaaa cgttcttcgg ggcgaaaact    4560
ctcaaggatc ttaccgctgt tgagatccag ttcgatgtaa cccactcgtg cacccaactg    4620
atcttcagca tcttttactt tcaccagcgt ttctgggtga gcaaaaacag gaaggcaaaa    4680
tgccgcaaaa aagggaataa gggcgacacg gaaatgttga atactcatac tcttcctttt    4740
tcaatattat tgaagcattt atcagggtta ttgtctcatg agcggataca tatttgaatg    4800
tatttagaaa aataaacaaa tagggggttcc gcgcacattt ccccgaaaag tgccacctga    4860
cgtcaggtac caagcctagg cctccaaaaa agcctcctca ctacttctgg aatagctcag    4920
aggcagaggc ggcctcggcc tctgcataaa taaaaaaaat tagtcagcca tggggcggag    4980
aatgggcgga actgggcgga gttaggggcg ggatgggcgg agttaggggc gggactatgg    5040
ttgctgacta attgagatgc atgctttgca tacttctgcc tgctggggag cctggggact    5100
ttccacacct ggttgctgac taattgagat gcatgctttg catacttctg cctgctgggg    5160
agcctgggga ctttccacac cggatccacc atggatagat ccggaaagcc tgaactcacc    5220
gcgacgtctg tcgagaagtt tctgatcgaa aagttcgaca gcgtctccga cctgatgcag    5280
ctctcggagg gcgaagaatc tcgtgctttc agcttcgatg taggagggcg tggatatgtc    5340
ctgcgggtaa atagctgcgc cgatggtttc tacaaagatc gttatgttta tcggcacttt    5400
gcatcggccg cgctcccgat tccggaagtg cttgacattg gggagttcag cgagagcctg    5460
acctattgca tctcccgccg tgcacagggt gtcacgttgc aagacctgcc tgaaaccgaa    5520
ctgcccgctg ttctgcagcc ggtcgcggag gccatggatg cgatcgctgc ggccgatctt    5580
agccagacga gcgggttcgg cccattcgga ccgcaaggaa tcggtcaata cactacatgg    5640
cgtgatttca tatgcgcgat tgctgatccc catgtgtatc actggcaaac tgtgatggac    5700
gacaccgtca gtgcgtccgt cgcgcaggct ctcgatgagc tgatgctttg ggccgaggac    5760
tgccccgaag tccggcacct cgtgcacgcg gatttcggct ccaacaatgt cctgacggac    5820
aatggccgca taacagcggt cattgactgg agcgaggcga tgttcgggga ttcccaatac    5880
gaggtcgcca acatcttctt ctggaggccg tggttggctt gtatggagca gcagacgcgc    5940
tacttcgagc ggaggcatcc ggagcttgca ggatcgccgc ggctccgggc gtatatgctc    6000
cgcattggtc ttgaccaact ctatcagagc ttggttgacg gcaatttcga tgatgcagct    6060
tgggcgcagg tcgatgcgga cgcaatcgtc cgatccggag ccgggactgt cgggcgtaca    6120
caaatcgccc gcagaagcgc ggccgtctgg accgatggct gtgtagaagt actcgccgat    6180
agtggaaacc gacgccccag cactcgtccg agggcaaagg aatagacgcg tgctgtaagt    6240
```

| | |
|---|---|
| ctgcagaaat tgatgatcta ttaaacaata aagatgtcca ctaaaatgga agttttcct | 6300 |
| gtcatacttt gttaagaagg gtgagaacag agtacctaca ttttgaatgg aaggattgga | 6360 |
| gctacggggg tggggtgggg gtgggattag ataaatgcct gctctttact gaaggctctt | 6420 |
| tactattgct ttatgataat gtttcatagt tggatatcat aatttaaaca agcaaaacca | 6480 |
| aattaagggc cagctcattc ctcccactca tgatctatgg atctatagat ctctcgtgca | 6540 |
| gctgggctc taggggtat ccccacgcgc cctgtagcgg cgcattaagc gcggcgggtg | 6600 |
| tggtggttac gcgcagcgtg accgctacac ttgccagcgc cctagcgccc gctcctttcg | 6660 |
| ctttcttccc ttcctttctc gccacgttcg ccggctttcc ccgtcaagct ctaaatcggg | 6720 |
| ggctcccttt agggttccga tttagtgctt tacggcacct cgaccccaaa aaacttgatt | 6780 |
| agggtgatgg ttcacgtagt gggccatcgc cctgatagac ggtttttcgc cctttgacgt | 6840 |
| tggagtccac gttctttaat agtggactct tgttccaaac tggaacaaca ctcaaccta | 6900 |
| tctcggtcta ttcttttgat ttataaggga ttttgccgat tcggcctat tggttaaaaa | 6960 |
| atgagctgat ttaacaaaaa tttaacgcga attaattctg tggaatgtgt gtcagttag | 7019 |

<210> SEQ ID NO 41
<211> LENGTH: 2272
<212> TYPE: DNA
<213> ORGANISM: Artificial
<220> FEATURE:
<223> OTHER INFORMATION: Synthetic construct

<400> SEQUENCE: 41

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgc cccattgacg caaatgggcg gtaggcgtgt | 540 |
| acggtgggag gtctatataa gcagagctca tgatagaagc actctactat cgtcgaccg | 600 |
| atcctgagaa cttcagggtg agtttgggga cccttgattg ttcttctttt tcgctattg | 660 |
| taaaattcat gttatatgga gggggcaaag ttttcagggt gttgtttaga atgggaagat | 720 |
| gtcccttgta tcaccatgga ccctcatgat aattttgttt cttcactttt ctactctgtt | 780 |
| gacaaccatt gtctcctctt attttctttt cattttctgt aacttttctcg ttaaacttta | 840 |
| gcttgcattt gtaacgaatt tttaaattca cttttgttta tttgtcagat tgtaagtact | 900 |
| ttctctaatc acttttttt caaggcaatc agggtatatt atattgtact tcagcacagt | 960 |
| tttagagaac aattgttata attaaatgat aaggtagaat atttctgcat ataaattctg | 1020 |
| gctggcgtgg aaatattctt attggtagaa acaactacac cctggtcatc atcctgcctt | 1080 |
| tctctttatg gttacaatga tatacactgt ttgagatgag gataaaatac tctgagtcca | 1140 |
| aaccggccc ctctgctaac catgttcatg ccttcttctc tttcctacag ctcctgggca | 1200 |
| acgtgctggt tgttgtgctg tctcatcatt ttggcaaaga attaagctta tactcgagct | 1260 |
| ctagattggg aacccgggtc tctcgaattc gagatctcca ccatgcacag acctagacgt | 1320 |

```
cgtggaactc gtccacctcc actggcactg ctcgctgctc tcctcctggc tgcacgtggt   1380
gctgatgcag acatccagat gacccagtct ccatcctccc tgtctgcatc tgtaggagac   1440
agagtcacca tcacttgccg ggcgagtcag ggcattagcg attatttagc ctggtatcag   1500
cagaaaccag gaaagttcc taacctcctg atctatgctg cgtccgcttt acaatcaggg   1560
gtcccatctc gtttcagtgg cagtggatct gggacagatt tcactctcac catcagcagc   1620
ctgcagcctg aggatgttgc aacttattac tgtcaaaatt ataacactgc cccgctcact   1680
ttcggcgggg ggaccaaggt ggaaatcaaa cgaactgtgg ctgcaccatc tgtcttcatc   1740
ttcccgccat ctgatgagca gttgaaatct ggaactgcct ctgttgtgtg cctgctgaat   1800
aacttctatc ccagagaggc caaagtacag tggaaggtgg ataacgccct ccaatcgggt   1860
aactcccagg agagtgtcac agagcaggac agcaaggaca gcacctacag cctcagcagc   1920
accctgacgc tgagcaaagc agactacgag aaacacaaag tctacgcctg cgaagtcacc   1980
catcagggcc tgagctcgcc cgtcacaaag agcttcaaca ggggagagtg ttaggcggcc   2040
gctaatcagc cataccacat tgtagaggt tttacttgct ttaaaaaacc tcccacacct   2100
ccccctgaac ctgaaacata aaatgaatgc aattgttgtt gttaacttgt ttattgcagc   2160
ttataatggt tacaaataaa gcaatagcat cacaaatttc acaaataaag catttttttc   2220
actgcattct agttgtggtt tgtccaaact catcaatgta tcttatcatg tc           2272
```

<210> SEQ ID NO 42
<211> LENGTH: 6335
<212> TYPE: DNA
<213> ORGANISM: Artificial
<220> FEATURE:
<223> OTHER INFORMATION: Synthetic plasmid

<400> SEQUENCE: 42

```
tcgagctcta gattgggaac ccgggtctct cgaattcgag atctccacca tgcacagacc     60
tagacgtcgt ggaactcgtc cacctccact ggcactgctc gctgctctcc tcctggctgc    120
acgtggtgct gatgcagaca tccagatgac ccagtctcca tcctccctgt ctgcatctgt    180
aggagacaga gtcaccatca cttgccgggc gagtcagggc attagcgatt atttagcctg    240
gtatcagcag aaaccaggga agttcctaa cctcctgatc tatgctgcgt ccgctttaca    300
atcaggggtc ccatctcgtt tcagtggcag tggatctggg acagatttca ctctcaccat    360
cagcagcctg cagcctgagg atgttgcaac ttattactgt caaaattata acactgcccc    420
gctcactttc ggcgggggga ccaaggtgga atcaaacga actgtggctg caccatctgt    480
cttcatcttc cgccatctg atgagcagtt gaaatctgga actgcctctg ttgtgtgcct    540
gctgaataac ttctatccca gagaggccaa agtacagtgg aaggtggata acgccctcca    600
atcgggtaac tcccaggaga gtgtcacaga gcaggacagc aaggacagca cctacagcct    660
cagcagcacc ctgacgctga gcaaagcaga ctacgagaaa cacaaagtct acgcctgcga    720
agtcacccat cagggcctga gctcgcccgt cacaaagagc ttcaacaggg gagagtgtta    780
ggcggccgct aatcagccat accacatttg tagaggtttt acttgcttta aaaaacctcc    840
cacacctccc cctgaacctg aaacataaaa tgaatgcaat tgttgttgtt aacttgttta    900
ttgcagctta atggttac aaataaagca atagcatcac aaatttcaca aataaagcat    960
ttttttcact gcattctagt tgtggtttgt ccaaactcat caatgtatct tatcatgtct   1020
accggtaggg cccctctctt catgtgagca aaaggccagc aaaaggccag gaaccgtaaa   1080
```

```
aaggccgcgt tgctggcgtt tttccatagg ctccgccccc ctgacgagca tcacaaaaat   1140
cgacgctcaa gtcagaggtg gcgaaacccg acaggactat aaagatacca ggcgtttccc   1200
cctggaagct ccctcgtgcg ctctcctgtt ccgaccctgc cgcttaccgg atacctgtcc   1260
gcctttctcc cttcgggaag cgtggcgctt tctcaatgct cacgctgtag gtatctcagt   1320
tcggtgtagg tcgttcgctc caagctgggc tgtgtgcacg aaccccccgt tcagcccgac   1380
cgctgcgcct tatccggtaa ctatcgtctt gagtccaacc cggtaagaca cgacttatcg   1440
ccactggcag cagccactgg taacaggatt agcagagcga ggtatgtagg cggtgctaca   1500
gagttcttga agtggtggcc taactacggc tacactagaa ggacagtatt tggtatctgc   1560
gctctgctga agccagttac cttcggaaaa agagttggta gctcttgatc cggcaaacaa   1620
accaccgctg gtagcggtgg ttttttttgtt tgcaagcagc agattacgcg cagaaaaaaa   1680
ggatctcaag aagatccttt gatctttttct acggggtctg acgctcagtg gaacgaaaac   1740
tcacgttaag ggattttggt catgggcgcg gcatgagat tatcaaaaag gatcttcacc   1800
tagatccttt taaattaaaa atgaagtttt aaatcaatct aaagtatata tgagtaaact   1860
tggtctgaca gttaccaatg cttaatcagt gaggcaccta tctcagcgat ctgtctattt   1920
cgttcatcca tagttgcctg actccccgtc gtgtagataa ctacgatacg ggagggctta   1980
ccatctggcc ccagtgctgc aatgataccg cgagacccac gctcaccggc tccagattta   2040
tcagcaataa accagccagc cggaagggcc gagcgcagaa gtggtcctgc aactttatcc   2100
gcctccatcc agtctattaa ttgttgccgg gaagctagag taagtagttc gccagttaat   2160
agtttgcgca acgttgttgc cattgctaca ggcatcgtgg tgtcacgctc gtcgtttggt   2220
atggcttcat tcagctccgg ttcccaacga tcaaggcgag ttacatgatc ccccatgttg   2280
tgcaaaaaag cggttagctc cttcggtcct ccgatcgttg tcagaagtaa gttggccgca   2340
gtgttatcac tcatggttat ggcagcactg cataattctc ttactgtcat gccatccgta   2400
agatgctttt ctgtgactgg tgagtactca accaagtcat tctgagaata gtgtatgcgg   2460
cgaccgagtt gctcttgccc ggcgtcaata cgggataata ccgcgccaca tagcagaact   2520
ttaaaagtgc tcatcattgg aaaacgttct cggggcgaaa actctcaag gatcttaccg   2580 ctgttgagat ccagttcgat gtaacccact cgtgcaccca actgatcttc agcatctttt   2640
actttcacca gcgtttctgg gtgagcaaaa acaggaaggc aaaatgccgc aaaaaaggga   2700
ataagggcga cacggaaatg ttgaatactc atactcttcc tttttcaata ttattgaagc   2760
atttatcagg gttattgtct catgagcgga tacatatttg aatgtattta gaaaaataaa   2820
caaatagggg ttccgcgcac atttccccga aaagtgccac ctgacgtcag gtacacttag   2880
gcgcgccatt agagttcctg caggctacat ggtaccaagc ctaggcctcc aaaaaagcct   2940
cctcactact tctggaatag ctcagaggca gaggcggcct cggcctctgc ataaataaaa   3000
aaaattagtc agccatgggg cggagaatgg gcggaactgg gcggagttag ggcgggatg    3060 ggcggagtta ggggcgggac tatggttgct gactaattga gatgcatgct ttgcatactt   3120
ctgcctgctg gggagcctgg ggactttcca cacctggttg ctgactaatt gagatgcatg   3180
ctttgcatac ttctgcctgc tggggagcct ggggactttc acaccggat ccaccatgga    3240 tagatccgga aagcctgaac tcaccgcgac gtctgtcgag aagtttctga tcgaaaagtt   3300
cgacagcgtc tccgacctga tgcagctctc ggagggcgaa gaatctcgtg ctttcagctt   3360
cgatgtagga gggcgtggat atgtcctgcg ggtaaatagc tgcgccgatg gtttctacaa   3420
agatcgttat gtttatcggc actttgcatc ggccgcgctc ccgattccgg aagtgcttga   3480
```

```
cattggggag ttcagcgaga gcctgaccta ttgcatctcc cgccgtgcac agggtgtcac   3540
gttgcaagac ctgcctgaaa ccgaactgcc cgctgttctg cagccggtcg cggaggccat   3600
ggatgcgatc gctgcggccg atcttagcca gacgagcggg ttcggcccat tcggaccgca   3660
aggaatcggt caatacacta catggcgtga tttcatatgc gcgattgctg atccccatgt   3720
gtatcactgg caaactgtga tggacgacac cgtcagtgcg tccgtcgcgc aggctctcga   3780
tgagctgatg ctttgggccg aggactgccc gaagtccgg cacctcgtgc acgcggattt   3840
cggctccaac aatgtcctga cggacaatgg ccgcataaca gcggtcattg actggagcga   3900
ggcgatgttc ggggattccc aatacgaggt cgccaacatc ttcttctgga ggccgtggtt   3960
ggcttgtatg gagcagcaga cgcgctactt cgagcggagg catccggagc ttgcaggatc   4020
gccgcggctc cgggcgtata tgctccgcat tggtcttgac caactctatc agagcttggt   4080
tgacggcaat ttcgatgatg cagcttgggc gcagggtcga tgcgacgcaa tcgtccgatc   4140
cggagccggg actgtcgggc gtacacaaat cgcccgcaga agcgcggccg tctggaccga   4200
tggctgtgta aagtactcg ccgatagtgg aaaccgacgc cccagcactc gtccgagggc   4260
aaaggaatag acgcgtgctg taagtctgca gaaattgatg atctattaaa caataaagat   4320
gtccactaaa atggaagttt ttcctgtcat actttgttaa aagggtgag aacagagtac   4380 ctacattttg aatggaagga ttggagctac ggggtgggg gtggggtggg attagataaa   4440
tgcctgctct ttactgaagg ctctttacta ttgctttatg ataatgtttc atagttggat   4500
atcataattt aaacaagcaa aaccaaatta agggccagct cattcctccc actcatgatc   4560
tatggatcta tagatctctc gtgcagctgg ggctctaggg ggtatcccca cgcgccctgt   4620
agcggcgcat taagcgcggc gggtgtggtg gttacgcgca gcgtgaccgc tacacttgcc   4680
agcgccctag cgcccgctcc tttcgctttc ttcccttcct ttctcgccac gttcgccggc   4740
tttccccgtc aagctctaaa tcggggctc cctttagggt tccgatttag tgctttacgg   4800
cacctcgacc ccaaaaaact tgattagggt gatggttcac gtagtgggcc atcgccctga   4860
tagacggttt ttcgcccttt gacgttggag tccacgttct ttaatagtgg actcttgttc   4920
caaactggaa caacactcaa ccctatctcg gtctattctt ttgatttata agggattttg   4980
ccgatttcgg cctattggtt aaaaaatgag ctgatttaac aaaaatttaa cgcgaattaa   5040
ttctgtggaa tgtgtgtcag ttagtcgcga tgtgtgacta gttagttatt aatagtaatc   5100
aattacgggg tcattagttc atagcccata tatggagttc cgcgttacat aacttacggt   5160
aaatggcccg cctggctgac cgcccaacga ccccgccca ttgacgtcaa taatgacgta   5220
tgttcccata gtaacgccaa tagggacttt ccattgacgt caatgggtgg agtatttacg   5280
gtaaactgcc cacttggcag tacatcaagt gtatcatatg ccaagtacgc ccctattga   5340 cgtcaatgac ggtaaatggc ccgcctggca ttatgcccag tacatgacct tatgggactt   5400
tcctacttgg cagtacatct acgtattagt catcgctatt accatggtga tgcggttttg   5460
gcagtacatc aatgggcgtg atagcggttt gactcacgg gatttccaa gtctccaccc   5520 cattgacgtc aatgggagtt tgttttggca ccaaaatcaa cgggactttc caaaatgtcg   5580
taacaactcc gccccattga cgcaaatggg cggtaggcgt gtacggtggg aggtctatat   5640
aagcagagct catgatagaa gcactctact attcgtcgac cgatcctgag aacttcaggg   5700
tgagtttggg gacccttgat tgttcttcct ttttcgctat tgtaaaattc atgttatatg   5760
gagggggcaa agttttcagg gtgttgttta gaatgggaag atgtcccttg tatcaccatg   5820
```

```
gaccctcatg ataattttgt ttctttcact ttctactctg ttgacaacca ttgtctcctc    5880
ttattttctt ttcattttct gtaacttttt cgttaaactt tagcttgcat ttgtaacgaa    5940
tttttaaatt cacttttgtt tatttgtcag attgtaagta ctttctctaa tcactttttt    6000
ttcaaggcaa tcagggtata ttatattgta cttcagcaca gttttagaga acaattgtta    6060
taattaaatg ataaggtaga atatttctgc atataaattc tggctggcgt ggaaatattc    6120
ttattggtag aaacaactac accctggtca tcatcctgcc tttctcttta tggttacaat    6180
gatatacact gtttgagatg aggataaaat actctgagtc caaaccgggc ccctctgcta    6240
accatgttca tgccttcttc tctttcctac agctcctggg caacgtgctg gttgttgtgc    6300
tgtctcatca ttttggcaaa gaattaagct tatac                               6335
```

<210> SEQ ID NO 43
<211> LENGTH: 115
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: Xaa can be any naturally occurring amino acid
<220> FEATURE:
<221> NAME/KEY: MISC_FEATURE
<222> LOCATION: (34)..(35)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa can be any naturally occurring amino acid
<220> FEATURE:
<221> NAME/KEY: MISC_FEATURE
<222> LOCATION: (96)..(96)
<223> OTHER INFORMATION: Xaa can be any naturally occurring amino acid
<220> FEATURE:
<221> NAME/KEY: MISC_FEATURE
<222> LOCATION: (100)..(100)
<223> OTHER INFORMATION: Xaa can be any naturally occurring amino acid
<220> FEATURE:
<221> NAME/KEY: MISC_FEATURE
<222> LOCATION: (111)..(111)
<220> FEATURE:
<221> NAME/KEY: MISC_FEATURE
<222> LOCATION: (114)..(114)
<223> OTHER INFORMATION: Xaa can be any naturally occurring amino acid

<400> SEQUENCE: 43

Xaa Asp Val Trp Gly Gln Gly Thr Thr Val Xaa Val Ser Ser Ala Ser
1               5                   10                  15

Thr Lys Gly Pro Ser Val Phe Pro Leu Ala Pro Xaa Ser Xaa Ser Thr
            20                  25                  30

Ser Xaa Xaa Thr Ala Ala Leu Gly Cys Leu Val Lys Asp Tyr Phe Pro
        35                  40                  45

Glu Pro Val Thr Val Ser Trp Asn Ser Gly Ala Leu Thr Ser Gly Val
    50                  55                  60

```
His Thr Phe Pro Ala Val Leu Gln Ser Ser Gly Leu Tyr Ser Leu Ser
 65                  70                  75                  80

Ser Val Val Thr Val Pro Ser Ser Leu Gly Thr Xaa Thr Tyr Xaa
                 85                  90                  95

Cys Asn Val Xaa His Lys Pro Ser Asn Thr Lys Val Asp Lys Xaa Val
            100                 105                 110

Glu Xaa Lys
        115

<210> SEQ ID NO 44
<211> LENGTH: 225
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: Xaa can be any naturally occurring amino acid
<220> FEATURE:
<221> NAME/KEY: MISC_FEATURE
<222> LOCATION: (53)..(53)
<223> OTHER INFORMATION: Xaa can be any naturally occurring amino acid
<220> FEATURE:
<221> NAME/KEY: MISC_FEATURE
<222> LOCATION: (75)..(75)
<223> OTHER INFORMATION: Xaa can be any naturally occurring amino acid
<220> FEATURE:
<221> NAME/KEY: MISC_FEATURE
<222> LOCATION: (106)..(106)
<223> OTHER INFORMATION: Xaa can be any naturally occurring amino acid
<220> FEATURE:
<221> NAME/KEY: MISC_FEATURE
<222> LOCATION: (109)..(110)
<223> OTHER INFORMATION: Xaa can be any naturally occurring amino acid
<220> FEATURE:
<221> NAME/KEY: MISC_FEATURE
<222> LOCATION: (134)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: MISC_FEATURE
<222> LOCATION: (188)..(188)
<223> OTHER INFORMATION: Xaa can be any naturally occurring amino acid
<220> FEATURE:
<221> NAME/KEY: MISC_FEATURE
<222> LOCATION: (198)..(198)
<223> OTHER INFORMATION: Xaa can be any naturally occurring amino acid
<220> FEATURE:
<221> NAME/KEY: MISC_FEATURE
<222> LOCATION: (224)..(224)
<223> OTHER INFORMATION: Xaa can be any naturally occurring amino acid

<400> SEQUENCE: 44

Tyr Gly Pro Pro Cys Pro Pro Cys Pro Ala Pro Glu Xaa Leu Gly Gly
  1               5                  10                  15

Pro Ser Val Phe Leu Phe Pro Pro Lys Pro Lys Asp Thr Leu Met Ile
                 20                  25                  30

Ser Arg Thr Pro Glu Val Thr Cys Val Val Val Asp Val Ser Xaa Glu
             35                  40                  45

Asp Pro Glu Val Xaa Phe Asn Trp Tyr Val Asp Gly Val Glu Val His
         50                  55                  60

Asn Ala Lys Thr Lys Pro Arg Glu Glu Gln Xaa Asn Ser Thr Tyr Arg
```

```
                65                  70                  75                  80
        Val Val Ser Val Leu Thr Val Leu His Gln Asp Trp Leu Asn Gly Lys
                            85                  90                  95
        Glu Tyr Lys Cys Lys Val Ser Asn Lys Xaa Leu Pro Xaa Xaa Ile Glu
                        100                 105                 110
        Lys Thr Ile Ser Lys Ala Lys Gly Gln Pro Arg Glu Pro Gln Val Tyr
                    115                 120                 125
        Thr Leu Pro Pro Ser Xaa Xaa Glu Xaa Thr Lys Asn Gln Val Ser Leu
                130                 135                 140
        Thr Cys Leu Val Lys Gly Phe Tyr Pro Ser Asp Ile Ala Val Glu Trp
        145                 150                 155                 160
        Glu Ser Asn Gly Gln Pro Glu Asn Asn Tyr Lys Thr Thr Pro Pro Val
                        165                 170                 175
        Leu Asp Ser Asp Gly Ser Phe Phe Leu Tyr Ser Xaa Leu Thr Val Asp
                    180                 185                 190
        Lys Ser Arg Trp Gln Xaa Gly Asn Val Phe Ser Cys Ser Val Met His
                195                 200                 205
        Glu Ala Leu His Asn His Tyr Thr Gln Lys Ser Leu Ser Leu Ser Xaa
            210                 215                 220
        Gly
        225

<210> SEQ ID NO 45
<211> LENGTH: 60
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (21)..(22)
<223> OTHER INFORMATION: Xaa can be any naturally occurring amino acid
<220> FEATURE:
<221> NAME/KEY: MISC_FEATURE
<222> LOCATION: (24)..(27)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (34)..(34)
<223> OTHER INFORMATION: Xaa can be any naturally occurring amino acid
<220> FEATURE:
<221> NAME/KEY: MISC_FEATURE
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: MISC_FEATURE
<222> LOCATION: (54)..(54)
<223> OTHER INFORMATION: Xaa can be any naturally occurring amino acid
<220> FEATURE:
<221> NAME/KEY: MISC_FEATURE
<222> LOCATION: (56)..(56)
<223> OTHER INFORMATION: Xaa can be any naturally occurring amino acid
```

```
<400> SEQUENCE: 45

Ser Asp Tyr Leu Ala Trp Tyr Gln Gln Lys Pro Gly Xaa Xaa Pro Xaa
1               5                   10                  15

Leu Leu Ile Tyr Xaa Xaa Ser Xaa Xaa Xaa Xaa Gly Val Pro Xaa Arg
            20                  25                  30

Phe Xaa Gly Ser Gly Ser Gly Thr Asp Phe Thr Leu Thr Ile Ser Xaa
        35                  40                  45

Leu Xaa Pro Glu Asp Xaa Ala Xaa Tyr Tyr Cys Gln
    50                  55                  60

<210> SEQ ID NO 46
<211> LENGTH: 118
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (4)..(4)
<223> OTHER INFORMATION: Xaa can be any naturally occurring amino acid

<400> SEQUENCE: 46

Thr Phe Gly Xaa Gly Thr Lys Val Glu Ile Lys Arg Thr Val Ala Ala
1               5                   10                  15

Pro Ser Val Phe Ile Phe Pro Pro Ser Asp Glu Gln Leu Lys Ser Gly
            20                  25                  30

Thr Ala Ser Val Val Cys Leu Leu Asn Asn Phe Tyr Pro Arg Glu Ala
        35                  40                  45

Lys Val Gln Trp Lys Val Asp Asn Ala Leu Gln Ser Gly Asn Ser Gln
    50                  55                  60

Glu Ser Val Thr Glu Gln Asp Ser Lys Asp Ser Thr Tyr Ser Leu Ser
65                  70                  75                  80

Ser Thr Leu Thr Leu Ser Lys Ala Asp Tyr Glu Lys His Lys Val Tyr
                85                  90                  95

Ala Cys Glu Val Thr His Gln Gly Leu Ser Ser Pro Val Thr Lys Ser
            100                 105                 110

Phe Asn Arg Gly Glu Cys
            115
```

PRODUCTION CELL LINE ENHANCERS

CROSS-REFERENCE TO RELATED APPLICATIONS

This application is a continuation of U.S. application Ser. No. 13/904,587, filed on May 29, 2013, which claims the benefit under 35 U.S.C. § 119(e) of U.S. Provisional Patent Application No. 61/652,549 filed 29 May 2012, which application is herein specifically incorporated by reference in its entirety.

SEQUENCE LISTING

This application incorporates by reference the sequence listing submitted in computer readable form as file 8150A-2_ST25.txt created on Aug. 6, 2013 (206,310 bytes).

FIELD

The invention relates to a cell or cells expressing a recombinant stress-response lectin for the improved production of a multi-subunit protein. Specifically, the invention provides a mammalian cell and cell-line derived therefrom containing a gene encoding EDEM2, and which yields antibody at a high titer.

BACKGROUND

The manufacture of therapeutically active proteins requires proper folding and processing prior to secretion. Proper folding is particularly relevant for proteins, such as antibodies, which consist of multiple subunits that must be properly assembled before secretion. Eukaryotic cells have adapted a system that ensures the proper folding of proteins and the removal of misfolded proteins from the secretory pathway. This system is called the unfolded protein response (UPR) pathway, and it is triggered by the accumulation of misfolded proteins in the endoplasmic reticulum (ER).

An early event of the UPR is the activation of the transcription factor Xbp1, which in turn activates the transcription of endoplasmic reticulum degradation-enhancing alpha-mannosidase-like protein 2 (EDEM2), a member of the endoplasmic reticulum associated degradation (ERAD) pathway. EDEM2 facilitates the removal of misfolded proteins. The ERAD pathway comprises five steps: (1) chaperone-mediated recognition of malformed proteins, (2) targeting of malformed proteins to the retrotranslocation machinery or E3-ligases, which involves EDEM2, (3) initiation of retrotranslocation; (4) ubiquitylation and further retrotranslocation; and (5) proteosome targeting and degradation.

Antibodies are multi-subunit proteins comprising two heavy chains and two light chains, which must be properly folded and associated to form a functional heterotetramer. Any improvement in the efficient and accurate processing of the heavy and light chains to improve the yield or titer of functional antibody heterotetramers is desired.

SUMMARY

Applicants made the surprising discovery that the ectopic expression of EDEM2 in a protein-manufacturing cell line increases the average output of protein per cell, increases the titer of protein secreted into the media, and increases the integrated cell density of production cell lines.

Thus, in one aspect, the invention provides a cell containing (a) a recombinant polynucleotide that encodes a stress-induced mannose-binding lectin and (b) a polynucleotide that encodes a multi-subunit protein. In some embodiments, the stress-induced mannose-binding lectin is an EDEM2 protein, non-limiting examples of which are provided in Table 1, and the multi-subunit protein is an antibody. In other embodiments, the cell also contains a polynucleotide that encodes the active spliced form of XBP1, non-limiting examples of which are provided in Table 2. In one embodiment, the cell is a mammalian cell, such as a CHO cell used in the manufacture of biopharmaceuticals.

In another aspect, the invention provides a cell line derived from the cell described in the previous aspect. By "derived from", what is meant is a population of cells clonally descended from an individual cell and having some select qualities, such as the ability to produce active protein at a given titer, or the ability to proliferate to a particular density. In some embodiments, the cell line, which is derived from a cell harboring the recombinant polynucleotide encoding a stress-induced mannose-binding lectin and a polynucleotide encoding a multi-subunit protein, is capable of producing the multi-subunit protein at a titer of at least 3 grams per liter of media (g/L), at least 5 g/L, or at least 8 g/L. In some embodiments, the cell line can attain an integrated cell density (ICD) that is at least 30% greater, at least 50% greater, at least 60% greater, or at least 90% greater than the integrated cell density attainable by a cell line derived from what is essentially the same cell but without the recombinant polynucleotide encoding the stress-induced mannose-binding lectin.

In another aspect, the invention provides an isolated or recombinant polynucleotide comprising a nucleic acid sequence encoding an EDEM2 protein, which is operably linked (cis) to a constitutive and ubiquitously expressed mammalian promoter, such as the ubiquitin C promoter. In some embodiments, the EDEM2 protein has the amino acid of SEQ ID NO: 8, or an amino acid sequence that is at least 92% identical to any one of SEQ ID NO: 1-7. In some embodiments, the polynucleotide comprises a nucleic acid sequence of SEQ ID NO: 16. In one particular embodiment, the polynucleotide consists of a nucleic acid sequence of SEQ ID NO: 14; and in another particular embodiment, SEQ ID NO: 15.

In another aspect, the invention provides an isolated or recombinant polynucleotide comprising a nucleic acid sequence encoding an XBP1 protein, which is operably linked to (in cis) a constitutive and ubiquitously expressed mammalian promoter, such as the ubiquitin C promoter. In some embodiments, the XBP1 protein has the amino acid of SEQ ID NO: 13, or an amino acid sequence that is at least 86% identical to any one of SEQ ID NO: 9-12. In some embodiments, the polynucleotide comprises a nucleic acid sequence of SEQ ID NO: 18. In one particular embodiment, the polynucleotide consists of a nucleic acid sequence of SEQ ID NO: 17.

In another aspect, the invention provides a cell that contains an EDEM2-encoding polynucleotide, as described in the prior aspect, and a polynucleotide that encodes a multi-subunit protein, such as an antibody. In some embodiments, the cell also contains an XBP1-encoding polynucleotide, as described in the preceding aspect. In one embodiment, the multi-subunit protein is an antibody, and the heavy chain of the antibody comprises an amino acid sequence of SEQ ID NO: 43 and SEQ ID NO: 44, and the light chain of the antibody comprises an amino acid sequence of SEQ ID NO: 45 and SEQ ID NO: 46. In this and several embodiments, each polypeptide subunit of the multi-subunit protein is encoded by a separate polynucleotide. Thus, for example, a polynucleotide encoding an antibody may include a polynucleotide encoding a heavy chain and a polynucleotide encoding a light chain, hence two subunits. In some embodiments, the cell is a chinese hamster ovary (CHO) cell.

In one embodiment, the encoded multi-subunit protein is an anti-GDF8 antibody having a heavy chain variable region amino acid sequence of SEQ ID NO: 20 and a light chain variable region amino acid sequence of SEQ ID NO: 22. In one embodiment, the anti-GDF8 antibody comprises a heavy chain having an amino acid sequence of SEQ ID NO: 19 and a light chain having an amino acid sequence of SEQ ID NO: 21. In one embodiment, the polynucleotide that encodes the heavy chain of the anti-GDF8 antibody comprises a nucleic acid sequence of SEQ ID NO: 23; and the polynucleotide that encodes the light chain of the anti-GDF8 antibody comprises a nucleic acid sequence of SEQ ID NO: 25. In one embodiment, the polynucleotide that encodes the heavy chain of the anti-GDF8 antibody consists of a nucleic acid sequence of SEQ ID NO: 24; and the polynucleotide that encodes the light chain of the anti-GDF8 antibody consists of a nucleic acid sequence of SEQ ID NO: 25.

In another embodiment, the encoded multi-subunit protein is an anti-ANG2 antibody having a heavy chain variable region amino acid sequence of SEQ ID NO: 28 and a light chain variable region amino acid sequence of SEQ ID NO: 30. In one embodiment, the anti-ANG2 antibody comprises a heavy chain having an amino acid sequence of SEQ ID NO: 27 and a light chain having an amino acid sequence of SEQ ID NO: 29. In one embodiment, the polynucleotide that encodes the heavy chain of the anti-ANG2 antibody comprises a nucleic acid sequence of SEQ ID NO: 31; and the polynucleotide that encodes the light chain of the anti-ANG2 antibody comprises a nucleic acid sequence of SEQ ID NO: 33. In one embodiment, the polynucleotide that encodes the heavy chain of the anti-ANG2 antibody consists of a nucleic acid sequence of SEQ ID NO: 32; and the polynucleotide that encodes the light chain of the anti-ANG2 antibody consists of a nucleic acid sequence of SEQ ID NO: 34.

In another embodiment, the encoded multi-subunit protein is an anti-ANGPTL4 antibody having a heavy chain variable region amino acid sequence of SEQ ID NO: 36 and a light chain variable region amino acid sequence of SEQ ID NO: 38. In one embodiment, the anti-ANGPTL4 antibody comprises a heavy chain having an amino acid sequence of SEQ ID NO: 35 and a light chain having an amino acid sequence of SEQ ID NO: 37. In one embodiment, the polynucleotide that encodes the heavy chain of the anti-ANGPTL4 antibody comprises a nucleic acid sequence of SEQ ID NO: 39; and the polynucleotide that encodes the light chain of the anti-ANGPTL4 antibody comprises a nucleic acid sequence of SEQ ID NO: 41. In one embodiment, the polynucleotide that encodes the heavy chain of the anti-ANGPTL4 antibody consists of a nucleic acid sequence of SEQ ID NO: 40; and the polynucleotide that encodes the light chain of the anti-ANGPTL4 antibody consists of a nucleic acid sequence of SEQ ID NO: 42.

In another aspect, the invention provides a method of manufacturing a multi-subunit protein, by culturing a cell of the previous aspect in a medium, wherein the multi-subunit protein is synthesized in the cell and subsequently secreted into the medium. In some embodiments, the multi-subunit protein is an antibody, such as for example anti-GDF8, anti-ANG2, anti-ANGPTL4, or an antibody having a heavy chain sequence of SEQ ID NO: 43 and 44, and a light chain sequence of SEQ ID NO: 45 and 46. In some embodiments, the multi-subunit protein attains a titer of at least 3 g/L, at least 5 g/L, at least 6 g/L, or at least 8 g/L. In some embodiments, the cell proliferates in the medium and establishes an integrated cell density of about $\geq 5 \times 10^7$ cell-day/mL, about $\geq 1 \times 10^8$ cell-day/mL, or about $\geq 1.5 \times 10^8$ cell-day/mL.

In another aspect, the invention provides a multi-subunit protein, which is manufactured according to the method described in the preceding aspect. In one embodiment, the manufactured protein is an antibody. In some embodiments, the antibody consists of a heavy chain, which comprises an amino acid sequence of SEQ ID NO: 43 and SEQ ID NO: 44, and a light chain, which comprises an amino acid sequence of SEQ ID NO: 45 and SEQ ID NO: 46. In one specific embodiment, the manufactured multi-subunit protein is an anti-GDF8 antibody having a heavy chain variable region amino acid sequence of SEQ ID NO: 20 and a light chain variable region amino acid sequence of SEQ ID NO: 22. In another specific embodiment, the manufactured multi-subunit protein is an anti-ANG2 antibody having a heavy chain variable region amino acid sequence of SEQ ID NO: 28 and a light chain variable region amino acid sequence of SEQ ID NO: 30. In yet another specific embodiment, the manufactured multi-subunit protein is an anti-ANGPTL4 antibody having a heavy chain variable region amino acid sequence of SEQ ID NO: 36 and a light chain variable region amino acid sequence of SEQ ID NO: 38.

DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference in their entirety.

As used herein, the term "recombinant polynucleotide", which is used interchangeably with "isolated polynucleotide", means a nucleic acid polymer such as a ribonucleic acid or a deoxyribonucleic acid, either single stranded or double stranded, originating by genetic engineering manipulations. A recombinant polynucleotide may be a circular plasmid or a linear construct existing in vitro or within a cell as an episome. A recombinant polynucleotide may be a construct that is integrated within a larger polynucleotide molecule or supermolecular structure, such as a linear or circular chromosome. The larger polynucleotide molecule or supermolecular structure may be within a cell or within the nucleus of a cell. Thus, a recombinant polynucleotide may be integrated within a chromosome of a cell.

As used herein, the term "stress-induced mannose-binding lectin" refers to a mannose-binding protein, which means a protein that binds or is capable of binding mannose, derivatives of mannose, such as mannose-6-phosphate, or a glycoprotein that expresses mannose or a mannose derivative in its glycocalyx; and whose activity is upregulated during stress. Cellular stress includes inter alia starvation, DNA damage, hypoxia, poisoning, shear stress and other mechanical stresses, tumor stress, and the accumulation of misfolded proteins in the endoplasmic reticulum. Exemplary stress-induced mannose-binding lectins include the EDEM proteins EDEM1, EDEM2 and EDEM3, Yos 9, OS9, and XTP3-B (see Vembar and Brodsky, Nat. Rev. Mol. Cell. Biol. 9(12): 944-957, 2008, and references cited therein).

As used herein, the term "EDEM2" means any ortholog, homolog, or conservatively substituted variant of endoplasmic reticulum degradation-enhancing alpha-mannosidase-like protein. EDEM2 proteins are generally known in the art to be involved in endoplasmic reticulum-associated degradation (ERAD), being up-regulated by Xbp-1 and facilitating the extraction of misfolded glycoproteins from the calnexin cycle for removal. (See Mast et al., Glycobiology 15(4): 421-436, 2004; Olivari and Molinari, FEBS Lett. 581: 3658-3664, 2007; Olivari et al., J. Biol. Chem. 280(4): 2424-2428, 2005; and Vembar and Brodsky 2008, which are herein incorporated by reference.) Exemplary EDEM2 sequences are depicted in Table 1, which is cross-referenced to the Sequence Listing.

TABLE 1

| Animal | SEQ ID NO: | % id human | % id mouse | % id hamster |
|---|---|---|---|---|
| Mouse | 1 | 93 | 100 | 96 |
| Rat | 2 | 94 | 98 | 96 |
| Hamster | 3 | 93 | 96 | 100 |
| Human | 4 | 100 | 93 | 93 |
| Chimpanzee | 5 | 99 | 94 | 93 |
| Orangutan | 6 | 97 | 92 | 92 |
| Zebra fish | 7 | 69 | 70 | 69 |
| Consensus | 8 | 100 | 100 | 100 |

As used herein, the term "Xbp1", also known as XBP1 or X-box binding protein 1, means any ortholog, homolog, or conservatively substituted variant of Xbp1. Xbp1 is a transcription factor and functional element of the UPR. ER stress activates both (1) the transcription factor ATF6, which in turn upregulates the transcription of Xbp1 mRNA, and (2) the ER membrane protein IRE1, which mediates the splicing of the precursor Xbp1 mRNA to produce active Xbp1. As mentioned above, activated Xbp1 in turn upregulates the activity of EDEM2. (See Yoshida et al., Cell Structure and Function 31(2): 117-125, 2006; and Olivari, 2005.) Exemplary Xbp1 amino acid sequences are depicted in Table 2, which is cross-referenced to the Sequence Listing.

TABLE 2

| Animal | SEQ ID NO | % id human | % id mouse | % id hamster |
|---|---|---|---|---|
| Mouse | 9 | 86 | 100 | 92 |
| Hamster | 10 | 86 | 92 | 100 |
| Human | 11 | 100 | 86 | 86 |
| Zebra fish | 12 | 47 | 47 | 48 |
| Consensus | 13 | 100 | 100 | 100 |

As used herein, the term "antibody" is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody". Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. An "isolated antibody" or "purified antibody" may be substantially free of other cellular material or chemicals.

The term "specifically binds", or the like, means that an antibody or antigen-binding fragment thereof forms a complex with an antigen that is relatively stable under physiologic conditions. Specific binding can be characterized by a dissociation constant of at least about $1\times10^{-6}$ M or greater. Methods for determining whether two molecules specifically bind are well known in the art and include, for example, equilibrium dialysis, surface plasmon resonance, and the like. An isolated antibody that specifically binds human GDF8 (for example) may, however, have cross-reactivity to other antigens, such as GDF8 molecules from other species (orthologs).

Various antibodies are used as examples of multi-subunit proteins secreted by cells harboring the polynucleotide encoding a stress-induced mannose-binding lectin. Those examples include anti-GDF8, anti-ANG2, and anti-ANGPTL4 antibodies. These and similar antibodies are described in US Pat. Apps. No. 20110293630, 20110027286, and 20110159015 respectively, which are incorporated herein by reference.

As used herein, the term "cell" refers to a prokaryotic or eukaryotic cell capable of replicating DNA, transcribing RNA, translating polypeptides, and secreting proteins. Cells include animal cells used in the commercial production of biological products, such as insect cells (e.g., Schneider cells, Sf9 cells, Sf21 cells, Tn-368 cells, BTI-TN-5B1-4 cells; see Jarvis, Methods Enzymol. 463: 191-222, 2009; and Potter et al., Int. Rev. Immunol. 10(2-3): 103-112, 1993) and mammalian cells (e.g., CHO or CHO-K1 cells, COS or COS-7 cells, HEK293 cells, PC12 cells, HeLa cells, Hybridoma cells; Trill et al., Curr. Opin. Biotechnol. 6(5): 553-560, 1995; Kipriyanov and Little, Mo. Biotechnol. 12(2): 173-201, 1999). In one embodiment, the cell is a CHO-K1 cell containing the described UPR pathway polynucleotides. For a description of CHO-K1 cells, see also Kao et al., Proc. Nat'l. Acad. Sci. USA 60: 1275-1281, 1968.

As used herein, the term "promoter" means a genetic sequence generally in cis and located upstream of a protein coding sequence, and which facilitates the transcription of the protein coding sequence. Promoters can be regulated (developmental, tissue specific, or inducible (chemical, temperature)) or constitutively active. In certain embodiments, the polynucleotides that encode proteins are operably linked to a constitutive promoter. By "operably linked", what is meant is that the protein-encoding polynucleotide is located three-prime (downstream) and cis of the promoter, and under control of the promoter. In certain embodiments, the promoter is a constitutive mammalian promoter, such as the ubiquitin C promoter (see Schorpp et al., Nucl. Acids Res. 24(9): 1787-1788, 1996); Byun et al., Biochem. Biophys. Res. Comm. 332(2): 518-523, 2005) or the CMV-IE promoter (see Addison et al., J. Gen. Virol. 78(7): 1653-1661, 1997; Hunninghake et al., J. Virol. 63(7): 3026-3033, 1989), or the hCMV-IE promoter (human cytomegalovirus immediate early gene promoter) (see Stinski & Roehr, J. Virol. 55(2): 431-441, 1985; Hunninghake et al., J. Virol. 63(7): 3026-3033, 1989).

As used herein, the phrase "integrated cell density", or "ICD" means the density of cells in a culture medium taken as an integral over a period of time, expressed as cell-days per mL. In some embodiments, the ICD is measured around the twelfth day of cells in culture.

As used herein, the term "culture" means both (1) the composition comprising cells, medium, and secreted multi-subunit protein, and (2) the act of incubating the cells in medium, regardless of whether the cells are actively dividing or not. Cells can be cultured in a vessel as small as a 25 mL flask or smaller, and as large as a commercial bioreactor of 10,000 liters or larger. "Medium" refers to the culture medium, which comprises inter alia nutrients, lipids, amino acids, nucleic acids, buffers and trace elements to allow the growth, proliferation, or maintenance of cells, and the production of the multi-subunit protein by the cells. Cell culture media include serum-free and hydrolysate-free defined media as well as media supplemented with sera (e.g., fetal bovine serum (FBS)) or protein hydrolysates. Non-limiting examples of media, which can be commercially acquired, include RPMI medium 1640, Dulbecco's Modified Eagle Medium (DMEM), DMEM/F12 mixture, F10 nutrient mixture, Ham's F12 nutrient mixture, and minimum essential media (MEM).

As used herein, the phrase "conservatively substituted variant", as applied to polypeptides, means a polypeptide having an amino acid sequence with one of more conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-45, herein incorporated by reference. A "moderately conservative" replacement is any change having a nonnegative value in the PAM250 log-likelihood matrix.

Embodiments—The Cell

In one aspect, the invention provides a cell useful in the production of a protein having therapeutic or research utility. In some embodiments, the protein consists of multiple subunits, which must be properly folded and assembled to produce sufficient quantities of active protein. Antibodies are an example of multi-subunit proteins having therapeutic or research utility. In some embodiments, the cell harbors a recombinant genetic construct (i.e., a polynucleotide) that encodes one or more of the individual subunits of the multi-subunit protein. In other embodiments, the genetic construct encoding the individual polypeptide subunits is naturally occurring, such as for example the nucleic acid sequences encoding the subunits of an antibody in a B cell.

To facilitate the proper assembly and secretion of the multi-subunit protein, the cell contains a recombinant polynucleotide that encodes a stress-induced mannose-binding lectin, which in some embodiments is a component of the ERAD. In some embodiments, the stress-induced mannose-binding lectin is an endoplasmic reticulum degradation-enhancing alpha-mannosidase-like protein 2 (EDEM2). It is envisioned that any encoded EDEM2 or conservatively-substituted variant can be successfully employed in the instant invention. Table 1 lists some examples of vertebrate EDEM2 proteins. A multiple pairwise comparison of those protein sequences, which was performed using the Clustal W program of Thompson et al., Nucl. Acids Rev. 22(22): 4673-80, 1994 (see also Yuan et al., Bioinformatics 15(10): 862-3, 1999), revealed that each of the disclosed EDEM2 polynucleotide sequences is at least 69% identical to each other EDEM2 sequence. A Clustal W comparison of the disclosed mammalian EDEM2 sequences revealed that each sequence is at least 92% identical to the other. Thus, in some embodiments, the cell contains a polynucleotide that encodes an EDEM2 polypeptide having a sequence that is at least 92% to any one of a mammalian EDEM2. A consensus EDEM2 amino acid sequence was built by aligning a mouse, rat, hamster, chimpanzee, and human EDEM2 polypeptide amino acid sequences. That consensus sequence is depicted as SEQ ID NO: 8. Thus, in some embodiments, the cell contains a polynucleotide that encodes an EDEM2 polypeptide having an amino acid sequence of SEQ ID NO: 8.

In various embodiments, the cell contains a recombinant polynucleotide that encodes an EDEM2 polypeptide having an amino acid sequence that is at least 92% identical to the mouse EDEM2 (mEDEM2) amino acid sequence; and in a particular embodiment, the polypeptide is mEDEM2 or a conservatively substituted variant thereof.

In some embodiments, the multi-subunit protein is an antibody, and the cell contains a polynucleotide encoding any one or more of a polypeptide comprising an amino acid sequence of SEQ ID NO: 43, SEQ ID NO: 44, SEQ ID NO: 45, and SEQ ID NO: 46. SEQ ID NO: 43 and 44 each represent consensus sequences of the roughly N-terminal and C-terminal portions, respectively, of particular antibody heavy chains. Thus, the polynucleotide encoding a protein subunit in one embodiment encodes a polypeptide comprising both SEQ ID NO: 43 and SEQ ID NO: 44. SEQ ID NO: 45 and 46 each represent consensus sequences of the roughly N-terminal and C-terminal portions, respectively, of particular antibody light chains. Thus, the polynucleotide encoding a protein subunit in one embodiment encodes a polypeptide comprising both SEQ ID NO: 45 and SEQ ID NO: 46. In some embodiments, in addition to the recombinant polynucleotide encoding the EDEM2 protein, the cell contains at least two polynucleotides, each of which encodes a particular subunit of the multi-subunit protein. For example, and as exemplified below, the cell contains a polynucleotide encoding an antibody heavy chain comprising an amino acid sequence of SEQ ID NO: 43 and SEQ ID NO: 44, and another polynucleotide encoding an antibody light chain comprising an amino acid sequence of SEQ ID NO: 45 and SEQ ID NO: 46.

In some embodiments, the cell, in addition to containing the stress-response polynucleotide and one or more polynucleotides encoding a polypeptide subunit, as described above, also contains a polynucleotide that encodes an unfolded protein response transcription factor that operates upstream of EDEM2. The upstream transcription factor is in some cases the spliced form of an XBP1. It is envisioned that any encoded XBP1 can be successfully employed in the instant invention. Table 2 lists some examples of sequences of vertebrate XBP1 spliced-form polypeptides. A multiple pairwise comparison of those polypeptide sequences, which was performed using Clustal W (Thompson 1994; Yuan 1999), revealed that each of the disclosed spliced XBP1 polynucleotide sequences is at least 48% identical to each other XBP1 sequence. A Clustal W comparison of the disclosed mammalian XBP1 sequences revealed that each sequence is at least 86% identical to the other. Thus, in some embodiments, the cell contains a polynucleotide that encodes a spliced-form of an XBP1 polypeptide having a sequence that is at least 86% to any one of a mammalian spliced XBP1. A consensus XBP1 amino acid sequence was built by aligning a mouse, hamster, and human XBP1 amino acid sequences. That consensus sequence is depicted as SEQ ID NO: 13. Thus, in some embodiments, the cell contains a polynucleotide that encodes an XBP1 polypeptide having an amino acid sequence of SEQ ID NO: 13.

In various embodiments, the cell contains a polynucleotide that encodes an XBP1 polypeptide having an amino acid sequence that is at least 86% identical to the mouse XBP1 (mXBP1) amino acid sequence (SEQ ID NO: 9); and in a particular embodiment, the polypeptide is mXBP1, or a conservatively substituted variant thereof.

The invention envisions that any cell may be used to harbor the lectin-encoding polypeptide for the production of a properly folded and active multi-subunit protein. Such cells include the well-known protein production cells such as the bacterium *Escherichia coli* and similar prokaryotic cells, the yeasts *Pichia pastoris* and other *Pichia* and non-pichia yeasts, plant cell explants, such as those of *Nicotiana*, insect cells, such as Schneider 2 cells, Sf9 and Sf21, and the *Trichoplusia ni*-derived High Five cells, and the mammalian cells typically used in bioproduction, such as CHO, CHO-K1, COS, HeLa, HEK293, Jurkat, and PC12 cells. In some embodiments, the cell is a CHO-K1 or a modified CHO-K1 cell such as that which is taught in U.S. Pat. Nos. 7,435,553, 7,514,545, and 7,771,997, as well as U.S. Published Patent Application No. US 2010-0304436 A1, each of which is incorporated herein by reference in its entirety.

In some particular embodiments, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence that encodes a polypeptide comprising the amino acid sequences of SEQ ID NO: 43 and 44, and (4) an antibody light chain-encoding polynucleotide comprising a nucleotide sequence that encodes a polypeptide comprising the amino acid sequences of SEQ ID NO: 45 and 46.

In one particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO:18, (3) an antibody heavy chain-encoding polynucleotide comprising a nucleotide sequence of SEQ ID NO: 23, and (4) an antibody light chain-encoding polynucleotide comprising a nucleotide sequence of SEQ ID NO: 25.

In another particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 31, and (4) an antibody light chain-encoding polynucleotide comprising a nucleotide sequence of SEQ ID NO: 33.

In yet another particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 39, and (4) an antibody light chain-encoding polynucleotide comprising a nucleotide sequence of SEQ ID NO: 41.

The Cell Line

In another aspect, the invention provides a cell line, which comprises a plurality of cells descended by clonal expansion from a cell described above. At least 50%, at least 60%, at least 70%, at least 80%, at least 90%, at least 95%, at least 98%, at least 99%, or about 100% of the constituent cells of the cell line contain a recombinant polynucleotide that encodes a stress-induced mannose-binding lectin, which in some embodiments is a component of the ERAD. In some embodiments, the stress-induced mannose-binding lectin is an endoplasmic reticulum degradation-enhancing alpha-mannosidase-like protein 2 (EDEM2). It is envisioned that any encoded EDEM2 or conservatively-substituted variant thereof can be successfully employed in the instant invention. Table 1, as discussed in the previous section, lists some examples of vertebrate EDEM2 proteins. In some embodiments, the constituent cell contains a polynucleotide that encodes an EDEM2 polypeptide having a sequence that is at least 92% identical to any mammalian EDEM2. In some embodiments, the constituent cell contains a polynucleotide that encodes an EDEM2 polypeptide having the mammalian consensus amino acid sequence of SEQ ID NO: 8. In some embodiments, the constituent cell contains a recombinant polynucleotide of SEQ ID NO: 1 or a conservatively substituted variant thereof.

In some embodiments, the multi-subunit protein that is produced by the cell line is an antibody, and the constituent cell of the cell line contains a polynucleotide encoding any one or more of a polypeptide comprising an amino acid sequence of SEQ ID NO: 43 and SEQ ID NO: 44 (which represent consensus sequences of the N-terminal and C-terminal portions, respectively, of particular antibody heavy chains), and SEQ ID NO: 45 and SEQ ID NO: 46 (which represent consensus sequences of the N-terminal and C-terminal portions, respectively, of particular antibody light chains). In some embodiments, in addition to the recombinant polynucleotide encoding the EDEM2 protein, the constituent cell of the cell line contains at least two polynucleotides, each of which encodes a particular subunit of the multi-subunit protein. For example, the constituent cell contains a polynucleotide encoding an antibody heavy chain comprising an amino acid sequence of SEQ ID NO: 43 and SEQ ID NO: 44, and another polynucleotide encoding an antibody light chain comprising an amino acid sequence of SEQ ID NO: 45 and SEQ ID NO: 46.

In some embodiments, the constituent cell, in addition to containing the stress-response polynucleotide and one or more polynucleotides encoding a polypeptide subunit, as described above, also contains a polynucleotide that encodes an unfolded protein response transcription factor, which operates upstream of EDEM2, such as a spliced form of an XBP1. It is envisioned that any encoded XBP1 can be successfully employed in the instant invention. Table 2, as discussed in the preceding section, lists some examples of sequences of vertebrate XBP1 spliced-form polypeptides. Clustal W analysis of those sequences revealed that each of the disclosed spliced XBP1 polynucleotide sequences is at least 48% identical to each other XBP1 sequence; and a comparison of the mammalian XBP1 sequences revealed that each sequence is at least 86% identical to the other. Thus, in some embodiments, the constituent cell of the cell line contains a polynucleotide that encodes a spliced-form of an XBP1 polypeptide having a sequence that is at least 86% to any one of a mammalian spliced XBP1. In some embodiments, the constituent cell contains a polynucleotide that encodes an XBP1 polypeptide having a consensus amino acid sequence of SEQ ID NO: 13.

In various embodiments, the cell contains a polynucleotide that encodes an XBP1 polypeptide having an amino acid sequence that is at least 86% identical to the mouse XBP1 (mXBP1) amino acid sequence (SEQ ID NO: 9); and in a particular embodiment, the polypeptide is mXBP1 of SEQ ID NO: 9, or a conservatively substituted variant thereof.

The invention envisions that the cell line comprises constituent cells whose parent is selected from a list of well-known protein production cells such as, e.g., the bacterium *Escherichia coli* and similar prokaryotic cells, the yeasts *Pichia pastoris* and other *Pichia* and non-*pichia* yeasts, plant cell explants, such as those of *Nicotiana*, insect cells, such as Schneider 2 cells, Sf9 and Sf21, and the *Trichoplusia ni*-derived High Five cells, and the mammalian cells typically used in bioproduction, such as CHO, CHO-K1, COS, HeLa, HEK293, Jurkat, and PC12 cells. In some embodiments, the cell is a CHO-K1 or a modified CHO-K1 cell, such as that which is taught in U.S. Pat. Nos. 7,435,553, 7,514,545, and 7,771,997, as well as U.S. Published Patent Application No. US 2010-0304436 A1.

In some embodiments, the cell line, which is cultured in media, is capable of producing the multi-subunit protein and secreting the properly assembled multi-subunit protein into the media to a titer that is at least 3 g/L, at least 5 g/L, or at least 8 g/L.

Furthermore, the constituent cells of the cell line are capable proliferating in culture to such an extent as to attain an integrated cell density that is about 30% greater than the integrated cell density of a cell line that does not contain the recombinant polynucleotide encoding the stress-induced mannose-binding lectin. In some cases, the cell line is able to attain an integrated cell density that is at least about 50% greater, at least 60% greater, or at least 90% greater than the integrated cell density of a cell line that does not contain the recombinant polynucleotide that encodes a stress-induced mannose-binding lectin. In some embodiments, the integrated cell density of the cell line is assessed after about 12 days in culture.

In some particular embodiments, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence that encodes a polypeptide comprising the amino acid sequences of SEQ ID NO: 43 and 44, and (4) an antibody light chain-encoding polynucleotide comprising a nucleotide sequence that encodes a polypeptide comprising the amino acid sequences of SEQ ID NO: 45 and 46.

In one particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 23, and (4) an antibody light chain-encoding polynucleotide comprising a nucleotide sequence of SEQ ID NO: 25.

In another particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 31, and (4) an antibody light chain-encoding polynucleotide comprising a nucleotide sequence of SEQ ID NO: 33.

In yet another particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 39, and (4) an antibody light chain-encoding polynucleotide comprising a nucleotide sequence of SEQ ID NO: 41.

The EDEM2 Polynucleotide

In another aspect, the invention provides a polynucleotide that encodes an EDEM2 protein. The EDEM2-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the EDEM2-encoding polynucleotide is within a gene, meaning that it is under the control of and down stream of a promoter, and up stream of a polyadenylation site. The EDEM2-encoding polynucleotide or gene can be within a plasmid or other circular or linear vector. The EDEM2-encoding polynucleotide or gene can be within a circular or linear DNA construct, which can be within a cell as an episome or integrated into the cellular genome.

As described above, the EDEM2-encoding polynucleotide encodes any ortholog, homolog or conservatively substituted EDEM2 polypeptide of Table 1, or an EDEM2 polypeptide having an amino acid sequence that is at least 92% identical to any one of SEQ ID NO: 1-5 and 8, including the mammalian consensus sequence of SEQ ID NO: 8.

In some cases, the recombinant or isolated EDEM2-encoding polynucleotide is operably linked to a mammalian promoter. The promoter can be any promoter, but in some cases it is a mammalian promoter, such as for example a ubiquitin C promoter.

In a particular embodiment, the EDEM2-encoding polynucleotide essentially consists of, from 5' to 3', a promoter, such as a ubiquitin C promoter, followed by an optional intron, such as a beta globin intron, followed by an EDEM2 coding sequence, followed by a polyadenylation sequence, such as an SV40pA sequence. A specific example, which is also a particular embodiment, of such an EDEM2-encoding polynucleotide is described by SEQ ID NO: 16. Conserved variants of that sequence are also envisioned to be embodiments of the invention.

In some cases, the recombinant EDEM2-encoding polynucleotide is part of a plasmid, which can be linear, circular, episomal, integrated, a static DNA construct, or a vector for delivering the EDEM2 gene or expressing the EDEM2 protein. In one particular embodiment, the plasmid contains (1) an EDEM2 gene, which is under the control of a ubiquitin C promoter and terminates with an SV40 polyadenylation signal, and (2) a selectable marker, such as a polynucleotide encoding a polypeptide that confers resistance to zeocin or a polynucleotide encoding a polypeptide that confers resistance to neomycin, under the control of a promoter, such as an SV40 promoter, and terminated with a polyadenylation sequence, such as a PGK pA sequence. In one particular embodiment, the plasmid comprises, in a circular format running in a 5' to 3' direction, a ubiquitin C promotor, a beta globin intron, an EDEM2 coding sequence, an SV40 pA sequence, an SV40 promoter, a neomycin-resistance coding sequence, and a PGK pA sequence. A specific example of this embodiment is exemplified by a plasmid having the sequence of SEQ ID NO: 14. In another particular embodiment, the plasmid comprises, in a circular format running in a 5' to 3' direction, a ubiquitin C promotor, a beta globin intron, an EDEM2 coding sequence, an SV40 pA sequence, an SV40 promoter, a zeocin-resistance coding sequence, and a PGK pA sequence. A specific example of this embodiment is exemplified by a plasmid having the sequence of SEQ ID NO: 15.

The XBP1 Polynucleotide

In another aspect, the invention provides a polynucleotide that encodes an XBP1 protein. The XBP1-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the XBP1-encoding polynucleotide is within a gene, meaning that it is under the control of and down stream of a promoter, and up stream of a polyadenylation site. The XBP1-encoding polynucleotide can be within a plasmid or other circular or linear vector. The XBP1-encoding polynucleotide or gene can be within a circular or linear DNA construct, which can be within a cell as an episome, or integrated into the cellular genome.

As described above, the XBP1-encoding polynucleotide encodes any ortholog, homolog or conservatively substituted XBP1 polypeptide of Table 2, or an XBP1 polypeptide having an amino acid sequence that is at least 86% identical to any one of SEQ ID NO: 9, 10, and 11, including the mammalian consensus sequence of SEQ ID NO: 13.

In some cases, the recombinant or isolated XBP1-encoding polynucleotide is operably linked to a mammalian promoter. The promoter can be any promoter, but in some cases it is a mammalian promoter, such as for example a ubiquitin C promoter.

In a particular embodiment, the XBP1-encoding polynucleotide essentially consists of, from 5' to 3', a promoter, such as a ubiquitin C promoter, followed by an optional intron, such as a beta globin intron, followed by an XBP1 coding sequence, followed by a polyadenylation sequence, such as an SV40 pA sequence. SEQ ID NO: 18 describes an example of an XBP1-encoding polynucleotide. Conserved variants of that exemplary sequence are also envisioned to be embodiments of the invention.

In some cases, the recombinant XBP1-encoding polynucleotide is part of a plasmid, which can be linear, circular, episomal, integrated, a static DNA construct, or a vector for delivering the XBP1 gene or expressing the spliced and active XBP1 protein. In one particular embodiment, the plasmid contains (1) an XBP1 gene, which is under the control of a ubiquitin C promoter and terminates with an SV40 polyadenylation signal, and (2) a selectable marker, such as a polynucleotide encoding a polypeptide that confers resistance to zeocin or a polynucleotide encoding a polypeptide that confers resistance to neomycin, under the control of a promoter, such as an SV40 promoter, and terminated with a polyadenylation sequence, such as a PGK pA sequence. In one particular embodiment, the plasmid comprises, in a circular format running in a 5' to 3' direction, a ubiquitin C promotor, a beta globin intron, an XBP1 coding sequence, an SV40 pA sequence, an SV40 promoter, a zeocin-resistance coding sequence, and a PGK pA sequence. A specific example of this embodiment is exemplified by a circular plasmid having the sequence of SEQ ID NO: 17.

The Antibody Heavy and Light Chain-Encoding Polynucleotides

In another aspect, the invention provides a polynucleotide that encodes an antibody heavy chain polypeptide (HC). The HC-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the HC-encoding polynucleotide is within a gene, meaning that it is under the control of and down stream from a promoter, and up stream of a polyadenylation site. The HC-encoding polynucleotide may be within a plasmid or other circular or linear vector. The HC-encoding polynucleotide or gene may be within a circular or linear DNA construct, which may be within a cell as an episome or integrated into the cellular genome.

In some cases, the recombinant or isolated HC-encoding polynucleotide is operably linked to a mammalian promoter. The promoter can be any promoter, but in some cases it is a mammalian promoter, such as for example a ubiquitin C promoter or an hCMV-IE promoter.

In a particular embodiment, the HC-encoding polynucleotide is an HC gene, which essentially comprises, from 5' to 3', a promoter, for example an hCMV-IE promoter, followed by an optional intron, such as a beta globin intron, followed by a heavy chain coding sequence, such as for example a sequence encoding an amino acid sequence of SEQ ID NO: 43 and 44, SEQ ID NO: 19, SEQ ID NO: 27, or SEQ ID NO: 35, followed by a polyadenylation sequence, for example an SV40 pA sequence. A specific example of an HC gene is described by SEQ ID NO: 23, SEQ ID NO: 31, or SEQ ID NO: 39. Conserved variants of any one of these sequences are also envisioned to be embodiments of the invention.

In some cases, the recombinant HC-encoding polynucleotide is part of a plasmid, which can be linear, circular, episomal, integrated, a static DNA construct, or a vector for delivering the heavy chain gene or expressing the heavy chain subunit. In one particular embodiment, the plasmid contains (1) an HC gene, which is under the control of an hCMV-IE promoter and terminates with an SV40 polyadenylation signal, and (2) a selectable marker, such as a polynucleotide encoding a polypeptide that confers resistance to hygromycin, under the control of a promoter, such as an SV40 promoter, and terminated with a polyadenylation sequence, such as a PGK pA sequence. In one particular embodiment, the plasmid comprises, in a circular format running in a 5' to 3' direction, an hCMV-IE promoter, a beta globin intron, an antibody heavy chain coding sequence (which encodes a HC having an amino acid of SEQ ID NO: 43 and 44, SEQ ID NO: 19, SEQ ID NO: 27, or SEQ ID NO: 35), an SV40 pA sequence, an SV40 promoter, a hygromycin-resistance coding sequence, and a PGK pA sequence. A specific example and particular embodiment of such a plasmid containing an HC gene is described by SEQ ID NO: 24, SEQ ID NO: 32, or SEQ ID NO: 40. Conserved variants of any one of these sequences are also envisioned to be embodiments of the invention.

In another aspect, the invention provides a polynucleotide that encodes an antibody light chain polypeptide (LC). The LC-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the LC-encoding polynucleotide is within a gene, meaning that it is under the control of and down stream from a promoter, and up stream of a polyadenylation site. The LC-encoding polynucleotide or gene may be within a plasmid or other circular or linear vector. The LC-encoding polynucleotide or gene may be within a circular or linear DNA construct, which may be within a cell as an episome or integrated into the cellular genome.

In some cases, the recombinant or isolated LC-encoding polynucleotide is operably linked to a mammalian promoter. The promoter can be any promoter, but in some cases it is a mammalian promoter, such as, e.g., a ubiquitin C promoter or an hCMV-IE promoter.

In a particular embodiment, the LC-encoding polynucleotide is an LC gene, which essentially comprises, from 5' to 3', a promoter, for example an hCMV-IE promoter, followed by an optional intron, such as a beta globin intron, followed by a light chain coding sequence, such as for example a sequence encoding an amino acid sequence of SEQ ID NO: 45 and 46, SEQ ID NO: 21, SEQ ID NO: 29, or SEQ ID NO: 37, followed by a polyadenylation sequence, such as an SV40 pA sequence. A specific example and particular embodiment of such an LC gene is described by SEQ ID NO: 25, SEQ ID NO: 33, or SEQ ID NO: 41. Conserved variants of any one of these sequences are also envisioned to be embodiments of the invention.

In some cases, the recombinant LC-encoding polynucleotide is part of a plasmid, which may be linear, circular, episomal, integrated, a static DNA construct, or a vector for delivering the light chain gene or expressing the light chain subunit. In one particular embodiment, the plasmid contains (1) an LC gene, which is under the control of an hCMV-IE promoter and terminates with an SV40 polyadenylation signal, and (2) a selectable marker, such as a polynucleotide encoding a polypeptide that confers resistance to hygromycin, under the control of a promoter, such as an SV40 promoter, and terminated with a polyadenylation sequence, such as a PGK pA sequence. In one particular embodiment, the plasmid comprises, in a circular format running in a 5' to 3' direction, an hCMV-IE promoter, a beta globin intron, an antibody light chain coding sequence (which encodes a LC having an amino acid of SEQ ID NO: 45 and 46, SEQ ID NO: 21, SEQ ID NO: 29, or SEQ ID NO: 37), an SV40 pA sequence, an SV40 promoter, a hygromycin-resistance coding sequence, and a PGK pA sequence. A specific example and particular embodiment of such a plasmid containing an LC gene is described by SEQ ID NO: 26, SEQ ID NO: 34, or SEQ ID NO: 42. Conserved variants of any one of these sequences are also envisioned to be embodiments of the invention.

Methods of Manufacturing Multi-Subunit Proteins

In another aspect, the invention provides a method for manufacturing a multi-subunit protein by culturing a cell, or a constituent cell of a cell line, which is capable of producing and secreting relatively large amounts of a properly assembled multi-subunit protein, in a medium, wherein the multi-subunit component is secreted into the medium at a relatively high titer. The cell utilized in this manufacturing process is a cell described in the foregoing aspects, which contains an ERAD lectin-encoding polynucleotide described herein.

Methods of culturing cells, and in particular mammalian cells, for the purpose of producing useful recombinant proteins is well-known in the art (e.g., see De Jesus & Wurm, Eur. J. Pharm. Biopharm. 78:184-188, 2011, and references cited therein). Briefly, cells containing the described polynucleotides are cultured in media, which may contain sera or hydrolysates, or may be chemically defined and optimized for protein production. The cultures may be fed-batch cultures or continuous cultures, as in a chemostat. The cells may be cultured in lab bench size flasks (~25 mL), production scale-up bioreactors (1-5 L), or industrial scale bioreactors (5,000-25,000 L). Production runs may last for several weeks to a month, during which time the multi-subunit protein is secreted into the media.

The subject cell has an enhanced ability to produce and secrete properly assembled multi-subunit proteins. In some embodiments, the multi-subunit protein, for example an antibody, is secreted into the media at a rate of at least 94 pg/cell/day, at least 37 pg/cell/day, or at least 39 pg/cell/day. In some embodiments, the multi-subunit protein attains a titer of at least at least 3 g/L, at least 5 g/L, at least 6 g/L, or at least 8 g/L after about twelve days of culture.

Furthermore, the subject cell has an enhanced ability to proliferate and attain a relatively high cell density, further optimizing productivity. In some embodiments, the cell or cell-line seed train attains an integrated cell density in culture of at least $5 \times 10^7$ cell-day/mL, at least $1 \times 10^8$ cell-day/mL or at least $1.5 \times 10^8$ cell-day/mL.

Optionally, the secreted multi-subunit protein is subsequently purified from the medium into which it was secreted. Protein purification methods are well-known in the art (see e.g., Kelley, mAbs 1(5):443-452). In some embodiments, the protein is harvested by centrifugation to remove the cells from the liquid media supernatant, followed by various chromatography steps and a filtration step to remove inter alia viruses and other contaminants or adulterants. In some embodiments, the chromatography steps include an ion exchange step, such as cation-exchange or anion-exchange. Various affinity chromatographic media may also be employed, such as protein A chromatography for the purification of antibodies.

Optionally, the manufacturing method may include the antecedent steps of creating the cell. Thus, in some embodiments, the method of manufacturing the multi-subunit protein comprises the step of transfecting the cell with the vector that encodes the stress-induced mannose-binding lectin, as described above, followed by selecting stable integrants thereof. Non-limiting examples of vectors include those genetic constructs that contain a polynucleotide that encodes an EDEM2 having an amino acid sequence of any one of SEQ ID NO: 1-8, an amino acid sequence that is at least 92% identical to any one of SEQ ID NO: 1-8, or any one of a conservatively substituted variant of SEQ ID NO: 1-8. Useful vectors also include, for example, a plasmid harboring the gene of SEQ ID NO: 16, the plasmid of SEQ ID NO: 15, and the plasmid of SEQ ID NO: 14. One should keep in mind that the plasmid sequences (e.g., SEQ ID NO: 14, 15, 17, 24, 26, 32, 34, 40, and 42) are circular sequences described in a linear manner in the sequence listing. Thus, in those cases, the 3-prime-most nucleotide of the written sequence may be considered to be immediately 5-prime of the 5-prime-most nucleotide of the sequence as written. In the example of the plasmid of SEQ ID NO: 14, transformants are selected through resistance to neomycin; for SEQ ID NO: 15, by selection through ZEOCIN resistance.

Detailed methods for the construction of polynucleotides and vectors comprising same, are described in U.S. Pat. Nos. 7,435,553 and 7,771,997, which are incorporated herein by reference, and in, e.g., Zwarthoff et al., J. Gen. Virol. 66(4):685-91, 1985; Mory et al., DNA. 5(3):181-93, 1986; and Pichler et al., Biotechnol. Bioeng. 108(2):386-94, 2011.

The starting cell, into which the vector that encodes the stress-induced mannose-binding lectin is placed, may already contain the constructs or genetic elements encoding or regulating the expression of the subunits of the multi-subunit protein, or XBP1 for those embodiments utilizing XBP1. Alternatively, the vector that encodes the stress-induced mannose-binding lectin may be put inside the cell first, and followed by the other constructs.

Multi-Subunit Proteins Manufactured by the Process

In another aspect, the invention provides a multi-subunit protein that is made according to the process disclosed herein. Given the inclusion of one or more elements that facilitate the proper folding, assembly, and post-translational modification of a multi-subunit protein, such as an antibody, one of ordinary skill in the art would reasonably expect such a protein to have distinct structural and functional qualities. For example, an antibody manufactured by the disclosed process is reasonably believed to have a particular glycosylation pattern and a quantitatively greater proportion of non-aggregated heterotetramers.

EXAMPLES

The following examples are presented so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by mole, molecular weight is average molecular weight, percent concentration (%) means the mass of the solute in grams divided by the volume of the solution in milliliters times 100% (e.g., 10% substance X means 0.1 gram of substance X per milliliter of solution), temperature is in degrees Centigrade, and pressure is at or near atmospheric pressure.

Example 1: Cell Lines

CHO-K1 derived host cell line was transfected with two plasmids encoding heavy and light chain of a human antibody. Both plasmids contain the hph gene conferring resistance to hygromycin B (Asselbergs and Pronk, 1992, Mol. Biol. Rep., 17(1):61-70). Cells were transfected using LIPOFECTAMIN reagent (Invitrogen cat.#18324020). Briefly, one day before transfection 3.5 million cells were plated on a 10 cm plate in complete F12 (Invitrogen cat.#11765) containing 10% fetal bovine serum (FBS) (Invitrogen cat.#10100). On the day of transfection the cells were washed once and medium was replaced with OPTIMEM from (Invitrogen cat.#31985). DNA/Lipofectamin complexes were prepared in OPTIMEM medium and then added to the cells. The medium was changed again to the complete F12 with 10% FBS 6 hours later. The stable integration of the plasmids was selected using hygromycin B selection agent at 400 μg/ml. Clonal antibody expressing cell lines were isolated using the FASTR technology (described in the U.S. Pat. No. 6,919,183, which is herein incorporated by reference).

The antibody expressing lines were then re-transfected with the EDEM2 encoding plasmid. EDEM2 plasmids contained either neomycin phosphotransferase (plasmid construct designated "p3") or sh ble (plasmid "p7") genes to confer resistance to either G418 or zeocin respectively. The same transfection method was used. Depending on the selectable marker, cells were selected with either G418 or zeocin at 400 μg/ml or 250 μg/ml, respectively. The clonal cell lines were then isolated using FASTR technology.

TABLE 3

Cell Lines

| Name | Enhancers | Constructs | Protein |
|---|---|---|---|
| C1 | EDEM2 + XBP1 | HC/LC = p1/p2 | αAng2 |
| C2 | XBP1 | EDEM2 = p3 | |
| | | XBP1 = p4 | |
| C3 | EDEM2 + XBP1 | HC/LC = p5/p6 | αGDF8 |
| C4 | XBP1 | EDEM2 = p7 | |
| C5 | EDEM2 | XBP1 = p4 | |
| C6 | EDEM2 + XBP1 | HC/LC = p8/p9 | αAngPtl4 |
| C7 | XBP1 | EDEM2 = p3 | |
| | | XBP1 = p4 | |

Example 2

The antibody production was evaluated in a scaled-down 12-day fed batch process using shaker flasks. In this method the cells were seeded in a shaker flask at the density of 0.8 million cells per mL in the production medium (defined media with high amino acid). The culture was maintained for about 12 days, and was supplemented with three feeds as well as glucose. The viable cell density, and antibody titer were monitored throughout the batch.

To determine the effect of mEDEM2 on enhanced protein production, the production of proteins by CHO cell lines containing mEDEM2 and mXBP1 were compared to production by control cells that contained mXBP1, but not mEDEM2. Protein titers were higher in those cell lines expressing mEDEM2 versus those cell lines that did not express mEDEM2.

TABLE 4

| | | TITERS | |
| --- | --- | --- | --- |
| Cell Line | Enhancers | Production rate (pg/cell/day) | Titre g/L (% increase) |
| C1 | EDEM2 + XBP1 | 39 | 8.1 (93) |
| C2 | XBP1 | 39 | 4.2 |
| C3 | EDEM2 + XBP1 | 37 | 5.9 (55) |
| C8 | XBP1 | 32 | 3.8 |
| C6 | EDEM2 + XBP1 | 94 | 5.3 (152) |
| C7 | XBP1 | 52 | 2.1 |
| C5 | EDEM2 | 29 | 3.1 (343) |
| C9 | — | 9 | 0.7 |

Example 3: Integrated Cell Days

Integrated Cell Days ("ICD") is a phrase used to describe the growth of the culture throughout the fed batch process. In the course of the 12-day production assay, we monitored viable cell density on days 0, 3, 5, 7, 10, and 12. This data was then plotted against time. ICD is the integral of viable cell density, calculated as the area under the cell density curve. EDEM2 transfected lines have higher ICD in a 12-day fed batch process (see Table 5).

TABLE 5

| | INTEGRATED CELL DENSITIES | |
| --- | --- | --- |
| Cell Line | Enhancers | ICD $10^6$ cell-day/mL (% increase) |
| C1 | EDEM2 + XBP1 | 205 (93) |
| C2 | XBP1 | 106 |
| C3 | EDEM2 + XBP1 | 157 (34) |
| C4 | XBP1 | 117 |
| C6 | EDEM2 + XBP1 | 56 (51) |
| C7 | XBP1 | 37 |
| C5 | EDEM2 | 116 (59) |
| C9 | — | 73 |

Example 4: Anti-GDF8 Antibody Production

The effect of ectopic expression of EDEM2, XBP1, or both on the production of an anti-GDF8 antibody having a heavy chain sequence of SEQ ID NO: 19 and a light chain sequence of SEQ ID NO: 21 was examined. Individual cell-lines were examined for titer and integrated cell density and placed into "bins", or ranges of values. Ectopic expression of EDEM2 significantly increased the number of cell lines that express antibody in the 5-6 g/L titer range. The combination of XBP1 and EDEM2 showed more than an additive effect toward the increase in high titer cell lines. The expression of EDEM2 in the antibody secreting cells also significantly increased the number of cell lines that attain a high ICD (see Table 6).

TABLE 6

| con-struct | Titre Bins (g/L) | | | | ICD Bins ($10^6$ cell-day/mL) | | |
| --- | --- | --- | --- | --- | --- | --- | --- |
| | <1 | 1-3 | 3-5 | 5-6 | 30-50 | 50-100 | 100-200 |
| E + X | 0% | 33.3% | 44.4% | 22.2% | 11.1% | 50% | 38.9% |
| X | 0% | 37.5% | 54% | 8.3% | 14.3% | 85.7% | 0% |
| E | 0% | 33% | 60% | 7% | 0% | 27% | 73% |
| — | 82% | 18% | 0% | 0% | 13% | 67% | 21% |

What is claimed is:

1. A recombinant host cell comprising an exogenous recombinant polynucleotide that encodes (i) an endoplasmic reticulum degradation-enhancing alpha-mannosidase-like protein 2 (EDEM2) selected from (a) an amino acid sequence of SEQ ID NO: 8 or (b) an amino acid sequence that is at least 92% identical to SEQ ID NO: 1, and (ii) an antibody or antigen-binding fragment thereof.

2. The cell of claim 1, wherein the antibody consists of a heavy chain and a light chain.

3. The cell of claim 2, wherein the heavy chain of the antibody comprises an amino acid sequences of SEQ ID NO: 43 and SEQ ID NO: 44 and the light chain of the antibody comprises an amino acid sequences of SEQ ID NO: 45 and SEQ ID NO: 46.

4. The cell of claim 1, further comprising a polynucleotide that encodes an unfolded protein response transcription factor that operates upstream of EDEM2.

5. The cell of claim 4, wherein the transcription factor is a spliced form of X-box binding protein 1 (XBP-1).

6. The cell of claim 5, wherein the XBP-1 comprises an amino acid sequence of SEQ ID NO: 13.

7. The cell of claim 5, wherein the XBP-1 comprises an amino acid sequence that is at least 86% identical to SEQ ID NO: 9.

8. The cell of claim 2, wherein the cell is a mammalian cell.

9. The cell of claim 8, wherein the cell is a CHO cell.

10. A cell line comprising the cell of claim 9.

11. The cell line of claim 10, which produces the antibody or antigen-binding fragment thereof at a titer of at least 3 g/L.

12. The cell line of claim 10, which produces the antibody or antigen-binding fragment thereof at a titer of at least 5 g/L.

13. The cell line of claim 10, which produces the antibody or antigen-binding fragment thereof at a titer of at least 8 g/L.

14. The cell line of claim 10, wherein the integrated cell density is at least 30% greater than the integrated cell density of a cell line that does not comprise the recombinant polynucleotide that encodes an EDEM2.

15. The cell line of claim 10, wherein the integrated cell density is at least 50% greater than the integrated cell density of a cell line that does not comprise the recombinant polynucleotide that encodes an EDEM2.

16. The cell line of claim 10, wherein the integrated cell density is at least 60% greater than the integrated cell density of a cell line that does not comprise the recombinant polynucleotide that encodes an EDEM2.

17. The cell line of claim 10, wherein the integrated cell density is at least 90% greater than the integrated cell density of a cell line that does not comprise the recombinant polynucleotide that encodes an EDEM2.

18. The cell of claim 1, wherein the antibody is selected from the group consisting of an anti-GDF8 antibody, and anti-AGN2 antibody, and an anti-ANGPTL4 antibody.

19. The cell of claim 2, wherein a heavy chain of the antibody comprises an amino acid sequence of SEQ ID NO: 19 and a light chain of the antibody comprises an amino acid sequence of SEQ ID NO: 21.

20. The cell of claim 2, wherein a heavy chain of the antibody comprises an amino acid sequence of SEQ ID NO: 27 and a light chain of the antibody comprises an amino acid sequence of SEQ ID NO: 29.

21. The cell of claim 2, wherein a heavy chain of the antibody comprises an amino acid sequence of SEQ ID NO: 35 and a light chain of the antibody comprises an amino acid sequence of SEQ ID NO: 37.

* * * * *